United States Patent
Kelly et al.

(10) Patent No.: US 11,249,085 B2
(45) Date of Patent: Feb. 15, 2022

(54) APPLICATION OF CLICK CHEMISTRY FOR SIGNAL AMPLIFICATION IN IHC AND ISH ASSAYS

(71) Applicant: Ventana Medical Systems, Inc., Tucson, AZ (US)

(72) Inventors: Brian D. Kelly, Tucson, AZ (US); Nathan W. Polaske, Oracle, AZ (US)

(73) Assignee: Ventana Medical Systems, Inc., Tucson, AZ (US)

(*) Notice: Subject to any disclaimer, the term of this patent is extended or adjusted under 35 U.S.C. 154(b) by 66 days.

(21) Appl. No.: 16/226,489

(22) Filed: Dec. 19, 2018

(65) Prior Publication Data

US 2019/0204330 A1 Jul. 4, 2019

Related U.S. Application Data

(63) Continuation of application No. PCT/EP2017/065796, filed on Jun. 27, 2017.

(60) Provisional application No. 62/355,390, filed on Jun. 28, 2016.

(51) Int. Cl.
| | |
|---|---|
| G01N 33/58 | (2006.01) |
| C07F 9/12 | (2006.01) |
| C07F 9/553 | (2006.01) |
| C07F 9/6524 | (2006.01) |
| C07F 9/6518 | (2006.01) |
| C07F 9/6509 | (2006.01) |

(52) U.S. Cl.
CPC .......... *G01N 33/582* (2013.01); *C07F 9/12* (2013.01); *C07F 9/5535* (2013.01); *C07F 9/6518* (2013.01); *C07F 9/6524* (2013.01); *C07F 9/650947* (2013.01)

(58) Field of Classification Search
CPC .... C07F 9/6524; C07F 9/650947; C07F 9/12; C07F 9/6518; C07F 9/5535; G01N 33/582

See application file for complete search history.

(56) References Cited

U.S. PATENT DOCUMENTS

| | | | |
|---|---|---|---|
| 5,583,001 | A | 12/1996 | Bobrow et al. |
| 8,900,549 | B2 | 12/2014 | Hilderbrand et al. |
| 9,447,455 | B2 * | 9/2016 | Hu ............... C12Q 1/6816 |
| 2012/0029186 | A1 | 2/2012 | Popik |
| 2012/0171668 | A1 | 7/2012 | May et al. |

(Continued)

FOREIGN PATENT DOCUMENTS

| | | |
|---|---|---|
| CN | 102271712 A | 12/2011 |
| JP | 2010122071 A | 6/2010 |
| JP | 2015534996 A | 12/2015 |

(Continued)

OTHER PUBLICATIONS

Kuzmin et al. Surface functionalization using catalyst-free azide-alkyne cycloaddition. Bioconjugate Chem. 2010, vol. 21, pp. 2076-2085. (Year: 2010).*

(Continued)

*Primary Examiner* — Shafiqul Haq
(74) *Attorney, Agent, or Firm* — Charney IP Law LLC; Thomas M. Finetti

(57) ABSTRACT

Applicants have developed an amplification system and methodology for IHC and ISH staining that utilizes "click chemistry" to covalently bind reporter molecules to tissue.

18 Claims, 22 Drawing Sheets
(16 of 22 Drawing Sheet(s) Filed in Color)

(56) References Cited

U.S. PATENT DOCUMENTS

2012/0208722 A1     8/2012   Dluhy
2013/0281656 A1   10/2013   Popik et al.

FOREIGN PATENT DOCUMENTS

| WO | 2010051530 A2 | 5/2010 |
|---|---|---|
| WO | 2012152807 A1 | 11/2012 |
| WO | 2013148498 A1 | 10/2013 |
| WO | 2014065661 A1 | 5/2014 |
| WO | 2015124703 A1 | 8/2015 |
| WO | 2015154082 A1 | 10/2015 |

OTHER PUBLICATIONS

Karver et al. Bioorthogonal reaction parirs enable sumultaneous, selective, multi-target imaging. Angew Int Ed Engl. 2012, vol. 51, No. 4, pp. 920-922. (Year: 2012).*

Xu et al. Cytocompatible polyethylene glycol)—co-polycarbonate hydrogels crosslinked by copper-free, strain-promoted "click" chemistry. Chem Asian J. 2011, vol. 6, No. 10, pp. 2730-2737. (Year: 2011).*

Chan D. et al, Double Click: Dual Functionalized Polimeric Micelles with Antibodies and Peptides, Bioconjugate Chem., (2013), pp. 105-113, vol. 24.

"OptiView Detection Chemistry", published 2011 at http://www.ventana.com/documents/OptiView_F&B_Brochure.pdf, pp. 1-4.

"Ventana OptiView DAB IHC Detection Kit Product Sheet", Jun. 23, 2011, pp. 1-4.

Deiters et al., Adding Amino Acids with Novel Reactivity to the Genetic Code of *Saccharomyces cerevisiae*, Journal of the American Chemical Society, 2003, pp. 11782-11783, 125.

Fazio et al., Synthesis of Sugar Arrays in Microtiter Plate, Journal of the American Chemical Society, 2002, pp. 14397-14402, 124.

International Search Report and Written Opinion dated Nov. 15, 2017 in corresponding PCT/EP2017/065796 filed Jun. 27, 2017, pp. 1-21.

Kolb et al., Click Chemistry: Diverse Chemical Function from a Few Good Reactions, Angewandte Chemie International Edition, 2001, pp. 2004-2021, 40.

Lee et al., A Potent and Highly Selective Inhibitor of Human alpha-1,3-Fucosyltransferase via Click Chemistry, Journal of the Amercian Chemical Society, 2003, pp. 9588-9589, 125.

Lewis et al., Click Chemistry in Situ: Acetylcholinesterase as a Reaction Vessel for the Selective Assembly of a Femtomolar Inhibitor from an Array of Building Blocks, Angewandte Chemie International Edition, 2002, pp. 1053-1057, 41, No. 6.

Link et al., Cell Surface Labeling of *Escherichia coli* via Copper(I)—Catalyzed [3+2] Cycloaddition, Journal of the American Chemical Society, 2003, pp. 11164-11165, 125.

Meng et al., Cleavable Linkers for Porous Silicon-Based Mass Spectrometry, Angewandte Chemie International Edition, 2004, pp. 1255-1260, 43.

OPTIVIEW® Amplification Kit, Ventana Medical Systems, Tucson AZ, Catalog No. 760-099, 2012, pp. 1-2.

Rostovtsev, et al. A stepwise huisgen cycloaddition process: copper(I)—catalyzed regioselective "ligation" of azides and terminal alcynes. Angew Chem Int Ed Engl. Jul. 15, 2002;41(14):2596-9.

Speers et al., Activity-Based Protein Profiling in Vivo Using a Copper(I)—Catalyzed Azide-Alkyne [3 + 2] Cycloaddition, Journal of the American Chemical Society, 2003, pp. 4686-4687, 125.

Wang et al., Bioconjugation by Copper(I)—Catalyzed Azide-Alkyne [3 + 2] Cycloaddition, Journal of the American Chemical Society, 2003, pp. 3192-3193, 125.

Xu et al., "Cytocompatible poly(ethylene glycol)—co-polycarbonate hydrogels crosslinked by copper-free, strain-promoted click chemistry," Chem Asian J. 2011.

Kuzmin et al., "Surface functionalization using catalyst-free azide-alkyne cycloaddition," Bioconjugate Chem. 2010.

Karver et al., "Bioorthogonal reaction parirs enable sumultaneous, selective, multi-target imaging," Angew Int Ed Engl. 2012.

* cited by examiner

— Bcl6 on tonsil —

*QMP-Azide : TAMRA-DBCO*

— Ki67 on tonsil —

QMP-TCO : TAMRA-Tetrazine

Ki67 on tonsil

TYR-DBCO: TAMRA-Azide

CD8 on tonsil

*TYR-TCO: TAMRA-Tetrazine*

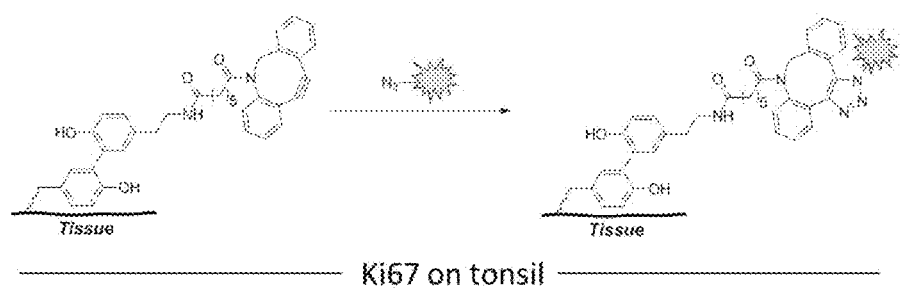
FIG. 9E
Ki67 on tonsil
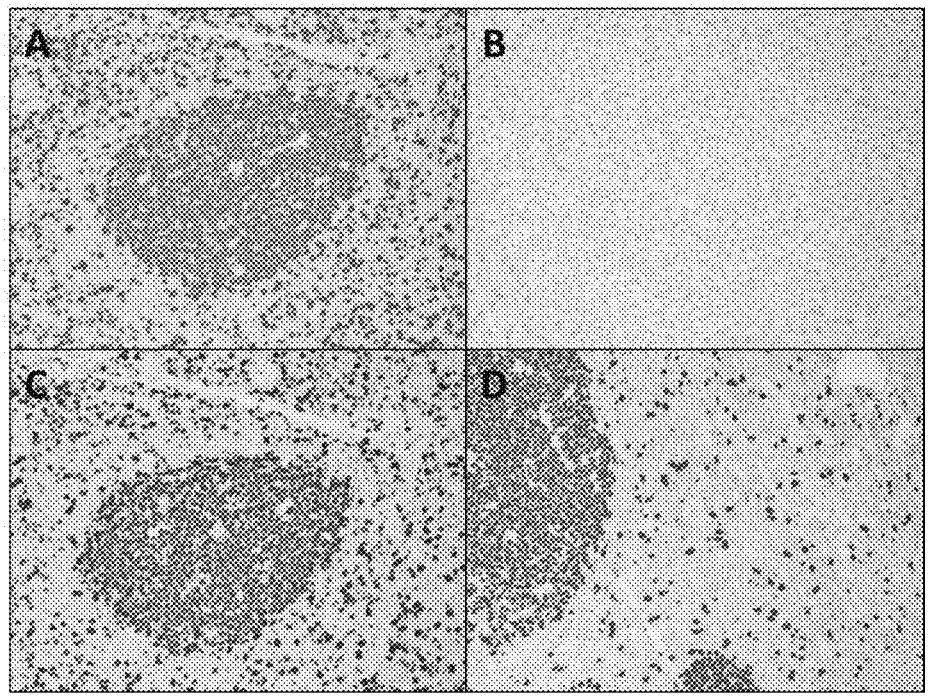
FIG. 9A
FIG. 9B
FIG. 9C
FIG. 9D

——— BCL6 on tonsil ———
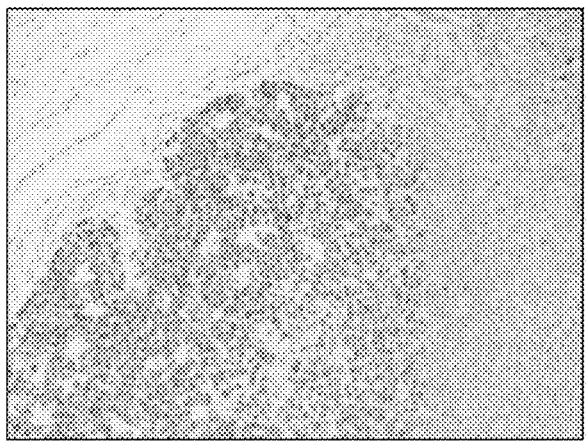
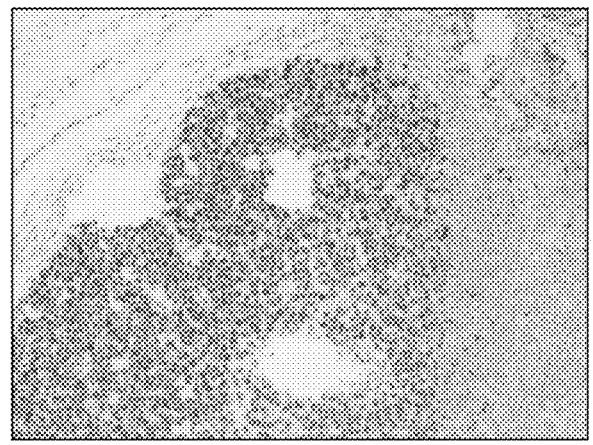
FIG. 12C  FIG. 12D

APPLICATION OF CLICK CHEMISTRY FOR SIGNAL AMPLIFICATION IN IHC AND ISH ASSAYS

CROSS REFERENCE TO RELATED APPLICATIONS

This application is a continuation of PCT/EP2017/065796, filed Jun. 27, 2017, which claims the benefit of U.S. Provisional Application No. 62/355,390, filed Jun. 28, 2016, the content of each of which is incorporated herein by reference in its entirety.

BACKGROUND OF THE DISCLOSURE

Field of the Invention

The present disclosure has industrial applicability in the fields of chemistry and diagnostics.

Description of the Related Art

Immunohistochemistry (IHC) refers to the processes of detecting, localizing, and/or quantifying antigens, such as a protein, in a biological sample using antibodies specific to the particular antigens. IHC provides the substantial advantage of identifying exactly where a particular protein is located within the tissue sample. It is also an effective way to examine the tissues themselves. In situ hybridization (ISH) refers to the process of detecting, localizing, and quantifying nucleic acids. Both IHC and ISH can be performed on various biological samples, such as tissue (e.g. fresh frozen, formalin fixed, paraffin embedded) and cytological samples. Recognition of the targets can be detected using various labels (e.g., chromogenic, fluorescent, luminescent, radiometric), irrespective of whether the target is a nucleic acid or an antigen. To robustly detect, locate, and quantify targets in a clinical setting, amplification of the recognition event is desirable as the ability to confidently detect cellular markers of low abundance becomes increasingly important for diagnostic purposes. For example, depositing at the marker's site hundreds or thousands of label molecules in response to a single antigen detection event enhances, through amplification, the ability to detect that recognition event.

Adverse events often accompany amplification, such as non-specific signals that are apparent as an increased background signal. An increased background signal interferes with the clinical analysis by obscuring faint signals that may be associated with low, but clinically significant, expressions. Accordingly, while amplification of recognition events is desirable, amplification methods that do not increase background signal are highly desirable. One such method is Tyramide Signal Amplification (TSA), which has also been referred to as catalyzed reporter deposition (CARD). U.S. Pat. No. 5,583,001 discloses a method for detecting and/or quantitating an analyte using an analyte-dependent enzyme activation system that relies on catalyzed reporter deposition to amplify the detectable label signal. Catalysis of an enzyme in a CARD or TSA method is enhanced by reacting a labeled phenol molecule with an enzyme. Modern methods utilizing TSA effectively increase the signals obtained from IHC and ISH assays while not producing significant background signal amplification (see, for example, U.S. application publication No. 2012/0171668 which is hereby incorporated by reference in its entirety for disclosure related to tyramide amplification reagents). Reagents for these amplification approaches are being applied to clinically important targets to provide robust diagnostic capabilities previously unattainable (VENTANA OptiView Amplification Kit, Ventana Medical Systems, Tucson Ariz., Catalog No. 760-099).

TSA takes advantage of the reaction between horseradish peroxidase (HRP) and tyramide. In the presence of $H_2O_2$, tyramide is converted to a highly-reactive and short-lived radical intermediate that reacts preferentially with electron-rich amino acid residues on proteins. Covalently-bound detectable labels can then be detected by variety of chromogenic visualization techniques and/or by fluorescence microscopy. In solid-phase immunoassays, such as IHC and ISH, where spatial and morphological context is highly valued, the short lifetime of the radical intermediate results in covalent binding of the tyramide to proteins on tissue in close proximity to the site of generation, giving discrete and specific signal.

Application PCT/EP2015/053556 entitled "Quinone Methide Analog Signal Amplification," having an international filing date of Feb. 20, 2015, describes an alternative technique ("QMSA") that, like TSA, may be used to increase signal amplification without increasing background signals. Indeed, PCT/EP2015/053556 describes novel quinone methide analog precursors and methods of using the quinone methide analog precursors in detecting one or more targets in a biological sample. There, the method of detection is described as comprising the steps of contacting the sample with a detection probe, then contacting the sample with a labeling conjugate that comprises an enzyme. The enzyme interacts with a quinone methide analog precursor comprising a detectable label, forming a reactive quinone methide analog, which binds to the biological sample proximally to or directly on the target. The detectable label is then detected.

"Click chemistry" is a chemical philosophy, independently defined by the groups of Sharpless and Meldal, that describes chemistry tailored to generate substances quickly and reliably by joining small units together. "Click chemistry" has been applied to a collection of reliable and self-directed organic reactions (Kolb, H. C.; Finn, M. G.; Sharpless, K. B. Angew. Chem. Int. Ed. 2001, 40, 2004-2021). For example, the identification of the copper catalyzed azide-alkyne [3+2]cycloaddition as a highly reliable molecular connection in water (Rostovtsev, V. V.; et al. Angew. Chem. Int. Ed. 2002, 41, 2596-2599) has been used to augment several types of investigations of biomolecular interactions (Wang, Q.; et al. J. Am. Chem. Soc. 2003, 125, 3192-3193; Speers, A. E.; et al. J. Am. Chem. Soc. 2003, 125, 4686-4687; Link, A. J.; Tirrell, D. A. J. Am. Chem. Soc. 2003, 125, 11164-11165; Deiters, A.; et al. J. Am. Chem. Soc. 2003, 125, 11782-11783). In addition, applications to organic synthesis (Lee, L. V.; et al. J. Am. Chem. Soc. 2003, 125, 9588-9589), drug discovery (Kolb, H. C.; Sharpless, K. B. Drug Disc. Today 2003, 8, 1128-1137; Lewis, W. G.; et al. Angew. Chem. Int. Ed. 2002, 41, 1053-1057), and the functionalization of surfaces (Meng, J.-C.; et al. Angew. Chem. Int. Ed. 2004, 43, 1255-1260; Fazio, F.; et al. J. Am. Chem. Soc. 2002, 124, 14397-14402; Collman, J. P.; et al. Langmuir 2004, ASAP, in press; Lummerstorfer, T.; Hoffmann, H. J. Phys. Chem. B 2004, in press) have also appeared.

Generally, click chemistry encourages reactions that have modular applications that are wide in scope, that have a high chemical yield, that generate inoffensive by-products, that are chemospecific, that require simple reaction conditions, that use readily available starting materials and reagents, that are solvent free or use benign solvents (such as water), that lead to easy product isolation, that have a large thermodynamic driving force to favor a reaction with a single reaction product, and that have a high atom economy. While certain of the general criteria can be subjective in nature, and not all criteria need to be met.

BRIEF SUMMARY OF THE DISCLOSURE

Applicants have developed an amplification system and methodology for IHC and ISH staining that utilizes "click chemistry" to covalently bind reporter molecules to tissue. As will be described further herein, the presently disclosed amplification methodology allows for a reporter moiety to be separated from QMSA or TSA assay conditions, and thus providing advantages over QMSA and TSA protocols.

In one aspect of the present disclosure is a conjugate of Formula (IIa):

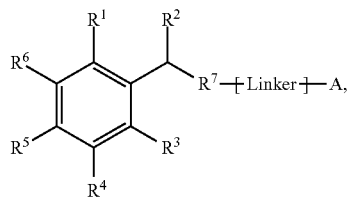

wherein

A is selected from the group consisting of dibenzocyclooctyne, trans-cyclooctene, azide, tetrazine, maleimide, thiol, 1,3-nitrone, aldehyde, ketone, hydrazine, and hydroxylamine;

'Linker' is a branched or unbranched, linear or cyclic, substituted or unsubstituted, saturated or unsaturated, group having between 2 and 80 carbon atoms, and optionally having one or more heteroatoms selected from O, N, or S;

$R^1$ is a group selected from phosphate, amide, nitro, urea, sulfate, methyl, ester, beta-lactam, or a sugar;

$R^2$ is a halide;

$R^3$, $R^5$, and $R^6$ are independently selected from hydrogen or an aliphatic group having between 1 and 4 carbon atoms;

$R^4$ is a hydrogen, an aliphatic group having between 1 and 4 carbon atoms, or the group —CH($R^2$)—$R^7$-[Linker]-A; and $R^7$ is selected from the group consisting of —$(CH_2)_w$NH—, —O$(CH_2)_w$NH—, —N(H)C(O)$(CH_2)_w$NH—, —C(O)N(H)$(CH_2)_w$NH—, —$(CH_2)_w$O—, —O$(CH_2)_w$O—, —O$(CH_2CH_2O)_w$—, —N(H)C(O)$(CH_2)_w$O—, —C(O)N(H)$(CH_2)_w$O—, —C(O)N(H)$(CH_2CH_2O)_w$—, —$(CH_2)_w$S—, —O$(CH_2)_w$S—, —N(H)C(O)$(CH_2)_w$S—, —C(O)N(H)$(CH_2)_w$S—, —$(CH_2)_w$NH—, —C(O)N(H)$CH_2CH_2O)_w$$CH_2CH_2NH$, —C(O)$(CH_2CH_2O)_w$$CH_2CH_2NH$—, —C(O)N(H)$(CH_2)$NHC(O)CH($CH_3$)$(CH_2)_w$NH—, or —N(H)$(CH_2)_w$NH—, where w is an integer ranging from 1 to 12.

In some embodiments, $R^6$, $R^5$, $R^4$, and $R^3$ are each hydrogen. In some embodiments, $R^1$ is a phosphate. In some embodiments, $R^2$ is fluorine. In some embodiments, $R^1$ is a phosphate; $R^2$ is fluorine; and $R^6$, $R^5$, $R^4$, and $R^3$ are each hydrogen.

In some embodiments, 'Linker' has the Formula (Ia):

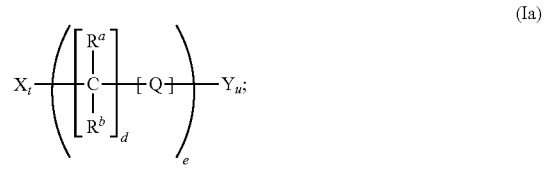

wherein d and e are integers each independently ranging from 2 to 20;

t and u are independently 0 or 1;

Q is a bond, O, S, or N($R^c$)($R^d$);

$R^a$ and $R^b$ are independently H, a $C_1$-$C_4$ alkyl group, F, Cl, or N($R^c$)($R^d$);

$R^c$ and $R^d$ are independently $CH_3$ or H; and

X and Y are independently a branched or unbranched, linear or cyclic, substituted or unsubstituted, saturated or unsaturated group having between 1 and 12 carbon atoms and optionally having one or more O, N, or S heteroatoms.

In some embodiments, $R^a$ and $R^b$ are each hydrogen. In some embodiments, Q is oxygen. In some embodiments, $R^7$ is —C(O)N(H)$(CH_2)_w$NH—. In some embodiments, $R^1$ is a phosphate and $R^7$ is —C(O)N(H)$(CH_2)_w$NH—, and w ranges from 2 to 10. In some embodiments, is fluorine; and $R^6$, $R^5$, $R^4$, and $R^3$ are each hydrogen. In some embodiments, 'Linker' comprises a PEG group.

In another aspect of the present disclosure is a conjugate of Formula (IId):

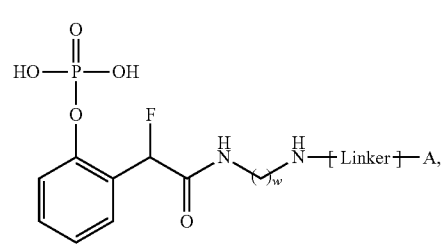

wherein

A is selected from the group consisting of dibenzocyclooctyne, trans-cyclooctene, azide, tetrazine, maleimide, thiol, 1,3-nitrone, aldehyde, ketone, hydrazine, and hydroxylamine;

'Linker' is a branched or unbranched, linear or cyclic, substituted or unsubstituted, saturated or unsaturated, group having between 2 and 80 carbon atoms, and optionally having one or more heteroatoms selected from O, N, or S; and w ranges from 1 to 12.

In some embodiments, 'Linker' has the Formula (Ia):

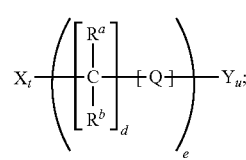

wherein d and e are integers each independently ranging from 2 to 20;

t and u are independently 0 or 1;

Q is a bond, O, S, or $N(R^c)(R^d)$;

$R^a$ and $R^b$ are independently H, a $C_1$-$C_4$ alkyl group, F, Cl, or $N(R^c)(R^d)$;

$R^c$ and $R^d$ are independently $CH_3$ or H; and

X and Y are independently a branched or unbranched, linear or cyclic, substituted or unsubstituted, saturated or unsaturated group having between 1 and 12 carbon atoms and optionally having one or more O, N, or S heteroatoms.

In some embodiments, w ranges from 1 to 8; and wherein $R^a$ and $R^b$ are each hydrogen. In some embodiments, w ranges from 2 to 8, and wherein Q is oxygen. In some embodiments, d and e are independently an integer ranging from 2 to 10. In some embodiments, A is dibenzocyclooctyne. In some embodiments, w ranges from 2 to 6 and wherein the Linker comprises a PEG group. In some embodiments, A is trans-cyclooctene. In some embodiments, ranges from 2 to 6 and wherein the Linker comprises a PEG group. In some embodiments, A is azide. In some embodiments, w ranges from 2 to 6 and wherein the Linker comprises a PEG group. In some embodiments, A is tetrazine. In some embodiments, w ranges from 2 to 6 and wherein the Linker comprises a PEG group.

In another aspect of the present disclosure is a conjugate of Formula (III):

(III), wherein

M is derived from a propionic acid, a cinnamic acid, or a compound of Formula (IIIa), the compound of Formula (IIIa) having the structure:

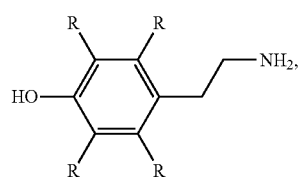

(IIIa)

wherein each R group is independently selected from hydrogen or lower alkyl group (which may be straight chain or branched) having between 1 and 4 carbon atoms;

A is selected from the group consisting of dibenzocyclooctyne, trans-cyclooctene, azide, tetrazine, maleimide, thiol, 1,3-nitrone, aldehyde, ketone, hydrazine, and hydroxylamine; and 'Linker' is a branched or unbranched, linear or cyclic, substituted or unsubstituted, saturated or unsaturated, group having between 2 and 80 carbon atoms, and optionally having one or more heteroatoms selected from O, N, or S;

provided that when each R is hydrogen, A is selected from the group consisting of an azide, a thiol, a 1,3-nitrone, a hydrazine, or a hydroxylamine.

In some embodiments, the 'Linker' has the formula (Ia):

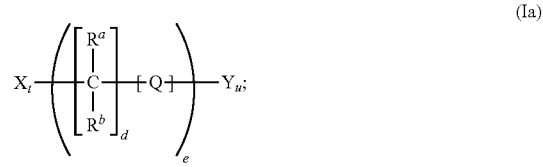

(Ia)

wherein d and e are integers each independently ranging from 2 to 20;

t and u are independently 0 or 1;

Q is a bond, O, S, or $N(R^c)(R^d)$;

$R^a$ and $R^b$ are independently H, a $C_1$-$C_4$ alkyl group, F, Cl, or $N(R^c)(R^d)$;

$R^c$ and $R^d$ are independently $CH_3$ or H; and

X and Y are independently a branched or unbranched, linear or cyclic, substituted or unsubstituted, saturated or unsaturated group having between 1 and 12 carbon atoms and optionally having one or more O, N, or S heteroatoms.

In some embodiments, $R^a$ and $R^b$ are each hydrogen. In some embodiments, Q is oxygen. In some embodiments, $R^a$ and $R^b$ are each hydrogen, Q is oxygen, and e ranges from 2 to 10.

In another aspect of the present disclosure is a conjugate of Formula (Id):

(Id), wherein

A is selected from the group consisting of dibenzocyclooctyne, trans-cyclooctene, azide, tetrazine, maleimide, thiol, 1,3-nitrone, aldehyde, ketone, hydrazine, and hydroxylamine;

'Linker' is a branched or unbranched, linear or cyclic, substituted or unsubstituted, saturated or unsaturated, group having between 2 and 80 carbon atoms, and optionally having one or more heteroatoms selected from O, N, or S; and 'Tissue Reactive Precursor Moiety' is derived from a compound selected from the group consisting of:

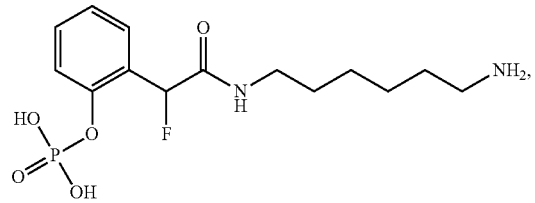

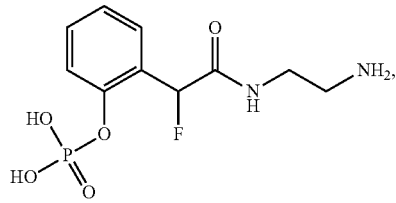

-continued

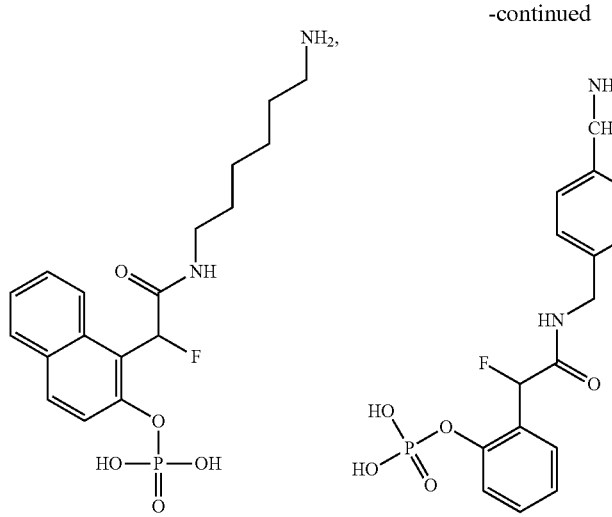
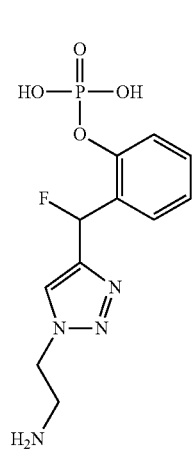
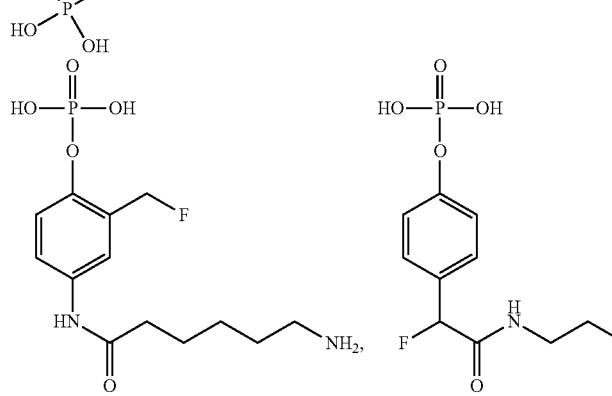
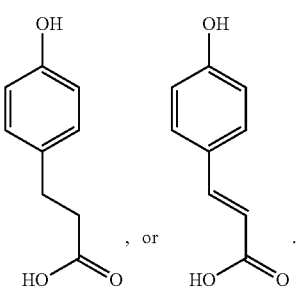

In some embodiments, 'Linker' has the formula (Ia):

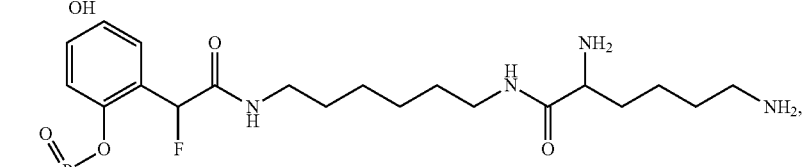

wherein
d and e are integers each independently ranging from 2 to 20;
t and u are independently 0 or 1;
Q is a bond, O, S, or $N(R^c)(R^d)$;
$R^a$ and $R^b$ are independently H, a $C_1$-$C_4$ alkyl group, F, Cl, or $N(R^c)(R^d)$;
$R^c$ and $R^d$ are independently $CH_3$ or H; and
X and Y are independently a branched or unbranched, linear or cyclic, substituted or unsubstituted, saturated or unsaturated group having between 1 and 12 carbon atoms and optionally having one or more O, N, or S heteroatoms.

In some embodiments, $R^a$ and $R^b$ are each hydrogen. In some embodiments, Q is oxygen. In some embodiments, $R^a$ and $R^b$ are each hydrogen, Q is oxygen, and e ranges from 2 to 10.

In another aspect of the present disclosure is a conjugate of Formula (IV):

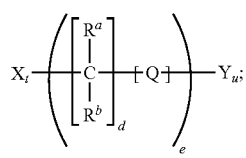  (IV), wherein

A is selected from the group consisting of dibenzocyclooctyne, trans-cyclooctene, azide, tetrazine, maleimide, thiol, 1,3-nitrone, aldehyde, ketone, hydrazine, and hydroxylamine;

'Linker' is a branched or unbranched, linear or cyclic, substituted or unsubstituted, saturated or unsaturated, group having between 2 and 80 carbon atoms, and optionally having one or more heteroatoms selected from O, N, or S; and Z is selected from the group consisting of a chromophore, a fluorophore, an enzyme, a hapten, and a chelator.

In some embodiments, Z is a chromophore selected from the group consisting of tetramethylrhodamine, Cyanine 5, and Dabsyl. In some embodiments, Z is selected from the group consisting of:

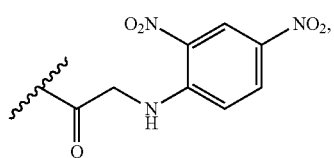

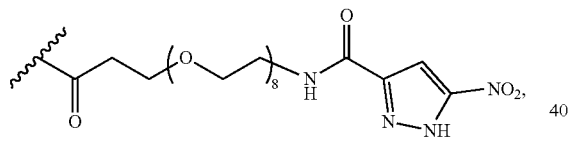

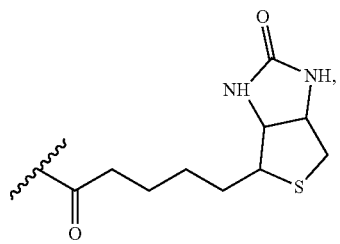

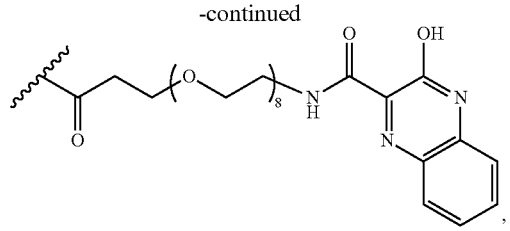

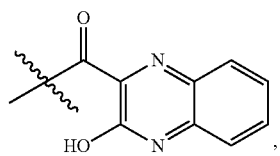

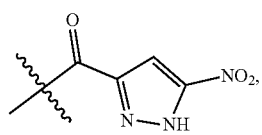

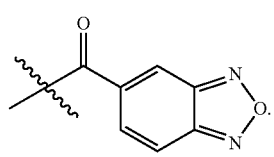

In some embodiments, the conjugate has the structure of Formula (IVa):

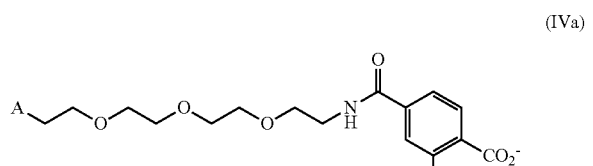

(IVa)

In some embodiments, the conjugate has the structure of Formula (IVb):

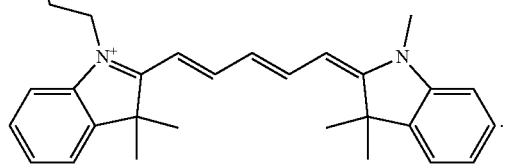

(IVb)

In some embodiments, the conjugate has the structure of Formula (IVc):
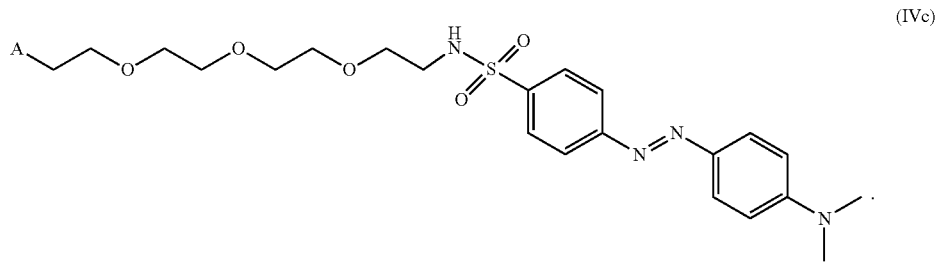
(IVc)
In some embodiments, the conjugate has the structure of Formula (IVd):
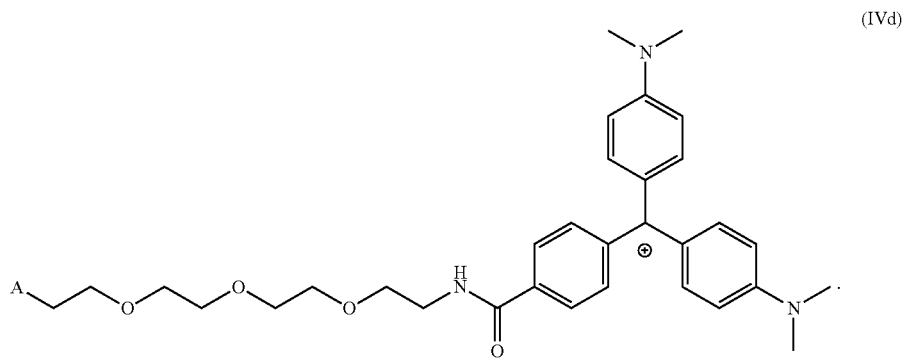
(IVd)
In some embodiments, the conjugate is:
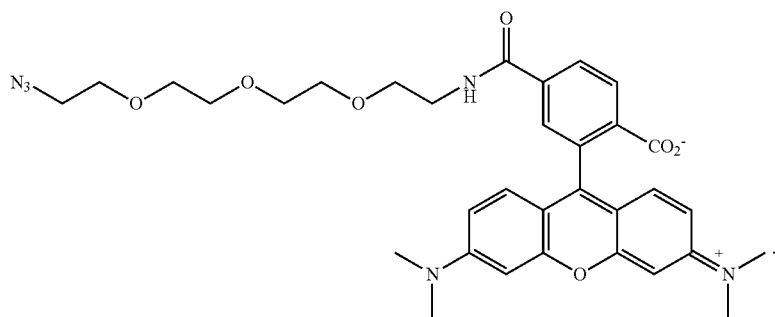
In some embodiments, the conjugate is:
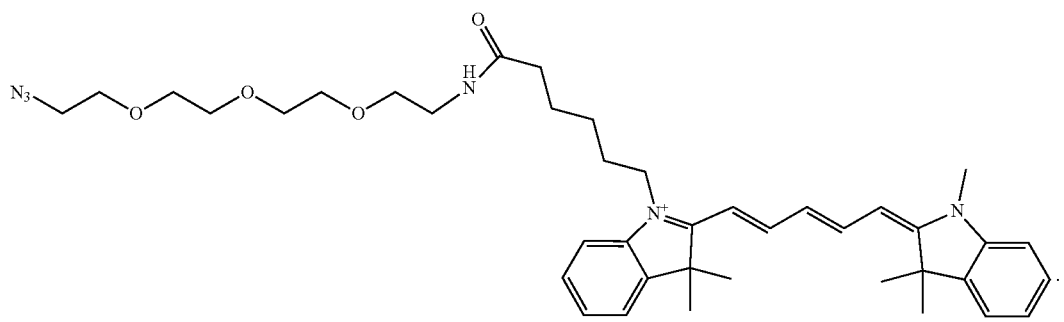 [SMILES: CN1/C(=C/C=C/C=C/C2=[N+](CCCCCC(=O)NCCOCCOCCOCCN=[N+]=[N-])c3ccccc3C2(C)C)C(C)(C)c2ccccc21]

In some embodiments, the conjugate is:
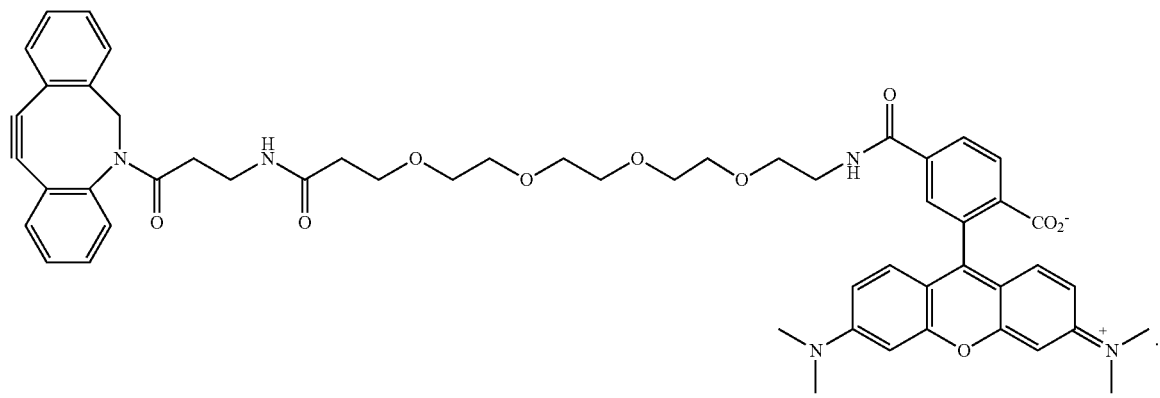
In some embodiments, the conjugate is:
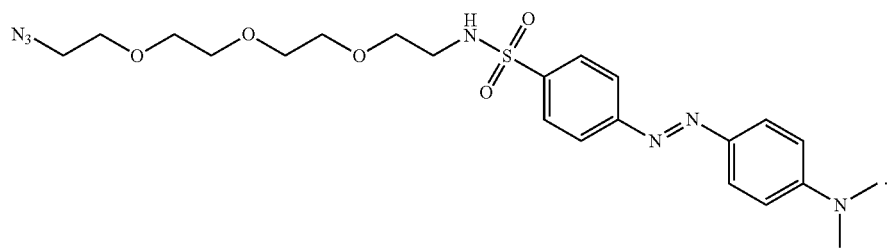 [SMILES: CN(C)c1ccc(/N=N/c2ccc(S(=O)(=O)NCCOCCOCCOCCN=[N+]=[N-])cc2)cc1]
In some embodiments, the conjugate is:
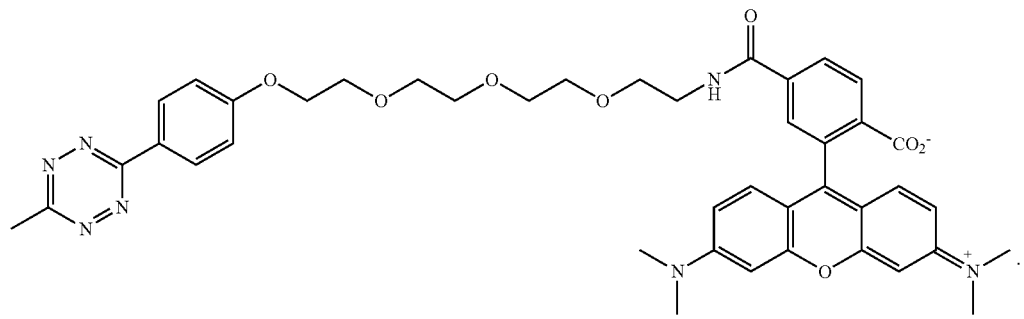
In some embodiments, the conjugate is:
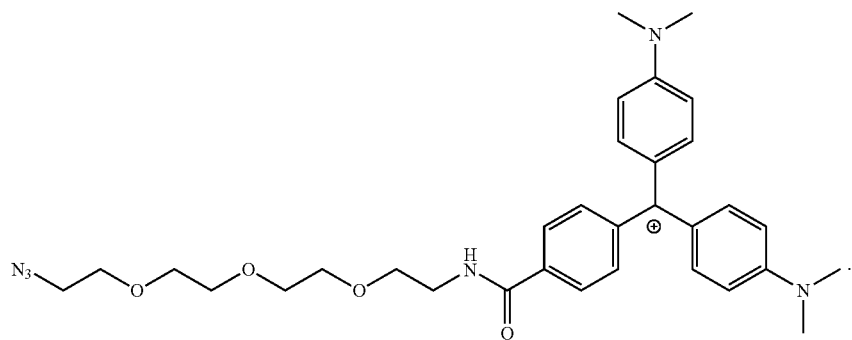 [SMILES: CN(C)c1ccc(C(c2ccc(C(=O)NCCOCCOCCOCCN=[N+]=[N-])cc2)c2ccc(N(C)C)cc2)cc1]

In some embodiments, the conjugate is:

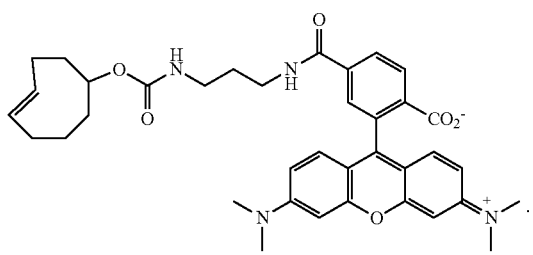

In some embodiments, the conjugate is:

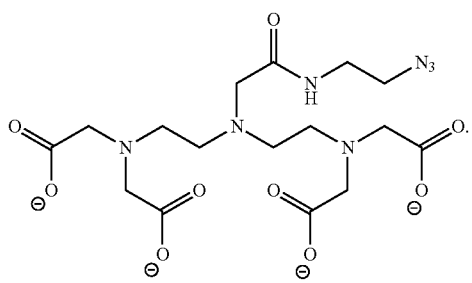 [SMILES: [N-]=[N+]=NCCNC(=O)CN(CCN(CC(=O)[O-])CC(=O)[O-])CCN(CC(=O)[O-])CC(=O)[O-]]

In another aspect of the present disclosure is a method of detecting a first target in a biological sample, comprising: contacting the biological sample with a first detection probe specific to the first target to form a first detection probe-target complex; contacting the biological sample with a first labeling conjugate specific for the first detection probe, the first labeling conjugate comprising a first enzyme such that the first-detection probe-target complex becomes labeled with the first enzyme; contacting the biological sample with a first member of a first pair of click conjugates, the first member of the first pair of click conjugates comprising a tissue reactive moiety, wherein the first enzyme converts the first member of the first pair of click conjugates to a first reactive intermediate which covalently bonds to the biological sample proximally to or directly on the first target to form a first immobilized tissue-click conjugate complex; contacting the biological sample with a second member of a first pair of click conjugates, the second member of the first pair of click conjugates comprising a second reactive moiety capable of reacting with a first reactive moiety of the first immobilized tissue-click conjugate complex such that a covalent bond is formed between the first immobilized tissue-click conjugate complex and the second member of the first pair of click conjugates to form a first tissue-click conjugate adduct; and detecting signals from a first reporter moiety of first tissue-click conjugate adduct.

In some embodiments, the second member of the first pair of click conjugates comprises at least one chromophore. In some embodiments, the first member of the first pair of click conjugates comprises a quinone methide precursor moiety; and wherein the second member of the first pair of click conjugates comprises a chromophore. In some embodiments, first member of the first pair of click conjugates comprises a tyramide moiety; and wherein the second member of the first pair of click conjugates comprises a chromophore. In some embodiments, the first detection probe is a primary antibody, and wherein the first labeling conjugate comprises an anti-antibody antibody. In some embodiments, wherein the first enzyme is selected from the group consisting of phosphatase, phosphodiesterase, esterase, lipase, amidase, protease, nitroreductase, urease, sulfatase, cytochrome P450, alpha-glucosidase, beta-glucosidase, beta-lactamase, alpha-glucoronidase, beta-glucoronidase, alpha-5-galactosidase, neuraminidase, beta-galactosidase, alpha-lactase and beta-lactase.

In some embodiments, the method further comprises detecting a second target in the biological sample, wherein the second target is detected by contacting the biological sample with a second detection probe specific to the second target to form a second detection probe-target complex; contacting the biological sample with a second labeling conjugate specific for the second detection probe, the second labeling conjugate comprising a second enzyme such that the second detection probe-target complex becomes labeled with the second enzyme; contacting the biological sample with a first member of a second pair of click conjugates, the first member of the second pair of click conjugates comprising a tissue reactive moiety, wherein the second enzyme converts the first member of the second pair of click conjugates to a second reactive intermediate which covalently bonds to the biological sample proximally to or directly on the second target to form a second immobilized tissue-click conjugate complex; contacting the biological sample with a second member of a second pair of click conjugates, the second member of the second pair of click conjugates comprising a second reactive moiety capable of reacting with a first reactive moiety of the second immobilized tissue-click conjugate complex such that a covalent bond is formed between second immobilized tissue-click conjugate complex and the second member of the second pair of click conjugates; and detecting signals from a second reporter moiety of the second tissue-click conjugate adduct, wherein the second reporter moiety is different than the first reporter moiety.

In some embodiments, the second member of the second pair of click conjugates comprises at least one chromophore. In some embodiments, the first member of the second pair of click conjugates comprises a quinone methide precursor moiety; and wherein the second member of the second pair of click conjugates comprises a chromophore. In some embodiments, the first member of the second pair of click conjugates comprises a tyramide moiety; and wherein the second member of the second pair of click conjugates comprises a chromophore. In some embodiments, the second detection probe is a primary antibody, and wherein second first labeling conjugate comprises an anti-antibody antibody. In some embodiments, the second enzyme is selected from the group consisting of phosphatase, phosphodiesterase, esterase, lipase, amidase, protease, nitroreductase, urease, sulfatase, cytochrome P450, alpha-glucosidase, beta-glucosidase, beta-lactamase, alpha-glucoronidase, beta-glucoronidase, alpha-5-galactosidase, beta-galactosidase, alpha-lactase and beta-lactase.

In another aspect of the present disclosure is an immobilized click-conjugate covalently bonded to a tissue sample, the immobilized click-conjugate comprising a first reactive functional group selected from the group consisting of dibenzocyclooctyne, trans-cyclooctene, azide, tetrazine, maleimide, thiol, 1,3-nitrone, aldehyde, ketone, hydrazine, and hydroxylamine. In some embodiments, the click-conjugate is bonded to the tissue through a tyrosine residue or a nucleophilic species within or on the surface of the tissue sample.

In another aspect of the present disclosure is a detectable tissue-click adduct complex formed by reacting an immobilized click-conjugate, such as noted above, with a conjugate of Formula (IV):

$$A\text{---[Linker]---}Z \tag{IV}$$

wherein

A is selected from the group consisting of dibenzocyclooctyne, trans-cyclooctene, azide, tetrazine, maleimide, thiol, 1,3-nitrone, aldehyde, ketone, hydrazine, and hydroxylamine;

'Linker' is a branched or unbranched, linear or cyclic, substituted or unsubstituted, saturated or unsaturated, group having between 2 and 80 carbon atoms, and optionally having one or more heteroatoms selected from O, N, or S; and Z is selected from the group consisting of a chromophore, a fluorophore, an enzyme, a hapten, and a chelator; and wherein the conjugate of Formula (IV) comprises an A group capable of reacting with the first reactive functional group of the immobilized click-conjugate.

In some embodiments, Z is at least one chromophore. In some embodiments, the first reactive functional group is dibenzocyclooctyne and where A of Formula (IV) is selected from the group consisting of an azide or a 1,3-nitrone. In some embodiments, the first reactive functional group is trans-cyclooctene and where A of Formula (IV) is a tetrazine. In some embodiments, the first reactive functional group is an azide and where A of Formula (IV) is a dibenzocyclooctyne. In some embodiments, Z is a chelator, and wherein a lanthanide is introduced to the formed detectable tissue-click adduct complex.

Applicants have discovered that the click conjugates disclosed herein are suitable for use in biological assays and that their use improves upon limitations of TSA and QMSA. For example, and without wishing to be bound by any particular theory, Applicants have found that the staining quality resulting from QMSA is highly dependent on the solubility of the quinone methide-reporter conjugates. For example, very hydrophobic QMSA conjugates tend to stain discretely but with low signal intensity, while very hydrophilic QMSA conjugates tend to stain with high signal intensity but also an undesirable level of diffusion. To solve this problem, each quinone methide-reporter conjugate must be synthesized differently to optimize the diffusion and signal intensity. For example, a very hydrophobic reporter may require an amphiphilic PEG linker, while a hydrophilic reporter may require a hydrophobic aliphatic linker. Thus, QMSA may be tedious and, in some circumstances, conjugates have not been able to be optimized with respect to limiting diffusion to a desirable level. Applicants have discovered that amplification processes based on QMSA but utilizing the click conjugates herein improves upon QMSA.

Likewise, with regard to TSA, and again without wishing to be bound by any particular theory, Applicants believe that many fluorophores and chromophores are sensitive to oxidation, resulting in irreversible decomposition and loss of color and fluorescence. Applicants also believe that the oxidative conditions required for the TSA assay can accelerate the oxidation of some dyes (i.e. cyanine dyes), rendering them poor reporters for TSA (low signal intensity despite high substrate concentrations). Applicants have also shown that the hydrophobicity of tyramine coupled with the hydrophobicity of many fluorophores and chromophores may result in tyramide conjugates that are not soluble in the required aqueous IHC and ISH reaction media. For nearly all conjugates, amphiphilic PEG linkers are required to solubilize the conjugates. However, in some cases, the PEG linkers are not enough to overcome the hydrophobicity, leaving some desirable reporters (i.e. dabsyl) unusable. As a result of these two limitations, two desirable color spaces, blue (cy5) and yellow (dabsyl) are currently not accessible using TSA. Applicants have discovered that amplification processes based on TSA but utilizing the click conjugates herein improves upon TSA.

A further limitation common to both QMSA and TSA is the inability to amplify over signal beyond a certain saturation point. On tissue there exist a finite number of these reactive sites for QMSA and TSA reactive intermediate to bind to. Once those reactive sites are exhausted, the signal intensity saturates. Applicants have discovered that amplification processes utilizing the click conjugates and methodology disclosed herein are able to increase overall signal, thus allowing for visualization of markers of low abundance.

Applicants have surprisingly discovered that amplification utilizing pairs of click conjugates as described herein (i) "shelters" the reporter molecule (here, a component part of one member of a pair of click conjugates) from potentially unfavorable conditions (i.e. oxidatively unstable chromophores in the case of TSA), allowing one the use of a wider range of reporters; (ii) solves the aqueous solubility problems associated with some tyramide conjugates for TSA (i.e. dabsyl); (iii) for QMSA, the solubility of only a few QM-"click" conjugates are needed to be "tuned" rather than the entire library of fluorophores, chromophores, and haptens. Applicants believe that these properties, taken together, provide a simplified amplification methodology for both QMSA and TSA, the ability to add additional desirable color spaces to the TSA color palette, and overall enhancements in staining intensity. These and other aspects will be further described herein.

BRIEF DESCRIPTION OF THE FIGURES

The patent or application file contains at least one drawing executed in color. Copies of this patent or patent application publication with color drawings will be provided to the Office upon request and the payment of the necessary fee.

FIG. 9A depicts a Tyramide-DBCO conjugate reacted with a click conjugate of Formula (IV) where the click conjugate of Formula (IV) was coupled to a Cy5 chromogen.

FIG. 9B depicts a Tyramide-DBCO conjugate reacted with a click conjugate of Formula (IV) where the click conjugate of Formula (IV) was coupled to Dabsyl chromogen.

FIG. 9C depicts a Tyramide-DBCO conjugate reacted with a click conjugate of Formula (IV) where the click conjugate of Formula (IV) comprised both a TAMRA chromogen and a Dabcyl chromogen, where the two chromogens were coupled via a lysine scaffold.

FIG. 9D depicts a Tyramide-DBCO conjugate reacted with a click conjugate of Formula (IV) where the click conjugate of Formula (IV) comprised a coupled TAMRA chromogen.

FIG. 9E depicts a Tyramide-DBCO conjugate being reacted with a click conjugate coupled to a chromogen.

FIGS. 12A-12D comparatively illustrate the differences in staining intensities when using a click conjugate comprising a single chromophore and a click conjugate comprising a plurality of chromophores.

FIG. 12A illustrates a click conjugate having a single chromophore.

FIG. 12B illustrates a click conjugate having a plurality of chromophores.

FIG. 12C illustrates staining intensity when using a click conjugate having a single chromophore.

FIG. 12D illustrates staining intensity when using a click conjugate having a plurality of chromophores.

FIG. 13A illustrates staining at a concentration of 35 µg/mL.

FIG. 13B illustrates staining at a concentration of 3.5 µg/mL.

FIG. 13C illustrates staining at a concentration of 0.7 µg/mL.

DETAILED DESCRIPTION

Figure 1A:
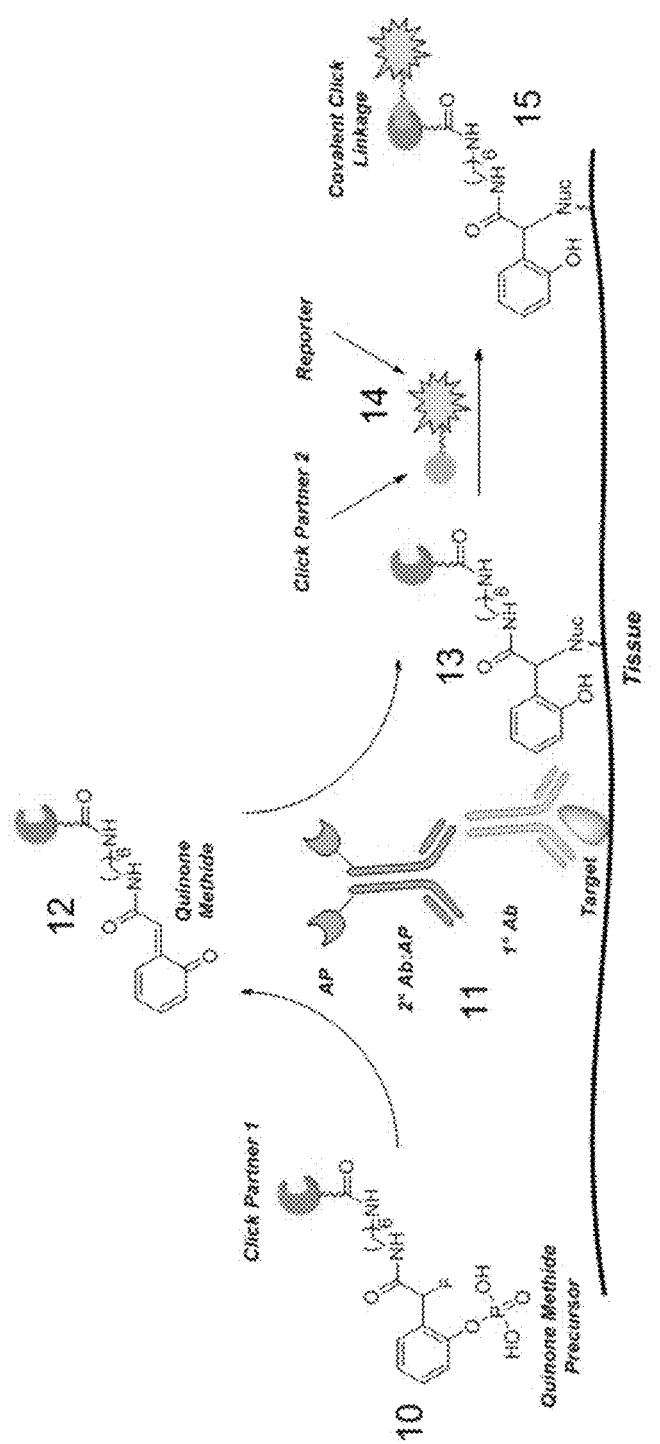
FIG. 1A sets forth a reaction scheme illustrating the reaction between a click conjugate comprising a quinone methide precursor moiety and a tissue-bound enzyme; followed by reaction between the resulting tissue-click conjugate complex and a second click conjugate to form a tissue-click conjugate adduct.

In general, the present disclosure is directed to click conjugates, as well as methods of employing click conjugates for detecting one or more targets present in a biological sample. In some embodiments, the click conjugates (or kits comprising one or more click conjugates) are used in a multiplex assay to detect multiple targets within a tissue sample, either simultaneously or sequentially. These and other aspects of the present disclosure are detailed more fully herein.

Definitions

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein, alkaline phosphatase (AP) is an enzyme that removes (by hydrolysis) and transfers phosphate group organic esters by breaking the phosphate-oxygen bond, and temporarily forming an intermediate enzyme-substrate bond. For example, AP hydrolyzes naphthol phosphate esters (a substrate) to phenolic compounds and phosphates. The phenols couple to colorless diazonium salts (chromogen) to produce insoluble, colored azo dyes.

As used herein, the term "antibody," occasionally abbreviated "Ab," refers to immunoglobulins or immunoglobulin-like molecules, including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments that specifically bind to a molecule of interest (or a group of highly similar molecules of interest) to the substantial exclusion of binding to other molecules. Antibody further refers to a polypeptide ligand comprising at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art.

As used herein, the phrase "antibody conjugates," refers to those antibodies conjugated (either directly or indirectly) to one or more labels, where the antibody conjugate is specific to a particular target and where the label is capable of being detected (directly or indirectly), such as with a secondary antibody (an anti-label antibody). For example, an antibody conjugate may be coupled to a hapten such as through a polymeric linker and/or spacer, and the antibody conjugate, by means of the hapten, may be indirectly detected. As an alternative example, an antibody conjugate may be coupled to a fluorophore, such as through a polymeric linker and/or spacer, and the antibody conjugate may be detected directly. Antibody conjugates are described further in US Publication No. 2014/0147906 and U.S. Pat. Nos. 8,658,389; 8,686,122; 8,618,265; 8,846,320; and 8,445,191. By way of a further example, the term "antibody conjugates" includes those antibodies conjugated to an enzyme, e.g. HRP or AP.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins.

As used herein, the term a "biological sample" can be any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a nuclear extract. In certain examples, a sample is a quality control sample, such as one of the disclosed cell pellet section samples. In other examples, a sample is a test sample. Samples can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Samples can include multiple targets that can be specifically bound by one or more detection probes.

As used herein, the term "chromophore" refers to a molecule or a part of a molecule responsible for its color. Color arises when a molecule absorbs certain wavelengths of visible light and transmits or reflects others. A molecule having an energy difference between two different molecular orbitals falling within the range of the visible spectrum may absorb visible light and thus be aptly characterized as a chromophore. Visible light incident on a chromophore may be absorbed thus exciting an electron from a ground state molecular orbital into an excited state molecular orbital.

As used herein, the term "conjugate" refers to two or more molecules or moieties (including macromolecules or supramolecular molecules) that are covalently linked into a larger construct. In some embodiments, a conjugate includes one or more biomolecules (such as peptides, proteins, enzymes, sugars, polysaccharides, lipids, glycoproteins, and lipoproteins) covalently linked to one or more other molecules moieties.

As used herein, the terms "couple" or "coupling" refers to the joining, bonding (e.g. covalent bonding), or linking of one molecule or atom to another molecule or atom.

As used herein, "haptens" are small molecules that can combine specifically with an antibody, but typically are substantially incapable of being immunogenic except in combination with a carrier molecule. In some embodiments embodiments, haptens include, but are not limited to, pyrazoles (e.g. nitropyrazoles); nitrophenyl compounds; benzofurazans; triterpenes; ureas (e.g. phenyl ureas); thioureas (e.g. phenyl thioureas); rotenone and rotenone derivatives;

oxazole (e.g. oxazole sulfonamides); thiazoles (e.g. thiazole sulfonamides); coumarin and coumarin derivatives; and cyclolignans. Additional non-limiting examples of haptens include thiazoles; nitroaryls; benzofurans; triperpenes; and cyclolignans. Specific examples of haptens include di-nitrophenyl, biotin, digoxigenin, and fluorescein, and any derivatives or analogs thereof. Other haptens are described in U.S. Pat. Nos. 8,846,320; 8,618,265; 7,695,929; 8,481,270; and 9,017,954, the disclosures of which are incorporated herein by reference in their entirety. The haptens themselves may be suitable for direct detection, i.e. they may give off a suitable signal for detection.

As used herein, horseradish peroxidase (HRP) is an enzyme that can be conjugated to a labeled molecule. It produces a colored, fluorimetric, or luminescent derivative of the labeled molecule when incubated with a proper substrate, allowing it to be detected and quantified. HRP acts in the presence of an electron donor to first form an enzyme substrate complex and then subsequently acts to oxidize an electronic donor. For example, HRP may act on 3,3'-diaminobenzidinetrahydrochloride (DAB) to produce a detectable color. HRP may also act upon a labeled tyramide conjugate, or tyramide like reactive conjugates (i.e. ferulate, coumaric, caffeic, cinnamate, dopamine, etc.), to deposit a colored or fluorescent or colorless reporter moiety for tyramide signal amplification (TSA).

As used herein, the terms "multiplex," "multiplexed," or "multiplexing" refer to detecting multiple targets in a sample concurrently, substantially simultaneously, or sequentially. Multiplexing can include identifying and/or quantifying multiple distinct nucleic acids (e.g., DNA, RNA, mRNA, miRNA) and polypeptides (e.g., proteins) both individually and in any and all combinations.

As used herein, the term "primary antibody" refers to an antibody which binds specifically to the target protein antigen in a tissue sample. A primary antibody is generally the first antibody used in an immunohistochemical procedure.

As used herein, a "quinone methide" is a quinone analog where one of the carbonyl oxygens on the corresponding quinone is replaced by a methylene group ($CH_2$) to form an alkene.

As used herein, the term "secondary antibody" herein refers to an antibody which binds specifically to a primary antibody, thereby forming a bridge between the primary antibody and a subsequent reagent (e.g. a label, an enzyme, etc.), if any. The secondary antibody is generally the second antibody used in an immunohistochemical procedure.

As used herein, the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least $10^{-3}$ M greater, $10^{-4}$ M greater or $10^{-5}$ M greater than a binding constant for either of the two members of the binding pair with other molecules in a biological sample). Particular examples of specific binding moieties include specific binding proteins (for example, antibodies, lectins, avidins such as streptavidins, and protein A). Specific binding moieties can also include the molecules (or portions thereof) that are specifically bound by such specific binding proteins.

As used herein, the term "target" refers to any molecule for which the presence, location and/or concentration is or can be determined. Examples of target molecules include proteins, nucleic acid sequences, and haptens, such as haptens covalently bonded to proteins. Target molecules are typically detected using one or more conjugates of a specific binding molecule and a detectable label.

"Click" Conjugates

The present disclosure provides two general subsets of click conjugates. A first subset of click conjugates comprises a tissue reactive moiety coupled to a reactive functional group through an optional linker. In some embodiments, this first subset of click conjugates is used as first members of pairs of click conjugates. A second subset of click conjugates comprises one or more reporter moieties coupled to a reactive functional group through an optional linker. In some embodiments, this second subset of click conjugates are used as second members of pairs of click conjugates. It will be appreciated that the different subsets of click conjugates disclosed herein may serve as modular "building blocks" such that when any two conjugates having appropriate reactive function groups are combined (a "pair of click conjugates"), they may undergo a reaction and form a covalent bond, thereby coupling the two conjugates to form a "click adduct" having the desired structure or component parts.

As will be described further herein, the click adducts formed may serve as species suitable for detecting targets in a biological assay. Without wishing to be bound by any particular theory, it is believed that the click conjugates disclosed herein are stable in aqueous media, and thus suitable for use in certain biological assays, including in IHC and ISH. Moreover, it is believed that the click conjugates have a large thermodynamic driving force that favors a fast reaction providing a single product. In addition, the solubility of any of the click conjugates described herein may be "tuned" to meet the requirements of any particular assay, and such "tuning" may be accomplished by, for example, introducing a water soluble linker or water soluble linker components into the conjugates. Moreover, the reactions comprising the click conjugates described herein may be carried out in a wide variety of buffers and thus at a wide variety of pHs, allowing the skilled artisan to choose the ideal conditions for reporter stability.

In one aspect of the present disclosure are click conjugates of Formula (I):

  (I), wherein A is a reactive functional group, "Linker" is an optional linking group, B is selected from a "tissue reactive moiety" or a reporter moiety.

As used herein, the term "tissue reactive" refers to a moiety that is capable of reacting with an enzyme. As such, when a click conjugate comprising a tissue reactive moiety is reacted with an appropriate enzyme, the tissue reactive moiety portion of the click conjugate undergoes a structural, conformational, and/or electronic change, thereby providing a tissue reactive species (an intermediate, including radical intermediates) suitable for bonding directly or indirectly onto (or, to the extent possible, within) a biological sample. For example, where the tissue reactive moiety is a tyramide or derivative thereof, when the tyramide reacts with an appropriate enzyme (e.g. an HRP), a tyramide radical species (an intermediate) is formed. This highly reactive tyramide radical species is capable of bonding to tyrosine residues in biological samples. In a similar manner, a quinone methide precursory moiety, upon reaction with an appropriate enzyme (e.g. AP), is converted to a quinone methide, which is believed to be highly reactive with nucleophiles in a biological sample. The role of the tissue reactive moiety portion of any click conjugate, its interaction with a suitable enzyme, and the formation of an immobilized tissue-click conjugate complex is described further herein.

In some embodiments, A is selected from the group consisting of dibenzocyclooctyne ("DBCO"), trans-cyclooctene ("TCO"), azide, tetrazine, maleimide, thiol, 1,3-nitrone, aldehyde, ketone, hydrazine, and hydroxylamine. In some embodiments, A is selected from a group capable of undergoing a photo-initiated reaction.

The click conjugates optionally comprise a "Linker." In some embodiments, a 'Linker' is a branched or unbranched, linear or cyclic, substituted or unsubstituted, saturated or unsaturated, group having between 2 and 80 carbon atoms, and optionally having one or more heteroatoms selected from O, N, or S. In some embodiments, the "Linker" comprises one or more groups selected from amino, alkylamino, oxygen, sulfur, sulfoxide, sulfonyl, carbonyl, and imine groups. The linker chain may also comprise an aromatic group, including heteroaromatic groups, wherein the heteroaromatic groups comprise 1 to 4 heteroatoms selected from O, N, or S.

In some embodiments, the 'Linker' has the structure depicted in Formula (Ia):

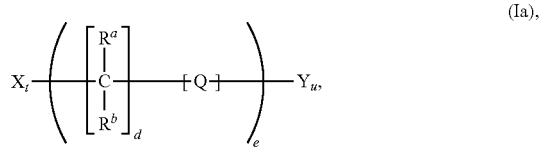

wherein d and e are integers each independently ranging from 2 to 20; t and u are independently 0 or 1; Q is a bond, O, S, or $N(R^c)(R^d)$; $R^a$ and $R^b$ are independently H, a $C_1$-$C_4$ alkyl group, F, Cl, or $N(R^c)(R^d)$; $R^c$ and $R^d$ are independently $CH_3$ or H; and X and Y are independently a branched or unbranched, linear or cyclic, substituted or unsubstituted, saturated or unsaturated group having between 1 and 12 carbon atoms and optionally having one or more O, N, or S heteroatoms. In some embodiments, X and Y include carbonyl groups, amide groups, ester groups, ester groups, substituted or unsubstituted aryl groups, or any combination thereof. In other embodiments, d and e are integers ranging from 2 to 10. In yet other embodiments, d and e are integers ranging from 2 to 6.

In some embodiments, the "Linker" has the structure depicted in Formula (Ib):

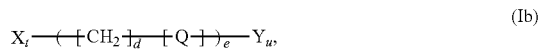

wherein
d and e are integers each independently ranging from 2 to 20;
t and u are independently either 0 or 1;
Q is a bond, O, S, or $N(R^c)(R^d)$;
$R^c$ and $R^d$ are independently $CH_3$ or H; and
X and Y are independently a branched or unbranched, linear or cyclic, substituted or unsubstituted, saturated or unsaturated group having between 1 and 12 carbon atoms and optionally having one or more O, N, or S heteroatoms.

In some embodiments, X and Y are independently a branched or unbranched, linear or cyclic, substituted or unsubstituted, saturated or unsaturated group having between 2 and 8 carbon atoms and optionally having one or more O, N, or S heteroatoms.

In some embodiments, the "Linker" has the structure depicted in Formula (Ic):

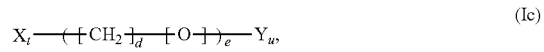

wherein
d and e are integers each independently ranging from 2 to 20;
t and u are independently either 0 or 1; and
X and Y are independently a branched or unbranched, linear or cyclic, substituted or unsubstituted, saturated or unsaturated group having between 1 and 12 carbon atoms and optionally having one or more O, N, or S heteroatoms.

In other embodiments, d and e are integers ranging from 2 to 10. In yet other embodiments, d and e are integers ranging from 2 to 6.

The alkylene oxide based "Linker" of Formulas (Ia), (Ib), and (Ic), are represented herein by reference to glycols, such as ethylene glycols. In some embodiments, the incorporation of such alkylene oxide linkers is believed to increase the hydrophilicity of the click conjugate. A person of ordinary skill in the art will appreciate that, as the number alkylene oxide repeat units in the linker increases, the hydrophilicity of the conjugate also may increase. Additional heterobifunctional polyalkyleneglycol spacers useful for practicing certain disclosed embodiments of the present disclosure are described in assignee's co-pending applications, including "Nanoparticle Conjugates," U.S. patent application Ser. No. 11/413,778, filed Apr. 28, 2006; "Antibody Conjugates," U.S. application Ser. No. 11/413,415, filed Apr. 27, 2006; and "Molecular Conjugate," U.S. Provisional Patent Application No. 60/739,794, filed Nov. 23, 2005; all of which applications are incorporated herein by reference.

Tissue Reactive Precursor Moiety "Click" Conjugates

In some embodiments, the click conjugates of the present disclosure have the structure of Formula (Id):

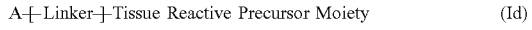

wherein the "Tissue Reactive Precursor Moiety" is (i) a tyramide or a derivative or analog thereof, or (ii) a quinone methide precursor; and where A and Linker are as defined above. Exemplary quinone methide precursor derivatives suitable for incorporation into the disclosed click conjugates of Formula (I) include those recited in PCT/EP2015/053556, entitled "Quinone Methide Analog Signal Amplification," having an international filing date of Feb. 20, 2015, the disclosure of which is hereby incorporated by reference herein in its entirety.

Quinone Methide "Click" Conjugates

In some embodiments, the compounds have Formula (II):

wherein
A is as defined above;
"Linker" is an optional linking group as defined above; and
U is a quinone methide precursor, derivative, or analog thereof.

In some embodiments, the compounds of Formula (II) are a first member of a pair of click conjugates.

As used herein, "quinone methide precursors" are a class of conjugated compounds that, when reacted with an appropriate enzyme (e.g. AP), are converted to a highly reactive quinone methide. As noted above, quinone methide precursors and their conversion to quinone methides are described in PCT/EP2015/053556, the disclosure of which is hereby incorporated by reference herein in its entirety.

In some embodiments, the quinone methide precursor portion of the conjugate of Formula (II) is derived from one of the following quinone methide precursor derivatives:

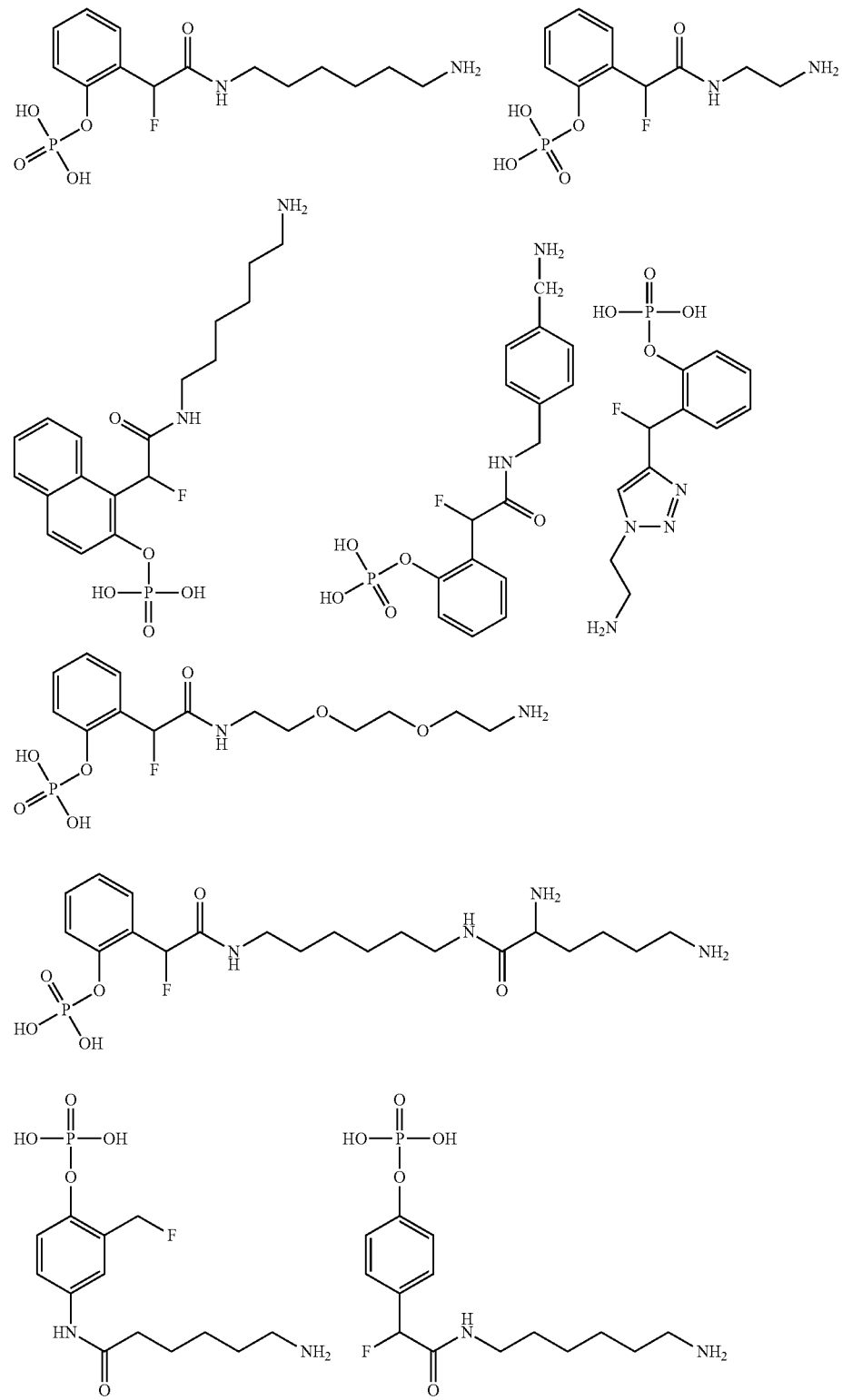

In some embodiments, the conjugates of Formula (II) have the structure of Formula (IIa):

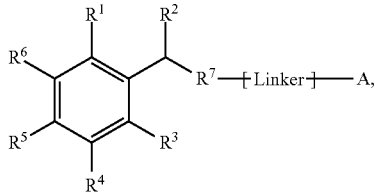
(IIa)

wherein "Linker" and A are as defined herein, $R^1$ is a group selected from phosphate, amide, nitro, urea, sulfate, methyl, ester, beta-lactam, or a sugar;

$R^2$ is a halide;

$R^3$, $R^5$, and $R^6$ are independently selected from hydrogen or an aliphatic group having between 1 and 4 carbon atoms;

$R^4$ is a hydrogen, an aliphatic group having between 1 and 4 carbon atoms, or the group —CH($R^2$)—$R^7$-[Linker]-A;

$R^7$ is —(CH$_2$)$_w$NH—, —O(CH$_2$)$_w$NH—, —N(H)C(O)(CH$_2$)$_w$NH—, —C(O)N(H)(CH$_2$)$_w$NH—, —(CH$_2$)$_w$O—, —O(CH$_2$)$_w$O—, —O(CH$_2$CH$_2$O)$_w$—, —N(H)C(O)(CH$_2$)$_w$O—, —C(O)N(H)(CH$_2$)$_w$O—, —C(O)N(H)(CH$_2$CH$_2$O)$_w$—, —(CH$_2$)$_w$S—, —O(CH$_2$)$_w$S—, —N(H)C(O)(CH$_2$)$_w$S—, —C(O)N(H)(CH$_2$)$_w$S—, —(CH$_2$)$_w$NH—, —C(O)N(H)(CH$_2$CH$_2$O)$_w$CH$_2$CH$_2$NH, —C(O)(CH$_2$CH$_2$O)$_w$CH$_2$CH$_2$NH—, —C(O)N(H)(CH$_2$)NHC(O)CH(CH$_3$)(CH$_2$)$_w$NH—, or —N(H)(CH$_2$)$_w$NH—, where w is an integer ranging from 1 to 12. When R1 is a sugar, the sugar may be selected from glucose, β-glucose, a-galactoside, β-galactoside, a-glucuronose, neuraminide, or β-glucuronose.

In other embodiments, the conjugates of Formula (II) have the structure of Formula (IIb):

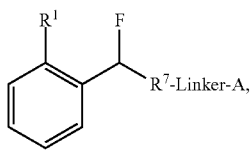
(IIb)

where $R^1$ is selected from phosphate, amide, nitro, urea, sulfate, methyl, ester, beta-lactam, or a sugar; and where $R^7$ is —(CH$_2$)$_w$NH—, —O(CH$_2$)$_w$NH—, —N(H)C(O)(CH$_2$)$_w$NH—, —C(O)N(H)(CH$_2$)$_w$NH—, —(CH$_2$)$_w$O—, —O(CH$_2$)$_w$O—, —O(CH$_2$CH$_2$O)$_w$—, —N(H)C(O)(CH$_2$)$_w$O—, —C(O)N(H)(CH$_2$)$_w$O—, —C(O)N(H)(CH$_2$CH$_2$O)$_w$—, —(CH$_2$)$_w$S—, —O(CH$_2$)$_w$S—, —N(H)C(O)(CH$_2$)$_w$S—, —C(O)N(H)(CH$_2$)$_w$S—, —(CH$_2$)$_w$NH—, —C(O)N(H)(CH$_2$CH$_2$O)$_w$CH$_2$CH$_2$NH, —C(O)(CH$_2$CH$_2$O)$_w$CH$_2$CH$_2$NH—, —C(O)N(H)(CH$_2$)NHC(O)CH(CH$_3$)(CH$_2$)$_w$NH—, or —N(H)(CH$_2$)$_w$NH—, where w is an integer ranging from 1 to 12.

In some embodiments of the conjugates of Formula (IIb), $R^1$ is a phosphate and $R^7$ is —C(O)N(H)(CH$_2$)$_w$NH—, and w ranges from 2 to 10.

In yet other embodiments, the conjugates of Formula (II) have the structure of Formula (IIc):

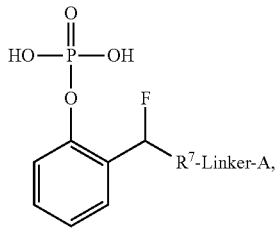
(IIc)

where $R^7$ is —(CH$_2$)$_w$NH—, —O(CH$_2$)$_w$NH—, —N(H)C(O)(CH$_2$)$_w$NH—, —C(O)N(H)(CH$_2$)$_w$NH—, —(CH$_2$)$_w$O—, —O(CH$_2$)$_w$O—, —O(CH$_2$CH$_2$O)$_w$—, —N(H)C(O)(CH$_2$)$_w$O—, —C(O)N(H)(CH$_2$)$_w$O—, —C(O)N(H)(CH$_2$CH$_2$O)$_w$—, —(CH$_2$)$_w$S—, —O(CH$_2$)$_w$S—, —N(H)C(O)(CH$_2$)$_w$S—, —C(O)N(H)(CH$_2$)$_w$S—, —(CH$_2$)$_w$NH—, —C(O)N(H)(CH$_2$CH$_2$O)$_w$CH$_2$CH$_2$NH, —C(O)(CH$_2$CH$_2$O)$_w$CH$_2$CH$_2$NH—, —C(O)N(H)(CH$_2$)NHC(O)CH(CH$_3$)(CH$_2$)$_w$NH—, or —N(H)(CH$_2$)$_w$NH—, where w is an integer ranging from 1 to 12.

In some embodiments, $R^7$ is C(O)N(H)(CH$_2$)$_w$NH and w is as defined above. In other embodiments, $R^7$ is C(O)N(H)(CH$_2$)$_w$NH and w ranges from 2 to 6.

In yet further embodiments, the conjugates of Formula (II) have the structure of Formula (IId):

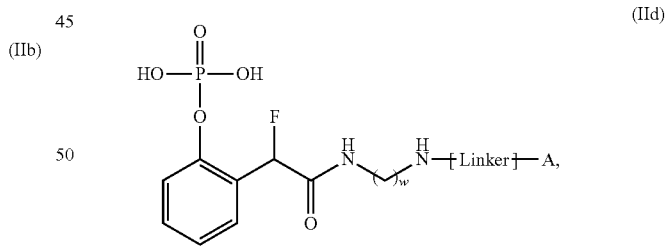
(IId)

where w ranges from 1 to 12, and

"Linker" and A are as defined above.

In some embodiments w ranges from 1 to 8. In other embodiments, w ranges from 2 to 8. In yet other embodiments, w ranges from 2 to 6. In further embodiments, w is 6.

Specific examples of the compounds of Formulas (II) include the following:

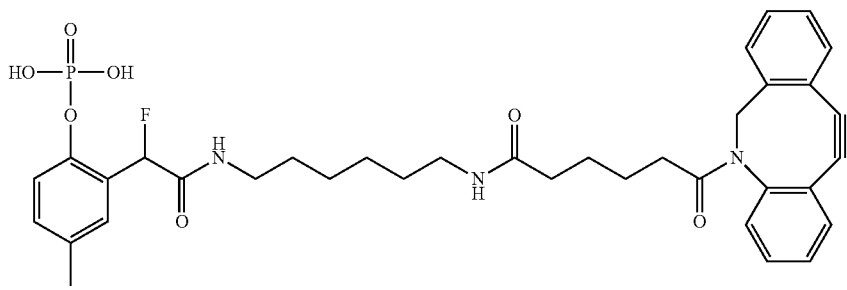

Quinone Methide-DBCO

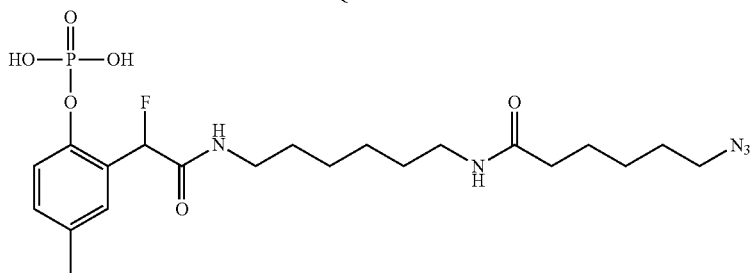

Quinone Methide-Azide

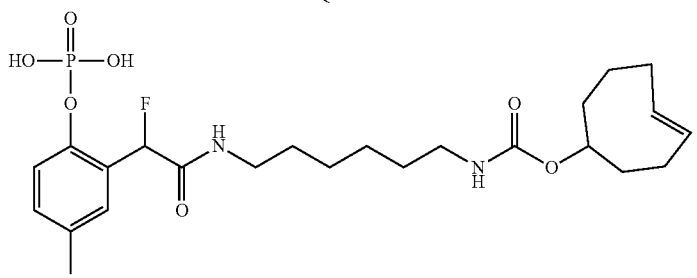

Quinone Methide-TCO

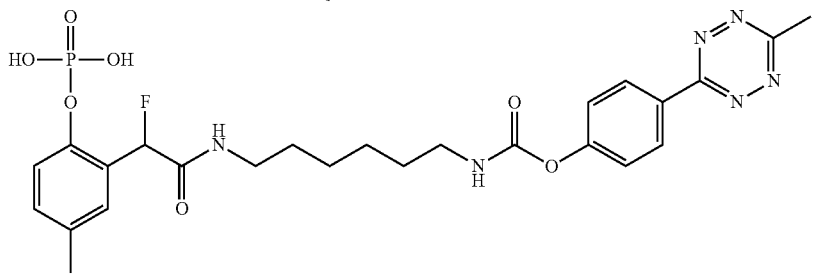

Quinone Methide-Tetrazine

The quinone methide precursor click conjugates of Formula (II) may be synthesized according to any method as known to those of ordinary skill in the art. In some embodiments, a reagent comprising the desired reactive functional group and linker are merely coupled with a quinone methide precursor or derivative or analog thereof as illustrated in the reaction schemes which follow. For example, a quinone methide precursor having a terminal amine group may be coupled to a compound comprising an amine reactive group (e.g. active esters such as N-Hydroxysuccinimide (NHS) or sulfo-NHS, isothiocyanates, isocyanates, acyl azides, sulfonyl chlorides, aldehydes, glyoxals, epoxides, oxiranes, carbonates, aryl halides, imidoesters, anhydrides and the like).

In some of the specific examples below, a Click partner having an NHS-ester group is coupled with a quinone methide precursor having a terminal amine. In some embodiments, the reaction takes place in DMSO and is allowed to react for 60 minutes. The reaction is then diluted with methanol and directly purified by preparative HPLC.

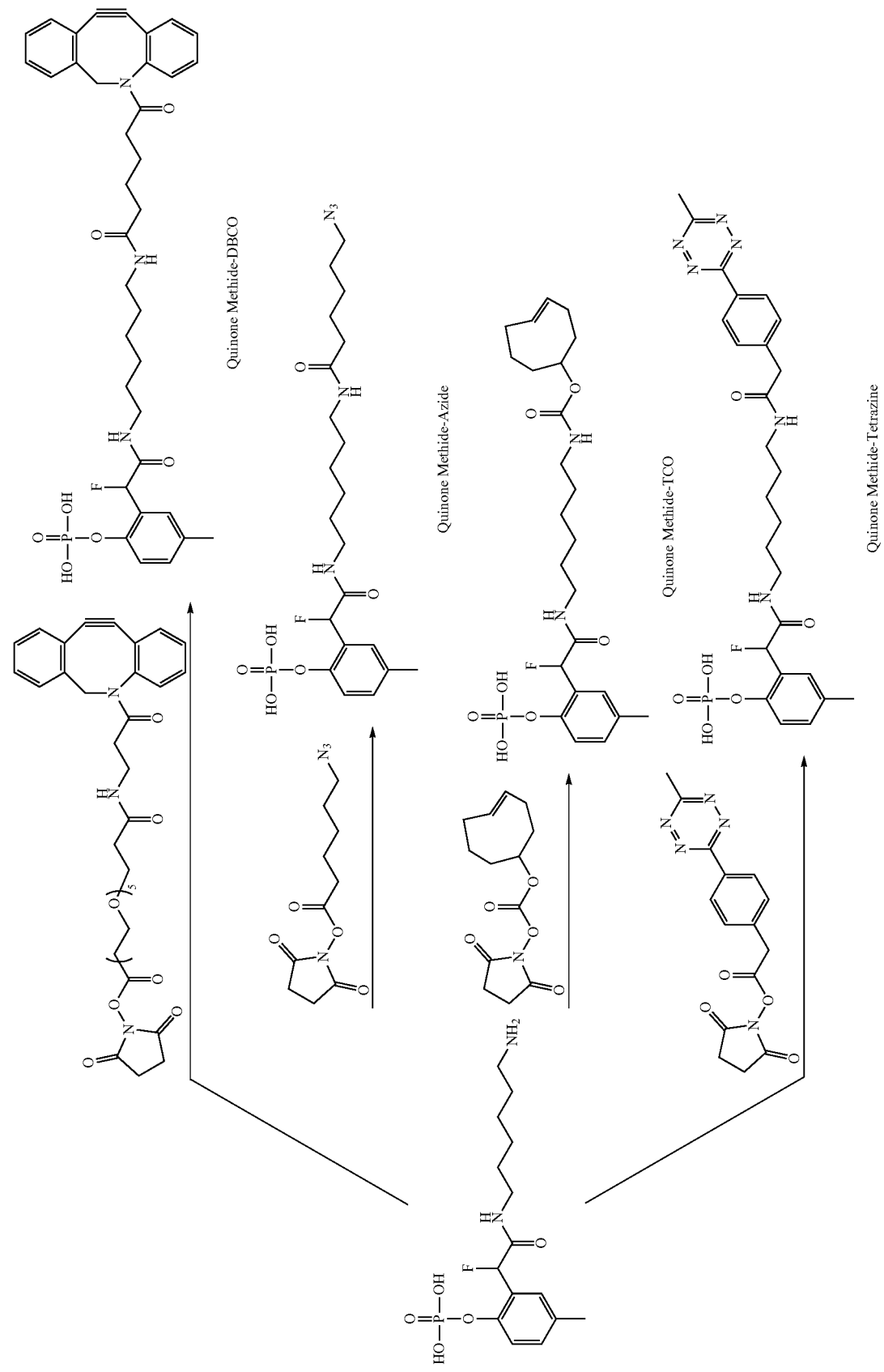
Scheme 1A: Examples of the synthesis of the compounds of Formula (II).

Tyramide "Click" Conjugates

In other embodiments, the compounds have Formula (III):

A—[—Linker—]—M    (III)

wherein A is as defined above; "Linker" is an optional linking group as defined above; and M is tyramide or a derivative or analog thereof. In some embodiments, the compounds of Formula (III) are a first member of a pair of click partners.

In some embodiments, the conjugates of Formula (III) comprise a tyramide derived from a compound having the structure of Formula (IIIa)

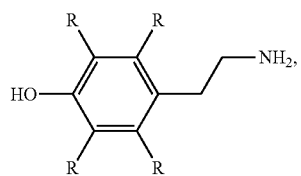
(IIIa)

wherein each R group is independently selected from hydrogen or lower alkyl group (which may be straight chain or branched) having between 1 and 4 carbon atoms, and where Linker and A are as defined herein.

In some embodiments, the compounds of Formula (III) comprise a tyramide derived from a compound having the structure of Formula (IIIb)

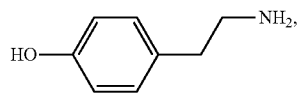
(IIIb)

where A is selected from an azide, a thiol, a 1,3-nitrone, a hydrazine, or a hydroxylamine, and where Linker is as defined herein.

In some embodiments, the compounds of Formula (III) comprise a moiety from a compound having the structure of Formulas (IIIc) or (IIId):

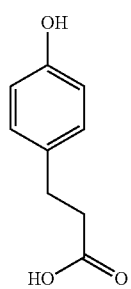
(IIIc)

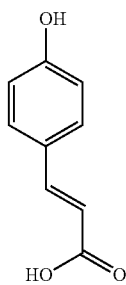
(IIId)

Non-limiting examples of particular tyramide click conjugates include the following:

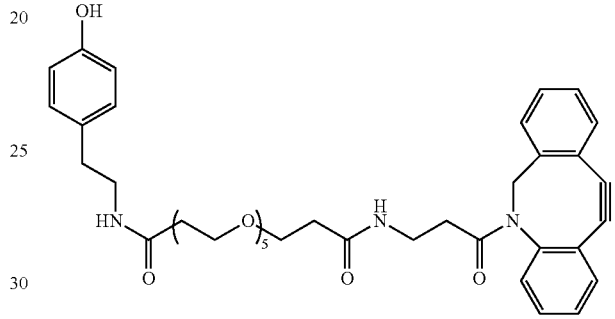
Tyramide-DBCO

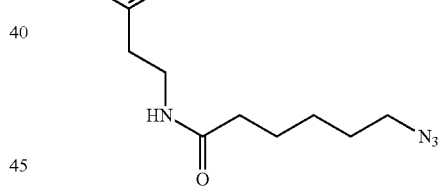
Tyramide-Azide

Tyrazide

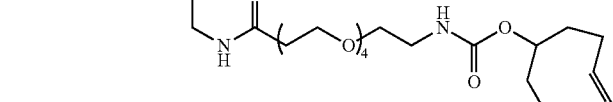
Tyramide-TCO

-continued

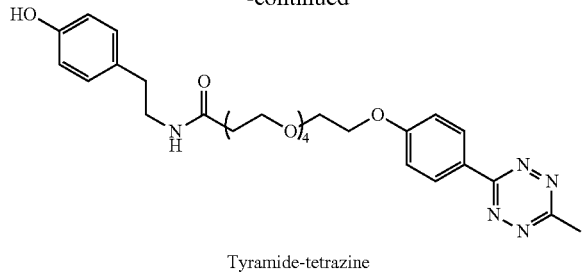

Tyramide-tetrazine

The tyramide click conjugates of Formula (III) may be synthesized according to any method as known to those of ordinary skill in the art. In some embodiments, a reagent comprising the desired reactive functional group and linker are merely coupled with a tyramide or derivative or analog thereof as illustrated in the reaction schemes below. For example, a tyramide (having a terminal amine group) may be coupled to a compound comprising an amine reactive group (e.g. active esters such as N-Hydroxysuccinimide (NHS) or sulfo-NHS, isothiocyanates, isocyanates, acyl azides, sulfonyl chlorides, aldehydes, glyoxals, epoxides, oxiranes, carbonates, aryl halides, imidoesters, anhydrides and the like).

In some of the specific examples below, a Click partner having an NHS-ester group is coupled with a tyramide. In some embodiments, the reaction takes place in DMSO and is allowed to react for 60 minutes. The reaction is then diluted with methanol and directly purified by preparative HPLC.

Scheme 1B: Examples of the synthesis of click conjugates having Formula (III).

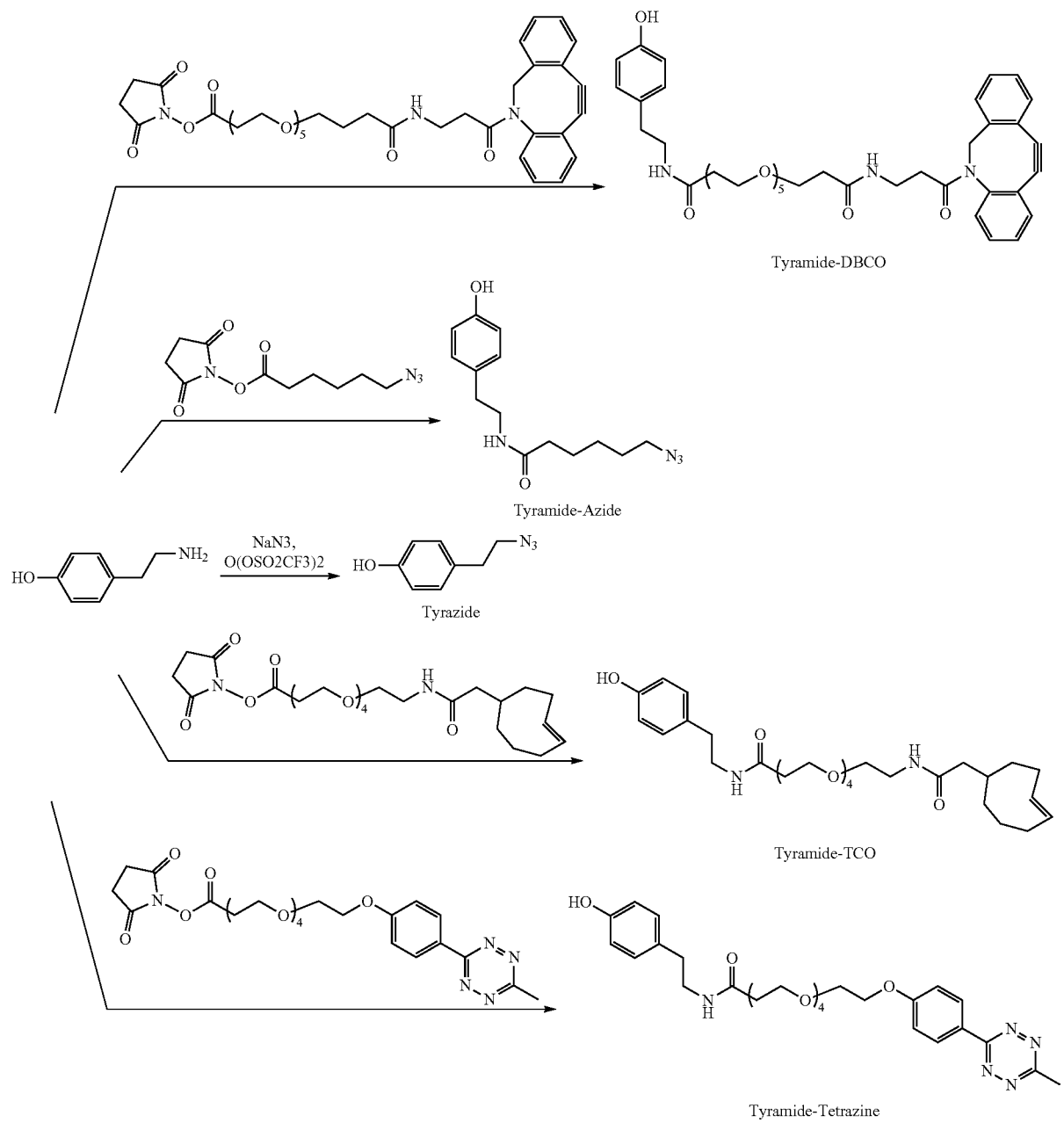

Reporter Moiety "Click" Conjugates

In other embodiments, the click conjugates of the present disclosure have the structure of Formula (IV):

A—[Linker]—Z  (IV), wherein A is as defined above; "Linker" is an optional linking group as defined above; and Z comprises at least one reporter moiety (the terms "reporter moiety" and "reporter" are used interchangeably herein). In some embodiments, the compounds of Formula (IV) are a second member of a pair of click partners.

In some embodiments, the conjugates of Formula (IV) comprise one reporter moiety, and thus the group Z is a reporter moiety coupled directly, or indirectly through a Linker, to the reactive functional group A. In other embodiments, the conjugates of Formula (IV) comprise a plurality of reporter moieties, and thus Z represents a group having two or more reporter moieties. In embodiments where Z represents a group having two or more reporter moieties, the group Z is coupled directly, or indirectly through a Linker, to the reactive functional group A.

In some embodiments, Z comprises two reporters. In other embodiments, Z comprises four reporters. In other embodiments, Z comprises six reporters. In yet other embodiments, Z comprises greater than 6 reporters. In embodiments where Z comprises more than one reporter, the reporters may be the same or different. For example, Z may comprise two of the same chromogens (e.g. two TAMRA chromogens). Alternatively, Z may comprise two different chromogens (e.g. TAMRA and cy5).

In some embodiments, Z comprises at least two reporter moieties, and the at least two reporter moieties are linked to each other via a straight chain or branched aliphatic group, optionally comprising one or more heteroatoms. In other embodiments, Z comprises at least two reporter moieties, and the at least two reporter moieties are linked to each other via a dendrimer or branched polymer.

In some embodiments, the compounds of Formula (IV) have the structure of Formula (V):

A—[Linker]—Scaffold—[Z]$_v$  (V), wherein

"Scaffold" is a group capable of coupling multiple reporter moieties, and v is an integer ranging from between 1 and 20.

In some embodiments, "Scaffold" is a polyamine (e.g. norspermidine, spermine, and derivatives or analogs thereof; or a polyamine comprising between 2 and 10 amine groups); a heterobifunctional linker (e.g. lysine or lysine derivative); a dendrimer (e.g. polyamidoamine (PAMAM) dendrimers, Janus dendrimers (i.e. dendrimers constituted of two dendrimeric wedges and terminated by two different functionalities), and bis-MPA dendrimers and derivatives thereof); or a polymer. In some embodiments, 'Scaffold' is a bond.

In some embodiments, the click conjugates have the following formulas:

N$_3$-Linker-Z,  (IVa)

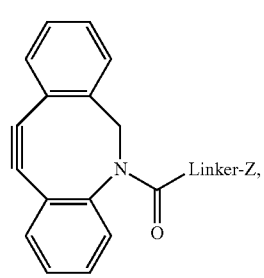  (IVb)

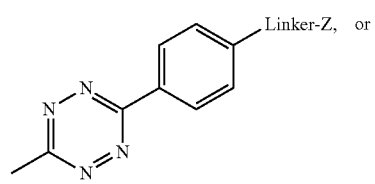  (IVc)

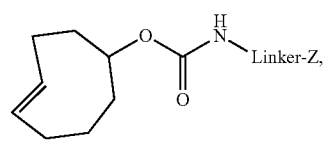  (IVd)

where Linker and Z are as defined herein,

In some embodiments, the reporter moiety is selected from a chromophore, a fluorophore, an enzyme, a hapten, or a chelator.

Non-limiting examples of suitable haptens include pyrazoles, particularly nitropyrazoles; nitrophenyl compounds; benzofurazans; triterpenes; ureas and thioureas, particularly phenyl ureas, and even more particularly phenyl thioureas; rotenone and rotenone derivatives, also referred to herein as rotenoids; oxazole and thiazoles, particularly oxazole and thiazole sulfonamides; coumarin and coumarin derivatives; cyclolignans, exemplified by Podophyllotoxin and Podophyllotoxin derivatives; and combinations thereof. Further examples of haptens and methods for their synthesis and use are disclosed in U.S. Pat. No. 7,695,929, the disclosure of which is hereby incorporated in its entirety herein by reference.

In some embodiments, suitable haptens include BD (benzodiazepine), BF (benzofurazan), DAB SYL (4-(dimethylamino)azobenzene-4'-sulfonamide, which has a max of about 436 nm), DCC (7-(diethylamino)coumarin-3-carboxylic acid), DIG (digoxigenin), DNP (dinitrophenyl), HQ (3-hydroxy-2-quinoxalinecarbamide) NCA (nitrocinnamic acid), NP (nitropyrazole), PPT (Podophyllotoxin), Rhod (rhodamine), ROT (rotenone), and TS (thiazolesulfonamide). Other suitable haptens include biotin and fluorescein derivatives (FITC (fluoresceinisothiocyanate), TAMRA (tetramethylrhodamine), Texas Red), and Rhodamine 110 (Rhodamine).

Non-limiting examples of suitable chromophores include coumarin and coumarin derivatives.

Examples of coumarin-based chromophores include DCC and 2,3,6,7-tetrahydro-1 1-oxo-1H,5H,1 1H-[1]benzopyrano[6,7,8-ij]quinolizine-10-carboxylic acid. Other suitable chromophores include diazo-containing chromogens, such as tartrazine. Yet other suitable chromophores include triarylmethane, including those provided below

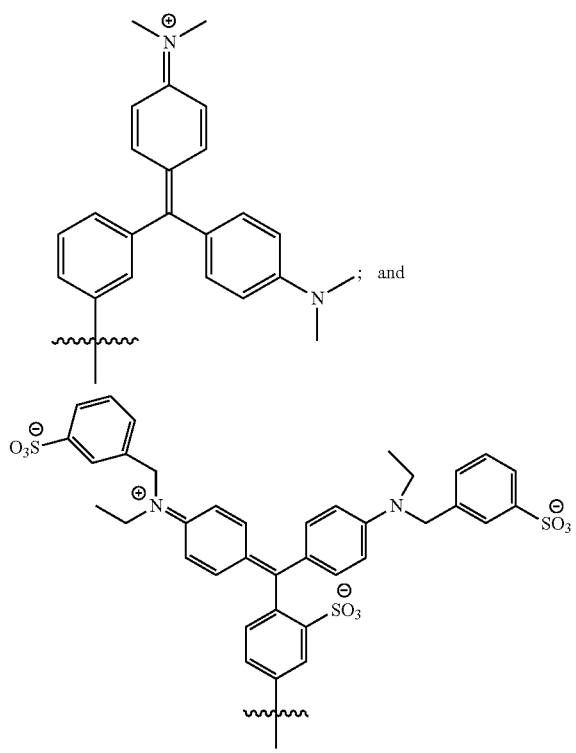
Other non-limiting examples of suitable chromophores include those provided below:
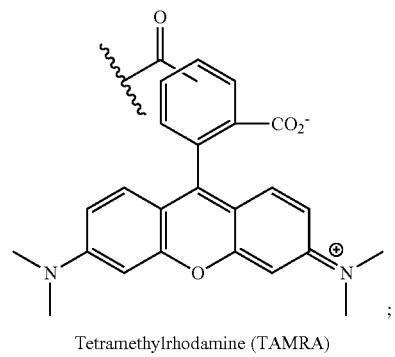
Tetramethylrhodamine (TAMRA)
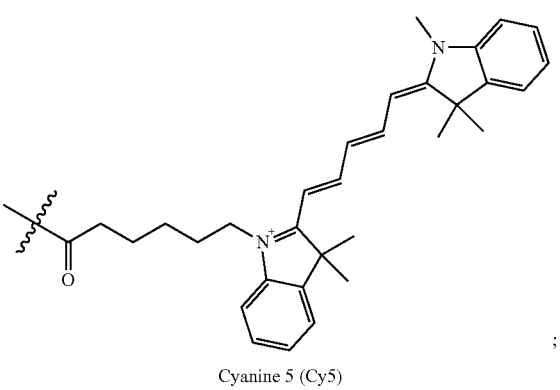
Cyanine 5 (Cy5)
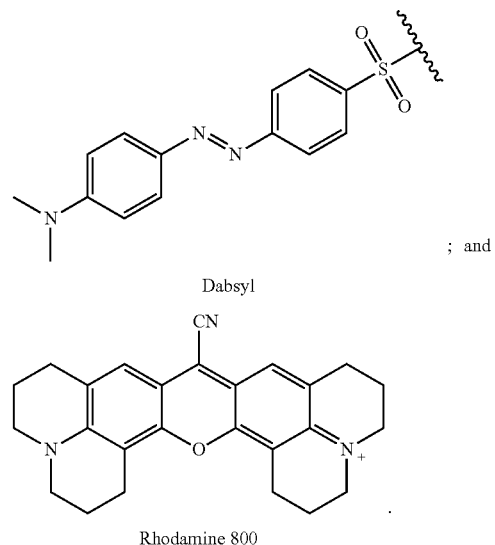
Dabsyl
Rhodamine 800
Other suitable chromophores include annulated chromophores, such as those provided below:
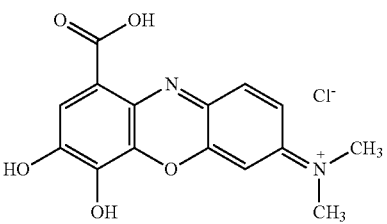
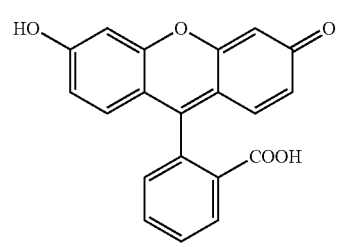
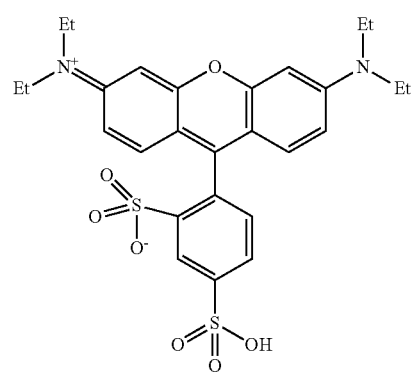

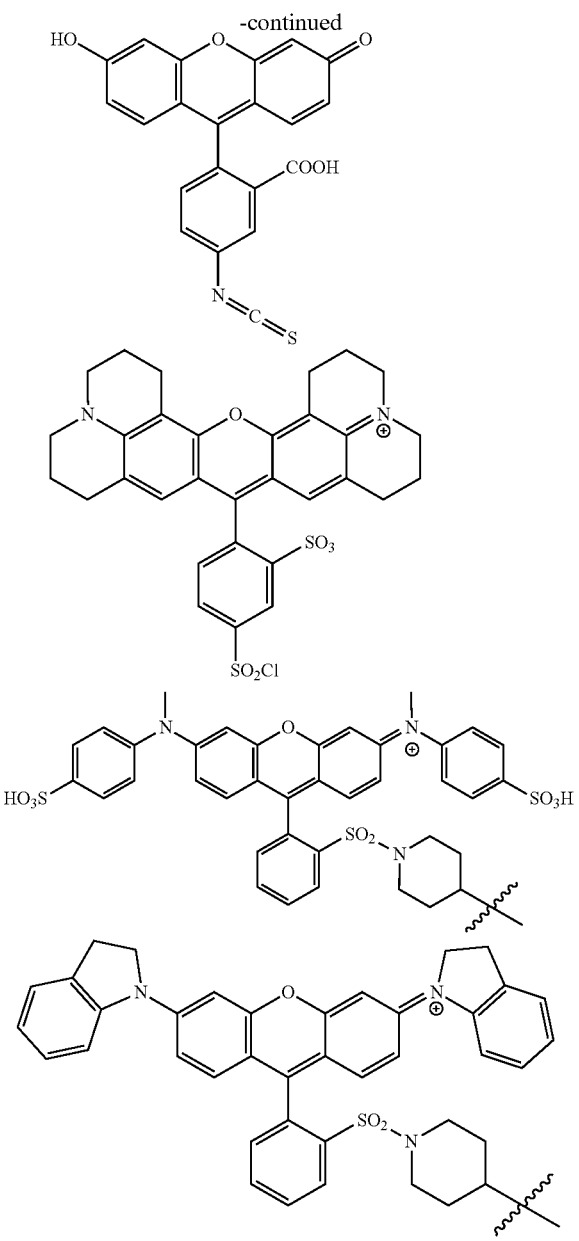

Fluorophores belong to several common chemical classes including coumarins, fluoresceins (or fluorescein derivatives and analogs), rhodamines, resorufins, luminophores and cyanines. Additional examples of fluorescent molecules can be found in Molecular Probes Handbook—A Guide to Fluorescent Probes and Labeling Technologies, Molecular Probes, Eugene, Oreg., TheroFisher Scientific, 11th Edition. In other embodiments, the fluorophore is selected from xanthene derivatives, cyanine derivatives, squaraine derivatives, naphthalene derivatives, coumarin derivatives, oxadiazole derivatives, anthracene derivatives, pyrene derivatives, oxazine derivatives, acridine derivatives, arylmethine derivatives, and tetrapyrrole derivatives. In other embodiments, the fluorescent moiety is selected from a CF dye (available from Biotium), DRAQ and CyTRAK probes (available from BioStatus), BODIPY (available from Invitrogen), Alexa Fluor (available from Invitrogen), DyLight Fluor (e.g. DyLight 649) (available from Thermo Scientific, Pierce), Atto and Tracy (available from Sigma Aldrich), FluoProbes (available from Interchim), Abberior Dyes (available from Abberior), DY and MegaStokes Dyes (available from Dyomics), Sulfo Cy dyes (available from Cyandye), HiLyte Fluor (available from AnaSpec), Seta, SeTau and Square Dyes (available from SETA BioMedicals), Quasar and Cal Fluor dyes (available from Biosearch Technologies), SureLight Dyes (available from APC, RPEPerCP, Phycobilisomes)(Columbia Biosciences), and APC, APCXL, RPE, BPE (available from Phyco-Biotech, Greensea, Prozyme, Flogen).

Figure 14:
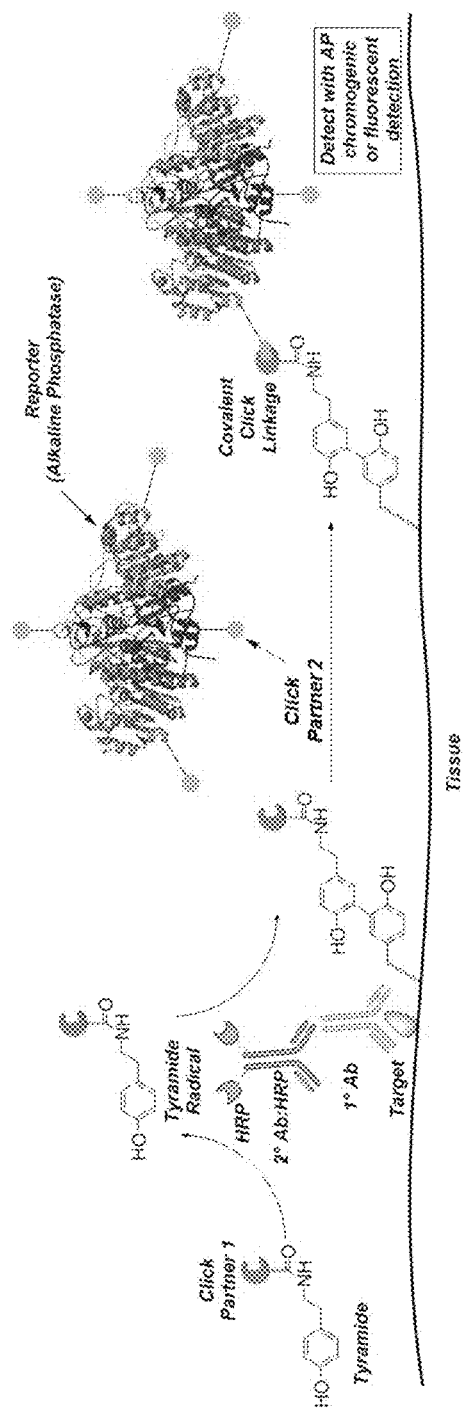
FIG. 14 sets forth a reaction scheme illustrating the reaction between a tyramide containing click conjugate and a tissue-bound enzyme; followed by reaction between the resulting tissue-click conjugate complex and a second click conjugate, the second click conjugate comprising an alkaline phosphatase reporter moiety.

Suitable enzymes include, but are not limited to, horseradish peroxidase, alkaline phosphatase, acid phosphatase, glucose oxidase, neuraminidase, β-galactosidase, β-glucuronidase or β-lactamase. In other embodiments, enzymes include oxidoreductases or peroxidases (e.g. HRP, AP). Use of an enzyme as a reporter moiety is further illustrated with reference to FIG. 14 herein. There, the second member of a pair of click conjugates comprises a compound of Formula (IV), where Z is an enzyme, in particular an alkaline phosphatase. As will be appreciated further herein, the resulting click adduct may be detected by introducing further alkaline phosphatase reporters (chromogens, fluorophores).

In some embodiments, the reporter moiety is a chelator or chelating agent, which may become chelated in the presence of a lanthanide (e.g. europium). Without wishing to be bound by any particular theory, it is believed that the lanthanide atoms may be detected using Inductively Coupled Plasma Mass Spectral Imaging (ICP-MSI). In addition, the lanthanides may be detected using time-resolved fluorescence microscopy, which take advantage of the relatively long lifetimes of the lanthanide luminescence compared to conventional fluorophores. In order to visualize the lanthanides, an antenna ligand must be present to absorb and transfer energy to the normally poorly-absorbing lanthanides. The reaction product of the DBCO-azide Click reaction may be able to act as the antenna ligand, greatly simplifying the design of these systems.

An example of a compound of Formula (IV) comprising an azide reactive group conjugated to a chelator moiety is shown below:

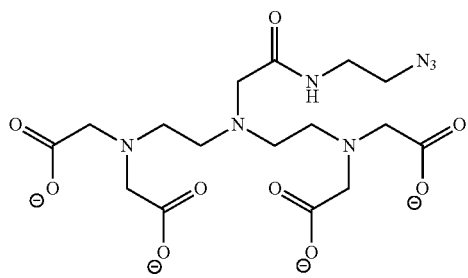 [SMILES: [N-]=[N+]=NCCNC(=O)CN(CCN(CC(=O)[O-])CC(=O)[O-])CCN(CC(=O)[O-])CC(=O)[O-]]

In some specific embodiments, the reporter moiety portion (Z) of the click conjugates of Formula (IV) are selected from:

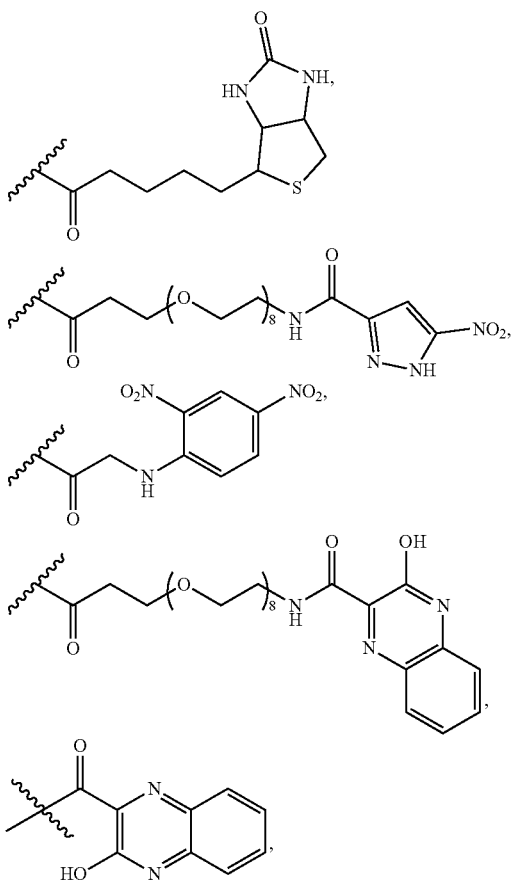

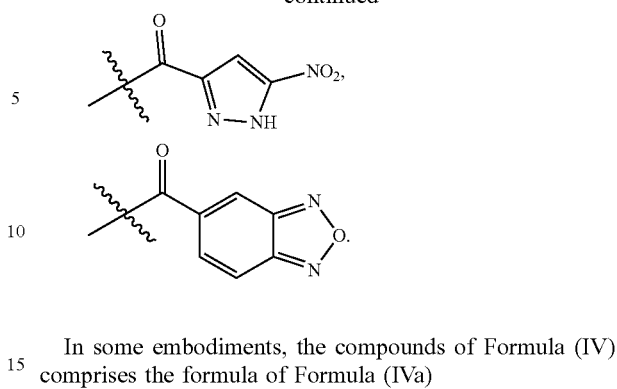

In some embodiments, the compounds of Formula (IV) comprises the formula of Formula (IVa)

(IVa)

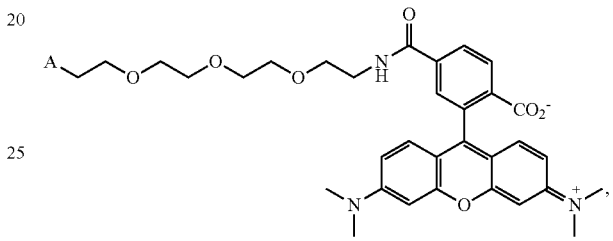

wherein A is as recited above. While Formula (IVa) depicts the compound has comprising a PEG linker, other suitable linkers may be substituted.

In some embodiments, the compounds of Formula (IV) comprises the formula of Formula (IVb)

(IVb)

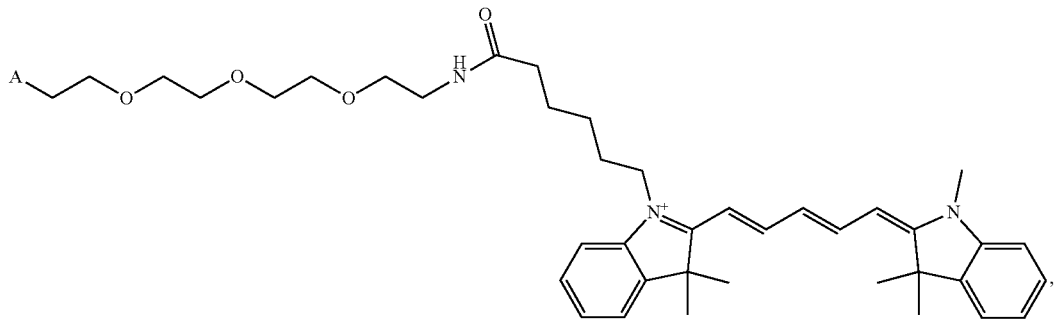

wherein A is as recited above. While Formula (IVb) depicts the compound has comprising a PEG linker, other suitable linkers may be substituted.

In some embodiments, the compounds of Formula (IV) comprises the formula of Formula (IVc)

(IVc)

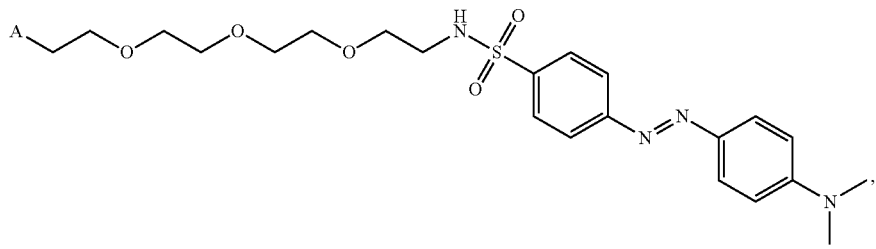

wherein A is as recited above. While Formula (IVc) depicts the compound has comprising a PEG linker, other suitable linkers may be substituted.

In some embodiments, the compounds of Formula (IV) comprises the formula of Formula (IVd)

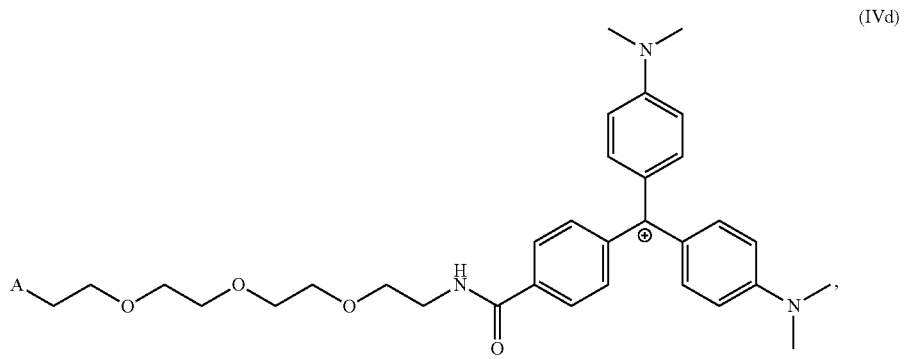

(IVd)

wherein A is as recited above. While Formula (IVd) depicts the compound has comprising a PEG linker, other suitable linkers may be substituted.

Specific non-limiting examples of conjugates of the Formula (IV) include the following:

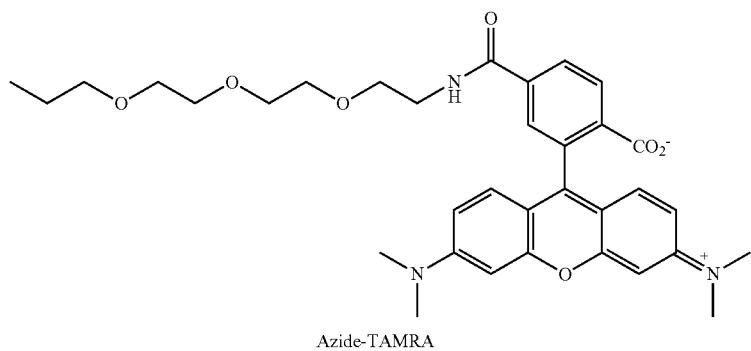

Azide-TAMRA

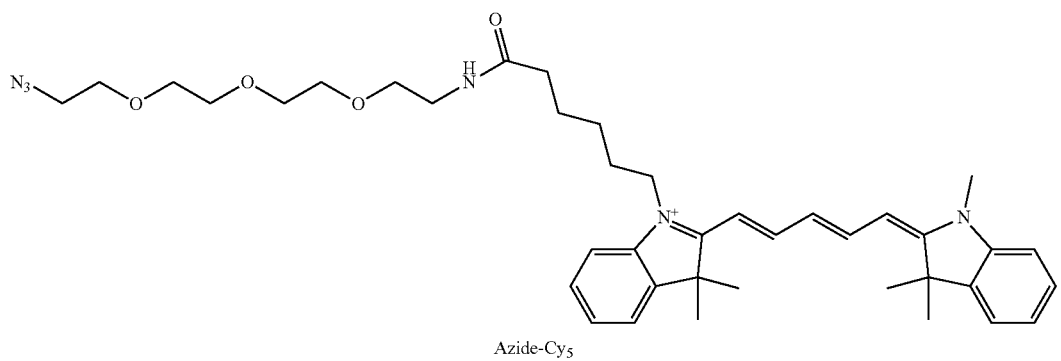

Azide-Cy$_5$

-continued
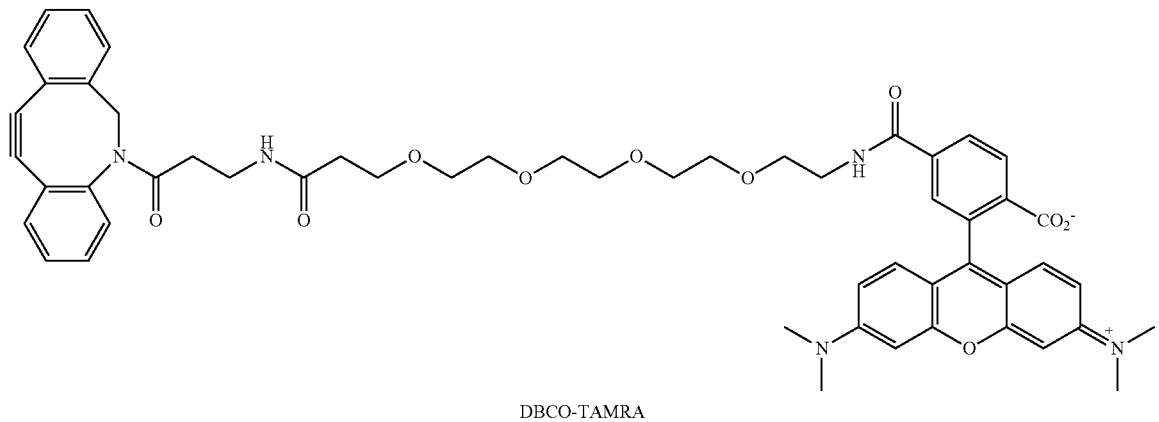
DBCO-TAMRA
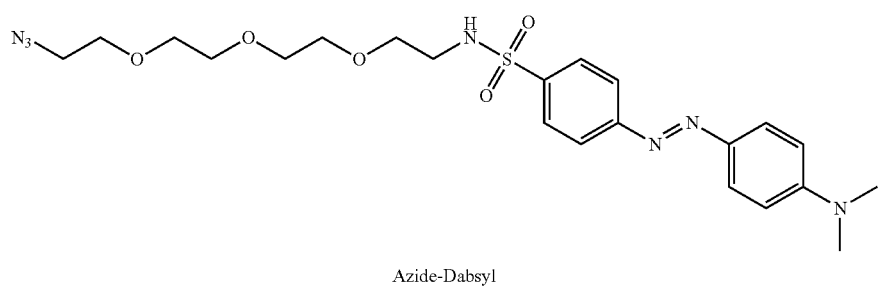
Azide-Dabsyl
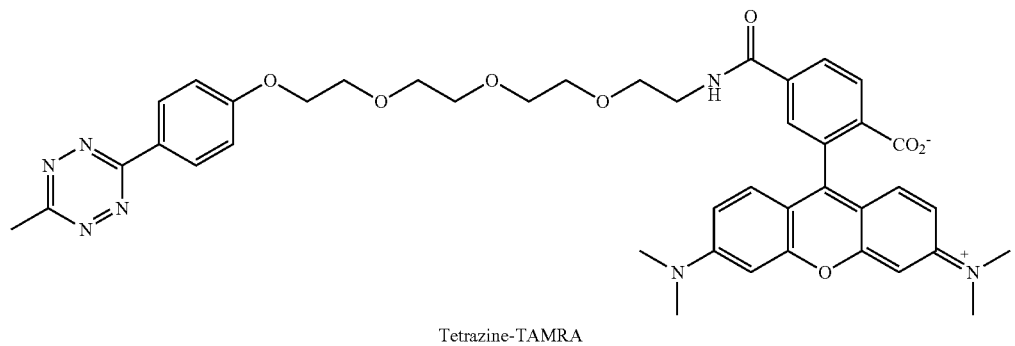
Tetrazine-TAMRA
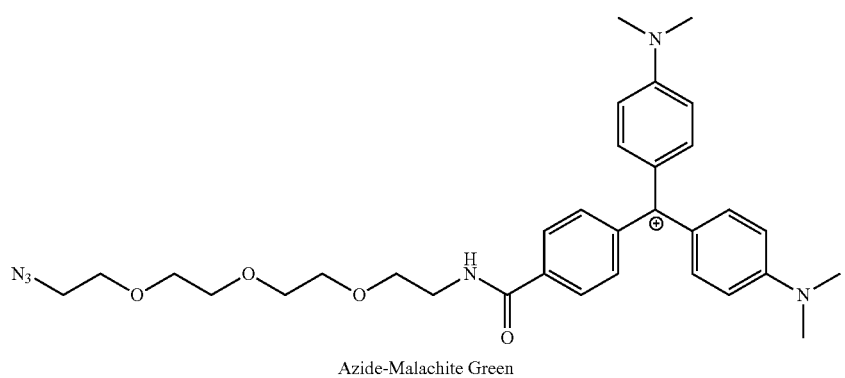
Azide-Malachite Green

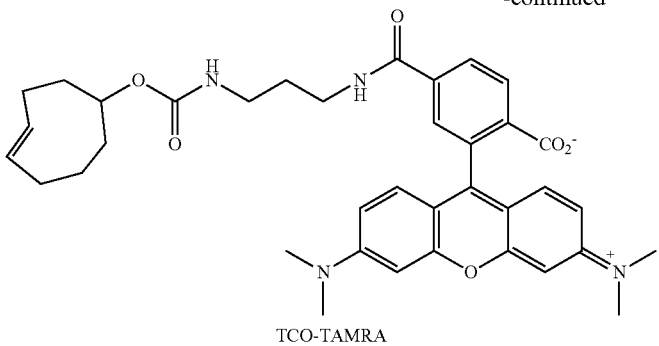

TCO-TAMRA

A non-limiting example of a conjugate of Formula (V) is illustrated below:

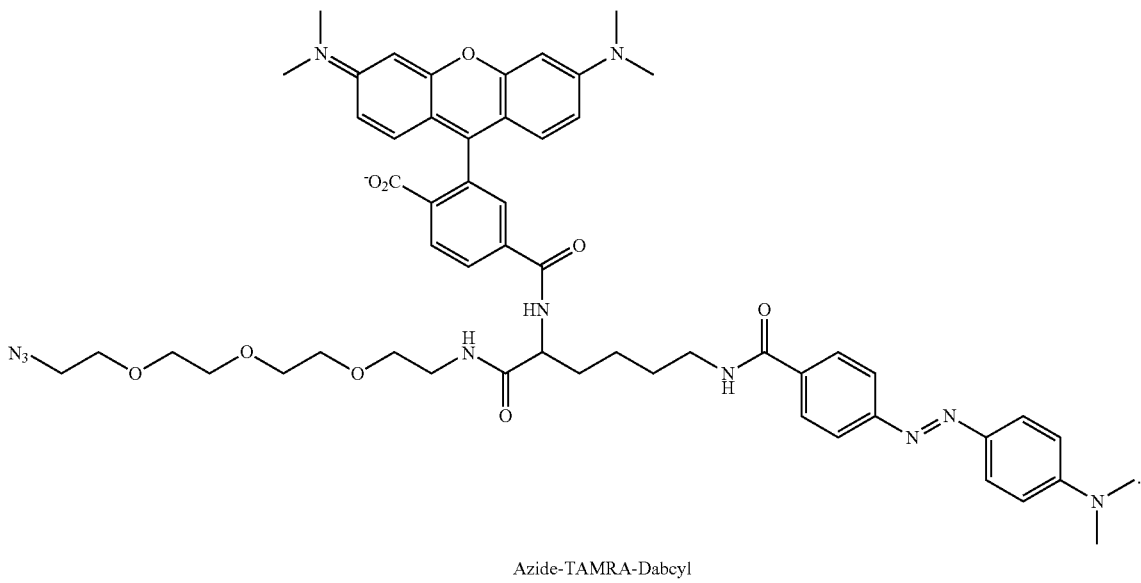

Azide-TAMRA-Dabcyl

The reporter moiety compounds of Formula (IV) may be synthesized according to methods known to those of ordinary skill in the art. Example synthetic procedure for the coupling of an NHS ester to an amine. This procedure can be applied to the reaction of any tyramine or quinone methide precursor containing an amine or NHS functionality with a Click partner containing an amine or NHS ester functionality. It can also be applied to the reaction of a reporter group (chromogen, hapten, etc.) containing an amine or NHS functionality with a Click partner containing an amine or NHS ester functionality.

Tyramide-peg5-DBCO. Tyramine (1.1 eq, 110 mg, 0.79 mmol) was dissolved in DMSO (3 mL) followed by addition of triethylamine (5.0 eq, 360 mg, 3.6 mmol). DBCO-peg5-DBCO (1.0 eq, 500 mg, 0.72 mmol) was then added, and the resulting reaction mixture was stirred for 1 hour at room temperature. The reaction mixture was diluted with MeOH (2 mL) and the resulting mixture was purified by preparative RP-HPLC (C18; 40 mL/min; 0.05% TFA in H2O:MeCN 95:5 to 5:95 over 40 minutes) to give Tyramide-peg5-DBCO (450 mg, 87% yield) as a colorless glass after removal of solvents under high vacuum. MS (ESI) m/z (M+H)+ calcd for C40H50N3O9+ 716.4, found 716.6.

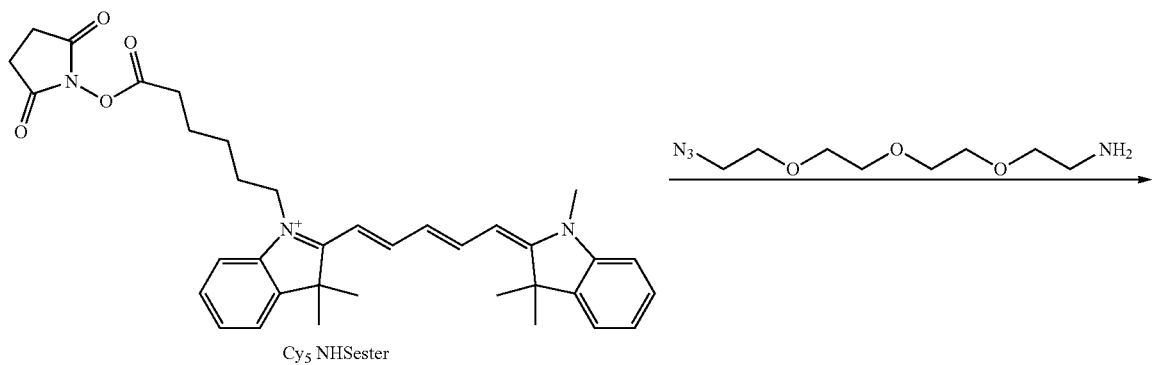
Cy₅ NHSester
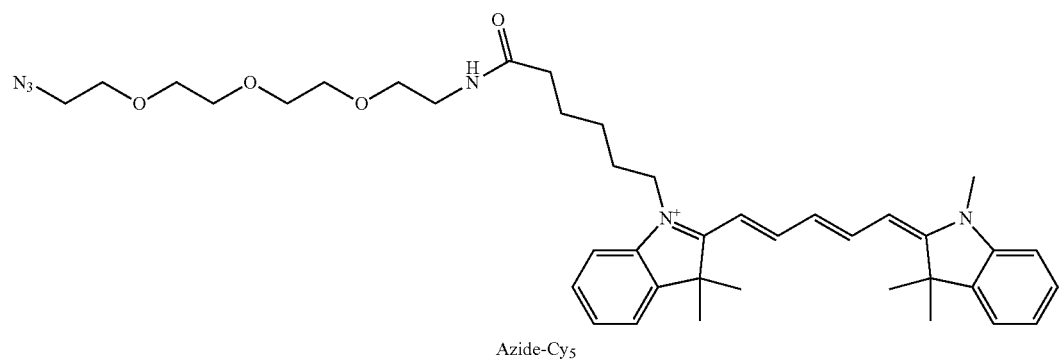
Azide-Cy₅
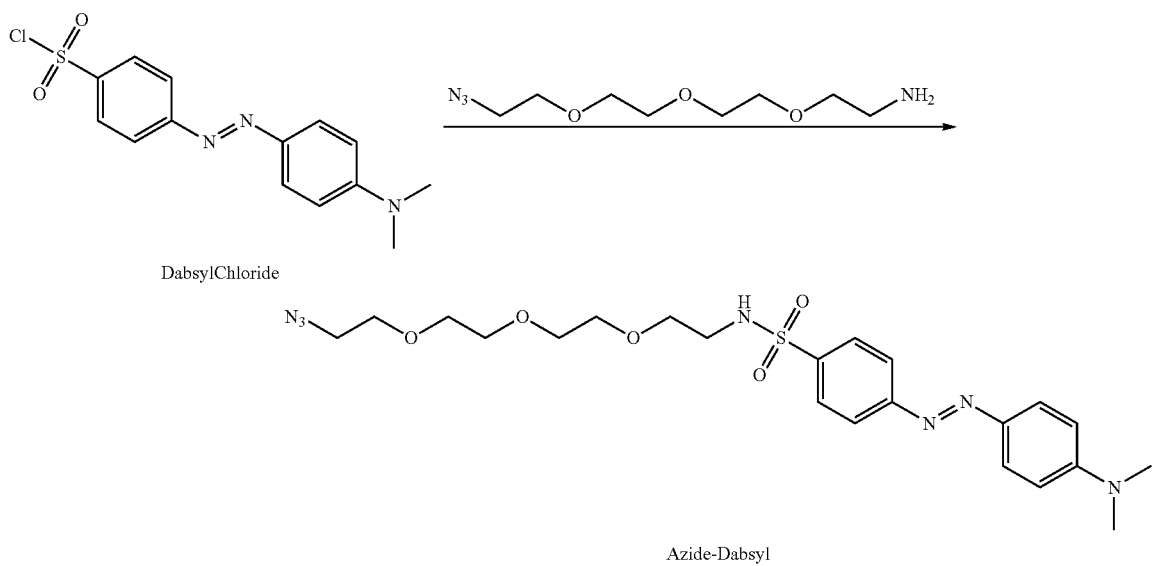
DabsylChloride
Azide-Dabsyl
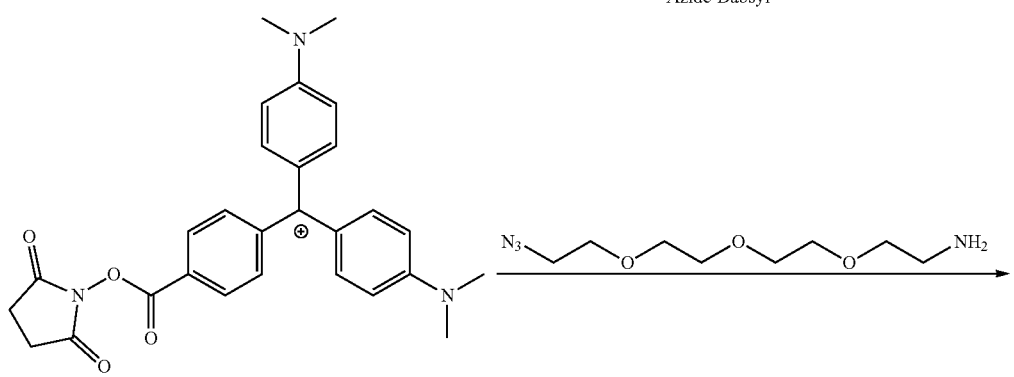

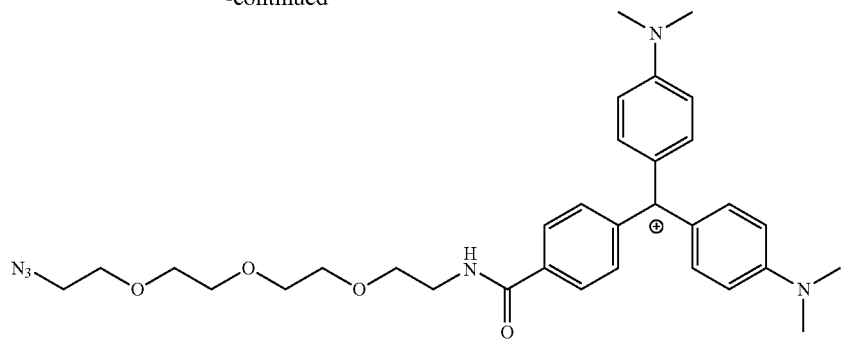

Coupling of Click Conjugate Pairs

The skilled artisan will recognize that the click conjugates disclosed herein are suitable for coupling to each other to form "click adducts." The skilled artisan will also recognize that for one member of a pair of click conjugates to react with another member of the pair of click conjugates, and thus form a covalent bond, the two members of the pair of click conjugates must have reactive functional groups capable of reacting with each other. The table which follows exemplifies different pairs of reactive functional groups that will react with each other to form a covalent bond.

| Reactive Functional Group on a First Member of a Pair of Click Conjugates | Reactive Functional Group on a Second Member of a Pair of Click Conjugates |
| --- | --- |
| DBCO | Azide |
| Alkene | Tetrazine |
| TCO | Tetrazine |
| Maleimide | Thiol |
| DBCO | 1,3-Nitrone |
| Aldehyde or ketone | Hydrazine |
| Aldehyde or ketone | Hydroxylamine |
| Azide | DBCO |
| Tetrazine | TCO |
| Thiol | Maleimide |
| 1,3-Nitrone | DBCO |
| Hydrazine | Aldehyde or ketone |
| Hydroxylamine | Aldehyde or ketone |
| Tetrazine | Alkene |

Figure 3A:
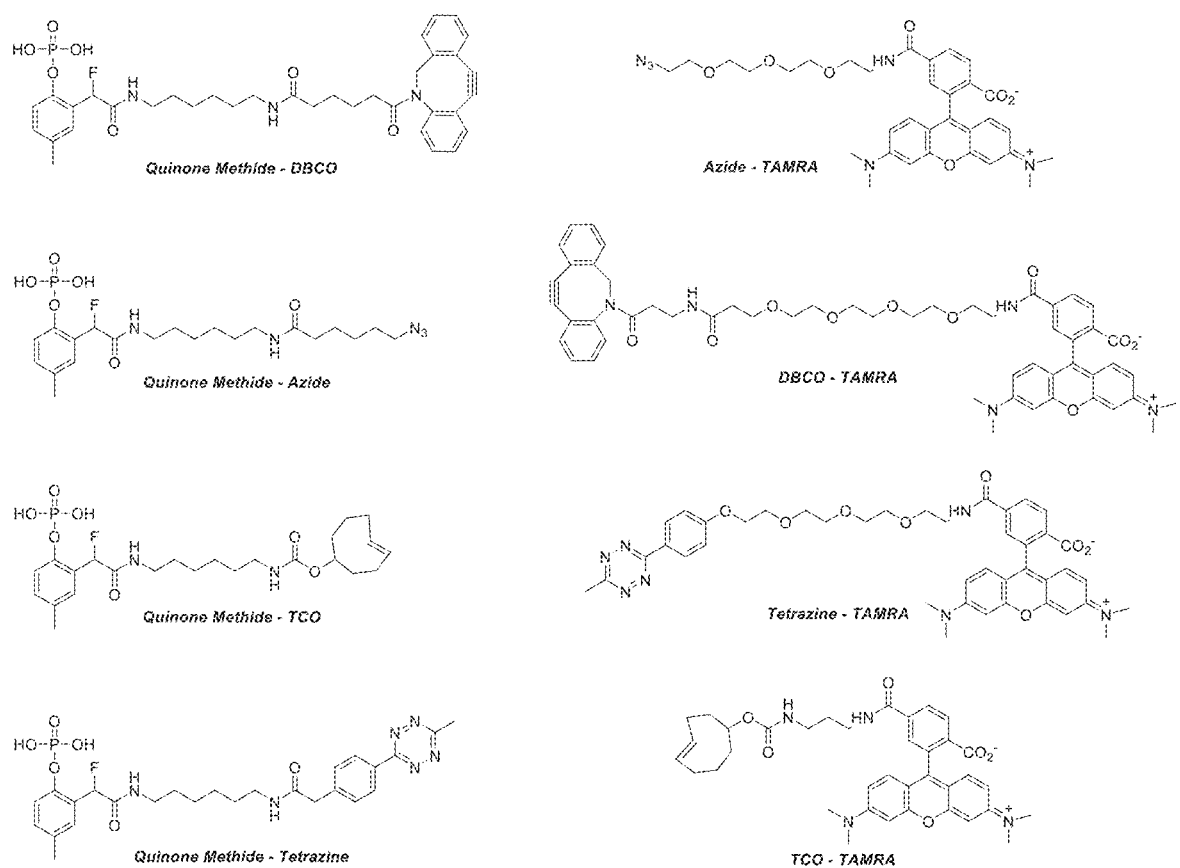
FIG. 3A sets forth examples of first and second members of a pair of click conjugates, where the first member of each pair of click conjugates comprises a compound of Formula (II) as described herein.
Figure 3B:
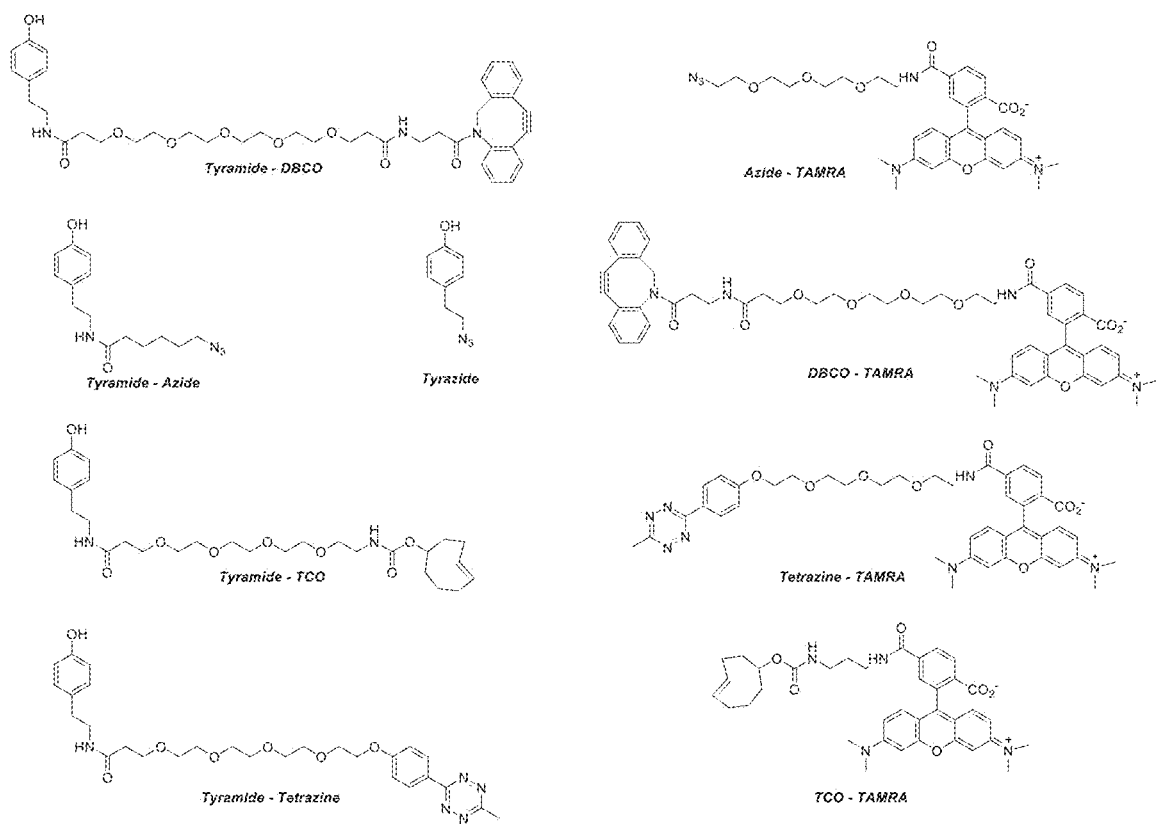
FIG. 3B sets forth examples of first and second members of a pair of click conjugates, where the first member of each pair of click conjugates comprises a compound of Formula (III) as described herein.
Figure 4:
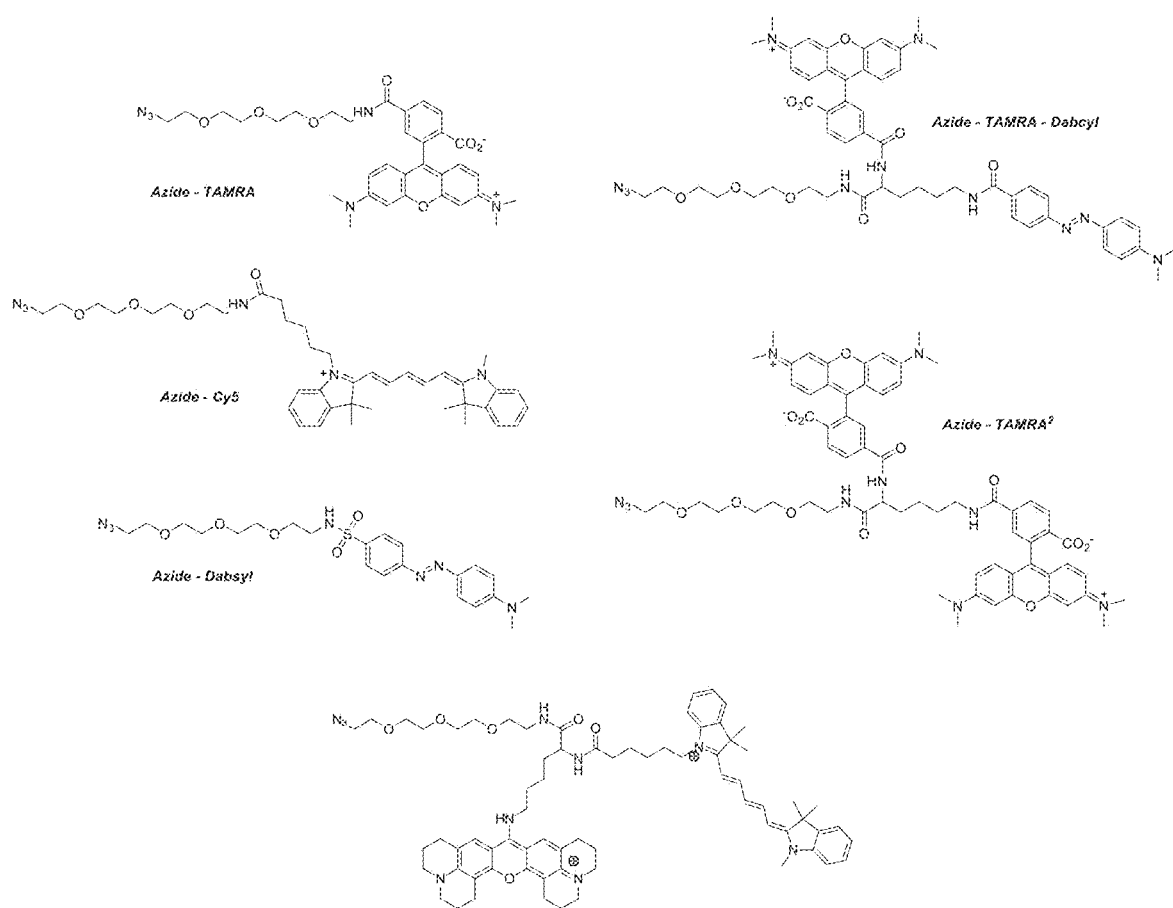
FIG. 4 sets forth examples of click conjugates comprising at least one chromophore and a reactive functional group.
Figure 5A:
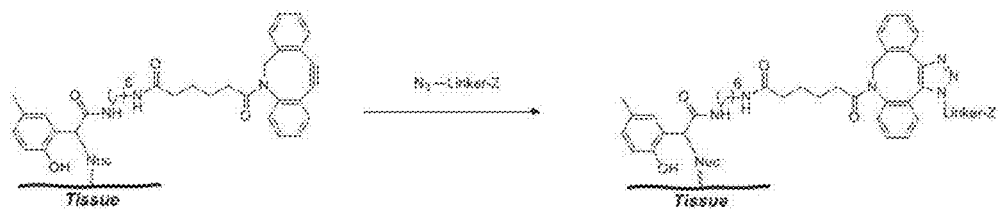
FIG. 5A illustrates the reaction between a quinone methide containing click conjugate bound to tissue (a tissue-click conjugate complex) and a click conjugate having an azide moiety and comprising at least one reporter moiety.
Figure 5B:
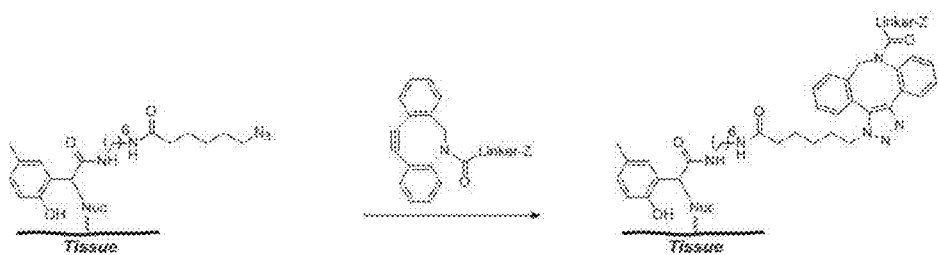
FIG. 5B illustrates the reaction between a quinone methide containing click conjugate bound to tissue (a tissue-click conjugate complex) and a click conjugate having a DBCO moiety and comprising at least one reporter moiety.
Figure 5C:
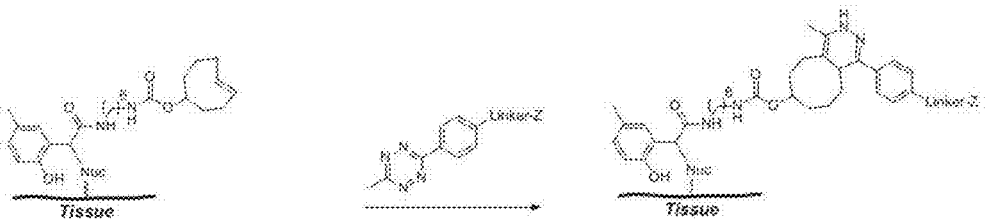
FIG. 5C illustrates the reaction between a quinone methide containing click conjugate bound to tissue (a tissue-click conjugate complex) and a click conjugate having a tetrazine moiety and comprising at least one reporter moiety.
Figure 5D:
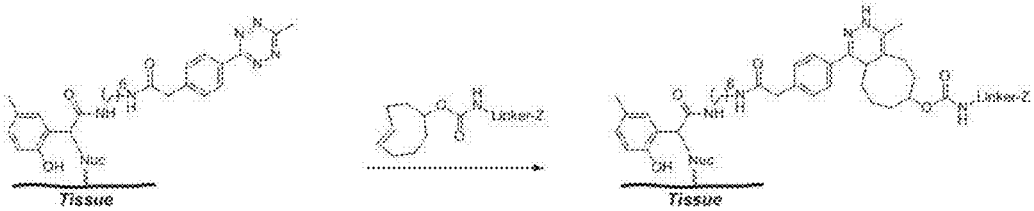
FIG. 5D illustrates the reaction between a quinone methide containing click conjugate bound to tissue (a tissue-click conjugate complex) and a click conjugate having a TCO moiety and comprising at least one reporter moiety.
Figure 6A:
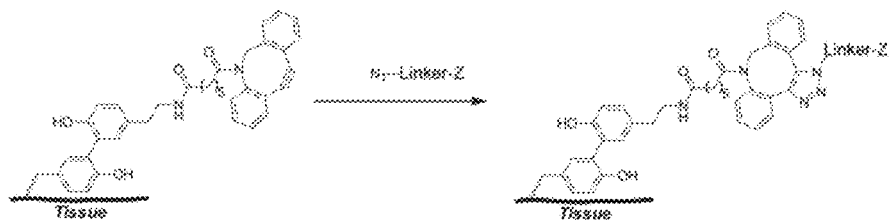
FIG. 6A illustrates the reaction between a tyramide containing click conjugate bound to tissue (a tissue-click conjugate complex) and a click conjugate having an azide moiety and comprising at least one reporter moiety.
Figure 6B:
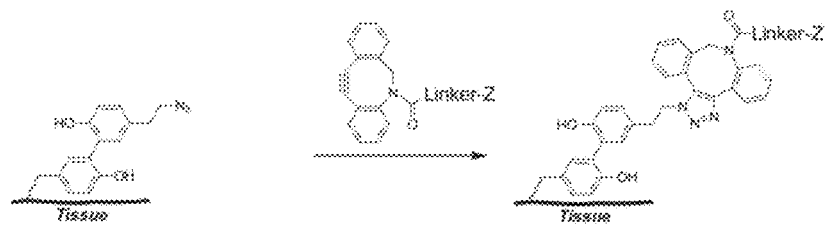
FIG. 6B illustrates the reaction between a tyramide containing click conjugate bound to tissue (a tissue-click conjugate complex) and a click conjugate having a DBCO moiety and comprising at least one reporter moiety.
Figure 6C:
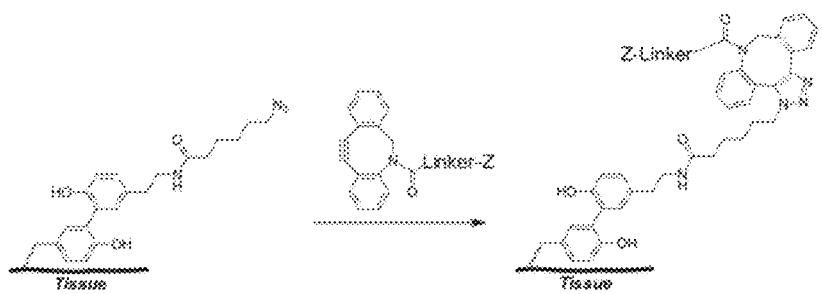
FIG. 6C illustrates the reaction between a tyramide containing click conjugate bound to tissue (a tissue-click conjugate complex) and a click conjugate having a DBCO moiety and comprising at least one reporter moiety.
Figure 6D:
FIG. 6D illustrates the reaction between a tyramide containing click conjugate bound to tissue (a tissue-click conjugate complex) and a click conjugate having a tetrazine moiety and comprising at least one reporter moiety.
Figure 6E:
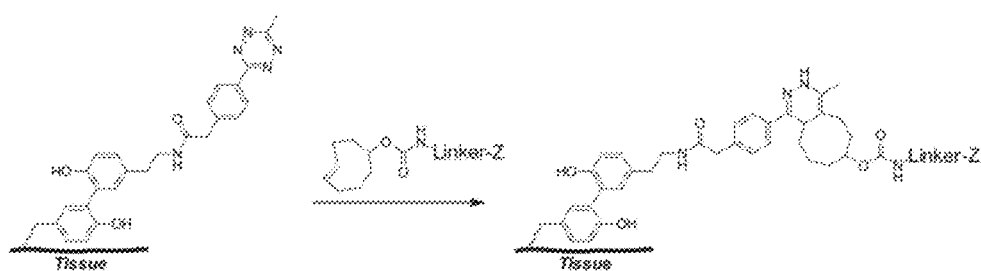
FIG. 6E illustrates the reaction between a tyramide containing click conjugate bound to tissue (a tissue-click conjugate complex) and a click conjugate having a TCO moiety and comprising at least one reporter moiety.

Specific non-limiting examples of pairs of click conjugates possessing these reactive function groups are illustrated in FIGS. 3 and 4. In particular, FIG. 3 provides examples of pairs of click conjugates, where one member of each pair of click conjugates comprises a compound of Formula (II). FIG. 4 also provides examples of pairs of click conjugates, where one member of each pair of click conjugates comprises a compound of Formula (III).

In some embodiments, the click conjugates are coupled via "strain-promoted azide-alkyne cycloaddition" (SPAAC), or "TCO-tetrazine ligation" (TTL). SPAAC involves the reaction between azides and strained alkynes, whose high energy allows the 1,3-dipolar cycloaddition to occur in the absence of a Cu(I) catalyst (required for traditional azide-alkyne "click" chemistry). In some embodiments, dibenzocyclooctynes are utilized as the strained cyclooctyne due to their commercial availability and literature precedent. TTL utilizes the reaction between trans-cyclooctene and tetrazine to form a dihydropyridazine bond. These reagents are also commercially available and have been shown to react orthogonally to the SPAAC system.

The schematics which follow further illustrate the coupling of pairs of click conjugates comprising difference reactive functional groups. In the schemes which follow, one member of the pair of click conjugates is provided as an immobilized, tissue-click conjugate complex. As will be described further herein, the immobilized, tissue-click conjugate complex is formed through the reaction of a click conjugate having either Formula (II) or (III) with an appropriate enzyme, and the subsequent coupling of a reactive intermediate generated therefrom with tissue.

For example, Scheme 2 illustrates the reaction between an immobilized tissue-click conjugate complex having a DBCO reactive functional group, and a second click conjugate of Formula (IV) comprising a reactive azide group and at least one reporter moiety Z. In some embodiments, the resulting adduct comprises one reporter moiety. In other embodiments, the resulting adduct comprises at least two reporter moieties, such as joined via a scaffold (e.g. a lysine linker or a dendrimer). In some embodiments, the at least one reporter moiety Z is a chromophore. In some embodiments, the at least one chromophore is selected from TAMRA, Cy5, Dabsyl, and Dabcyl. In some embodiments, the adduct comprises two TAMRA chromophores, such as linked via lysine.

Scheme 2

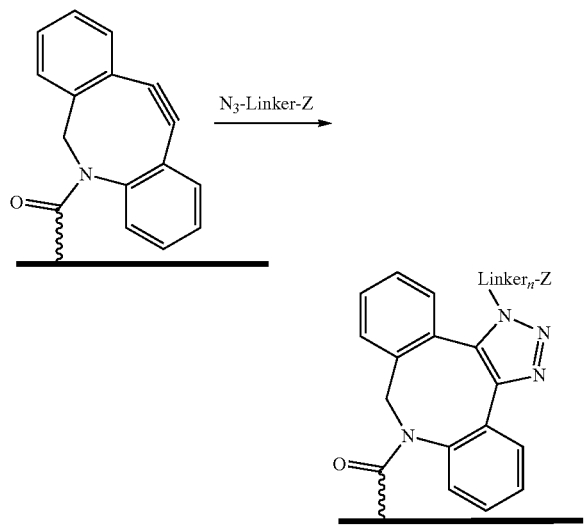

Likewise, Scheme 3 illustrates the reaction between an immobilized tissue-click conjugate complex having a TCO reactive functional group, and a second click conjugate of Formula (IV) comprising a reactive tetrazine group and at least one reporter moiety Z. In some embodiments, the resulting adduct comprises one reporter moiety. In other embodiments, the resulting adduct comprises at least two reporter moieties, such as joined via a scaffold (e.g. a lysine linker or a dendrimer). In some embodiments, the at least one reporter moiety Z is a chromophore. In some embodiments, the at least one chromophore is selected from TAMRA, Cy5, Dabsyl, and Dabcyl. In some embodiments, the adduct comprises two TAMRA chromophores, such as linked via lysine.

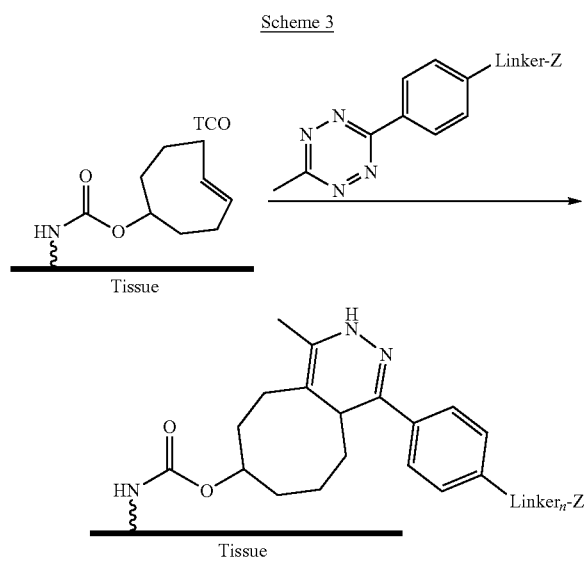

Scheme 4 again illustrates the reaction between an immobilized tissue-click conjugate complex having a malemide reactive functional group, and a second click conjugate of Formula (IV) comprising a reactive thiol group and at least one reporter moiety Z. In some embodiments, the resulting adduct comprises one reporter moiety. In other embodiments, the resulting adduct comprises at least two reporter moieties, such as joined via a scaffold (e.g. a lysine linker or a dendrimer). In some embodiments, the at least one reporter moiety Z is a chromophore. In some embodiments, the at least one chromophore is selected from TAMRA, Cy5, Dabsyl, and Dabcyl. In some embodiments, the adduct comprises two TAMRA chromophores, such as linked via lysine.

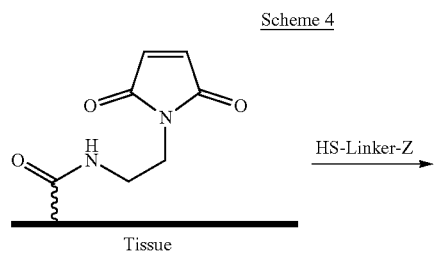

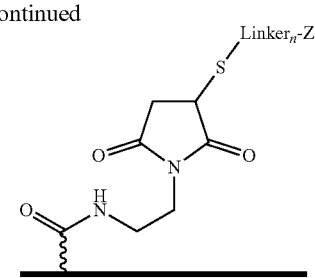

Scheme 5 illustrates the reaction between an immobilized tissue-click conjugate complex having a DBCO reactive functional group, and a second click conjugate of Formula (IV) comprising a reactive 1,3-nitrone group and at least one reporter moiety Z. In some embodiments, the resulting adduct comprises one reporter moiety. In other embodiments, the resulting adduct comprises at least two reporter moieties, such as joined via a scaffold (e.g. a lysine linker or a dendrimer). In some embodiments, the at least one reporter moiety Z is a chromophore. In some embodiments, the at least one chromophore is selected from TAMRA, Cy5, Dabsyl, and Dabcyl. In some embodiments, the adduct comprises two TAMRA chromophores, such as linked via lysine.

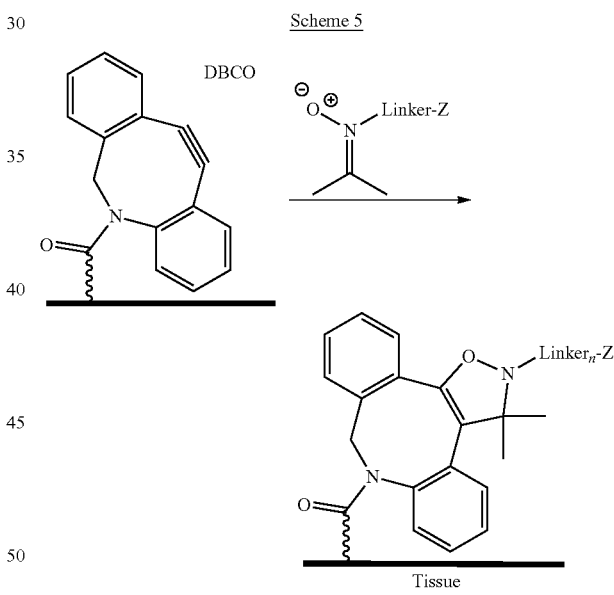

Scheme 6 illustrates the reaction between an immobilized tissue-click conjugate having an aldehyde reactive functional group, and a second click conjugate of Formula (IV) a comprising reactive hydrazine group and at least one reporter moiety Z. In some embodiments, the resulting adduct comprises one reporter moiety. In other embodiments, the resulting adduct comprises at least two reporter moieties, such as joined via a scaffold (e.g. a lysine linker or a dendrimer). In some embodiments, the at least one reporter moiety Z is a chromophore. In some embodiments, the at least one chromophore is selected from TAMRA, Cy5, Dabsyl, and Dabcyl. In some embodiments, the adduct comprises two TAMRA chromophores, such as linked via lysine.

Scheme 6

Scheme 7 illustrates the reaction between an immobilized tissue-click conjugate having an aldehyde reactive functional group, and a second click conjugate of Formula (IV) comprising a reactive hydroxylamine group and at least one reporter moiety Z. In some embodiments, the resulting adduct comprises one reporter moiety. In other embodiments, the resulting adduct comprises at least two reporter moieties, such as joined via a scaffold (e.g. a lysine linker or a dendrimer). In some embodiments, the at least one reporter moiety Z is a chromophore. In some embodiments, the at least one chromophore is selected from TAMRA, Cy5, Dabsyl, and Dabcyl. In some embodiments, the adduct comprises two TAMRA chromophores, such as linked via lysine.

Scheme 7

Scheme 8 illustrates the reaction between an immobilized tissue-click conjugate complex having a DBCO reactive functional group, and a second click conjugate of Formula (IV) comprising a reactive azide group and a chelator as the reporter Z. In some embodiments, a resulting intermediate adduct comprises a chelator which, when a lanthanide is introduced, forms a chelated adduct complex, suitable for detection with MSI.

Scheme 8

Scheme 9A illustrates the reaction between an immobilized tissue-click conjugate complex having a DBCO reactive functional group, and a second click conjugate of Formula (IV) or Formula (V) comprising a reactive azide group coupled to a dendrimer, the dendrimer coupled to two, four, or eight reporter moieties, as shown. Without wishing to be bound by any particular theory, it is believed that the use of dendrimers allows for the incorporation of a plurality of reporters (which may be the same or different), thus providing significant signal amplification.

Scheme 9A
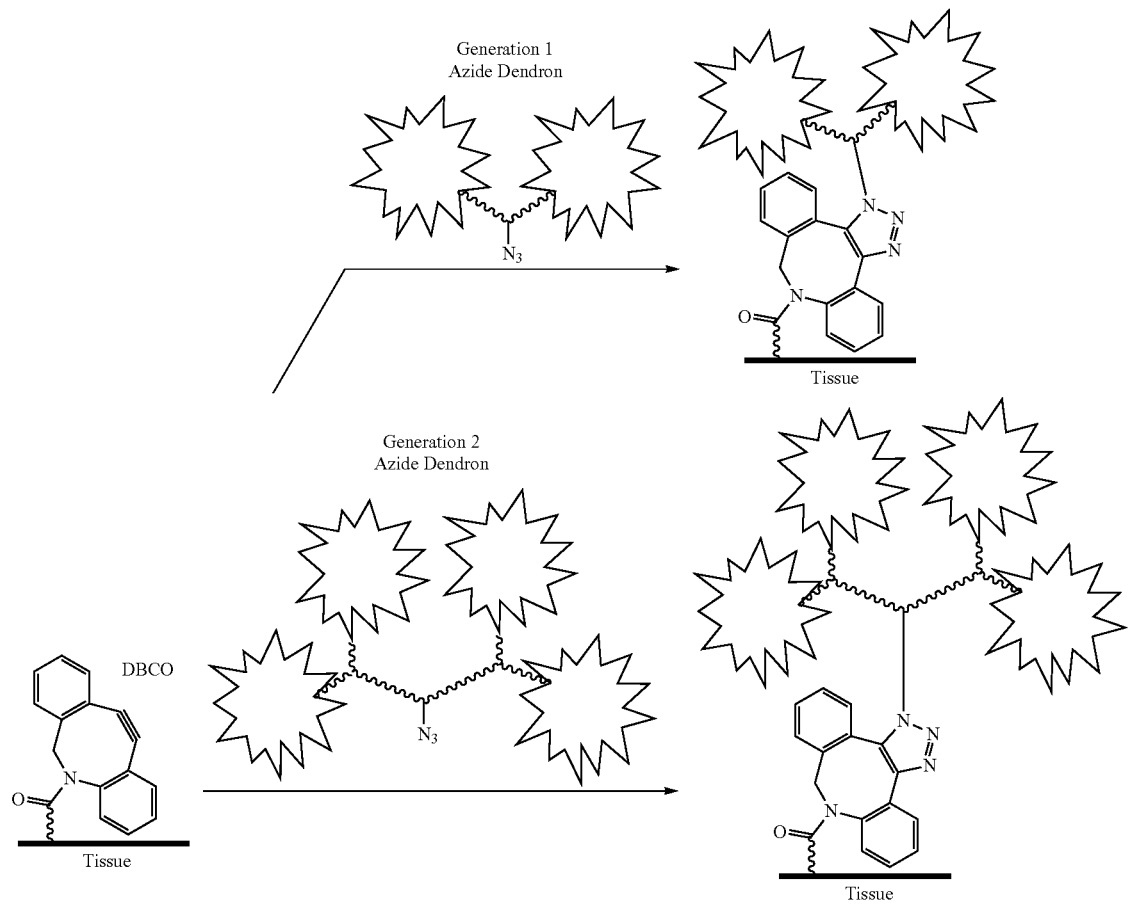
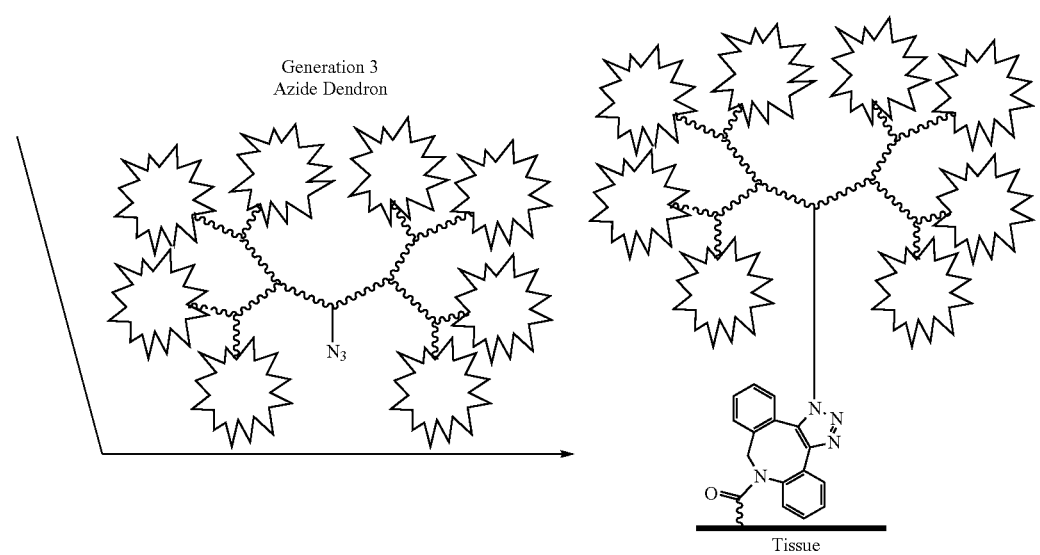
Scheme 9B illustrates the reaction between an immobilized tissue-click conjugate complex having a DBCO reactive functional group, and a second click conjugate of Formula Formula (V) comprising a reactive azide group coupled to a dendrimer (PAMAM), the dendrimer coupled to four reporter moieties Z.

Scheme 9B
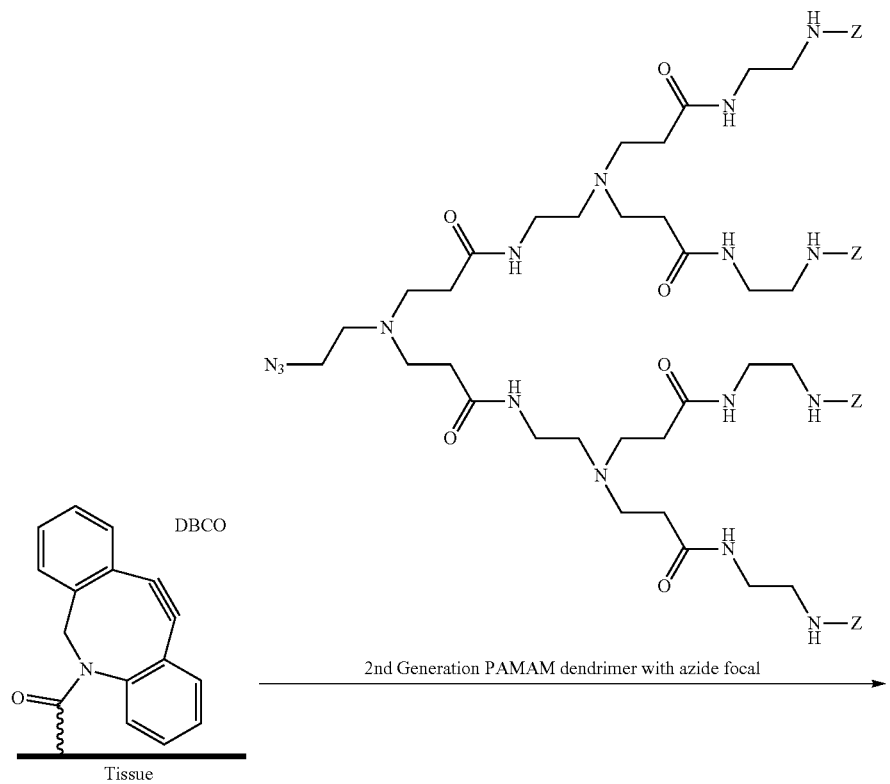
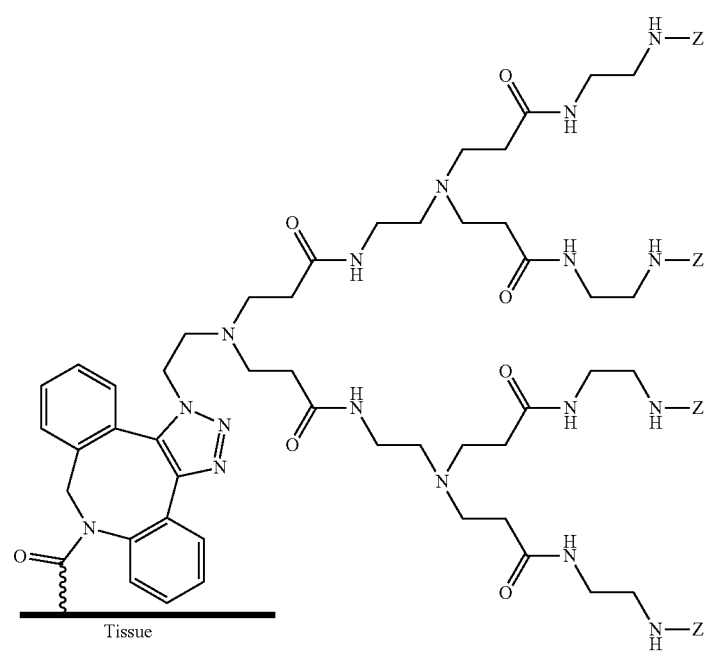

Scheme 10 illustrates the reaction between an immobilized tissue-click conjugate complex having a DBCO reactive functional group, and a second click conjugate of Formula Formula (V) comprising a reactive azide group coupled to a Z group comprising two chromophores, where the two chromophores are linked via a lysine group. While the chromogens are depicted as being the same, the skilled artisan will recognize that the chromogens linked via the lysine group may be different.

Specific examples of immobilized, tissue-click conjugate complexes and their reaction with click conjugates comprising specific reporter moieties are represented in FIGS. 5 and 6.

Methods of Detecting Targets in a Sample Using Click Conjugates

The present disclosure also provides methods of detecting one or more targets within a tissue sample using pairs of any of the click conjugates. While certain disclosed embodi-

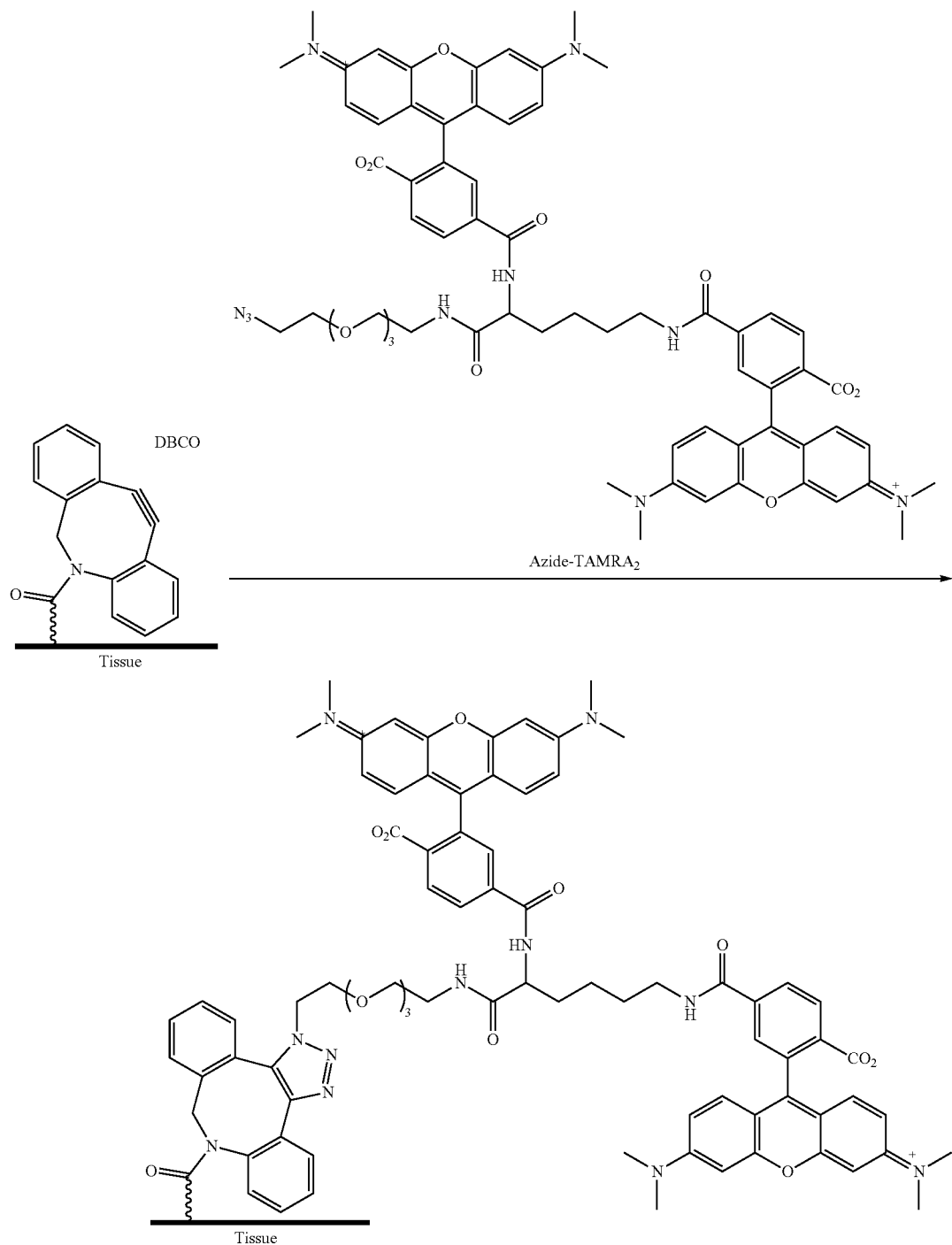

ments, examples, or figures herein may refer to the use of the click conjugates in conjunction in an IHC assay, the skilled artisan will appreciate that the click conjugates may also be used in situ hybridization (ISH) assays, or any combination of IHC and ISH assays. The skilled artisan will also appreciate that the click conjugates may be used in both simplex assays and multiplex assays.

The methods described herein refer to pairs of click conjugates suitable for use in biological assays. In those assays, one member (or "partner") of a particular pair of click conjugates comprises a conjugate of either Formula (II) or (III), and another member of the pair of click conjugates comprises a conjugate of Formula (IV) or Formula (V). In general, a first member of a pair of click conjugates is covalently deposited onto tissue using QMSA or TSA. Then, a second member of the pair of click conjugates comprising a reporter molecule (i.e. chromophore, fluorophore, enzyme, hapten) is applied to the tissue. The "click" reaction between the two "click" partners occurs rapidly, covalently binding the reporter molecules to tissue in the locations dictated by the QMSA or TSA chemistries. Moreover, and as noted herein, the presently disclosed amplification methodology allows for the reporter moiety to be separated from the QMSA or TSA assay conditions, which is believed to enhance signal intensity.

For example, FIGS. 1A, 1B, 2A, and 2B illustrate the reaction between a first member of a pair of click conjugates having a tissue reactive moiety (10, 20) and a target-bound enzyme (11, 21) to form an immobilized tissue-click conjugate complex (13, 23). This first part of the amplification process is similar to that used in QMSA and TSA amplification processes. FIGS. 1A, 1B, 2A, and 2B also illustrate the subsequent reaction between the immobilized tissue-click conjugate (13, 23) complex and a second member of the pair of click conjugates (14, 24), to provide an immobilized tissue-click adduct complex (15, 25) comprising a detectable reporter moiety.

With reference to FIG. 1A, a compound of Formula (II) comprising a reactive functional group (10) is brought into contact with a target-bound enzyme (11) to produce a reactive intermediate (12). In this example, the reactive intermediate, a quinone methide, forms a covalent bond to a nucleophile on or within a tissue sample, thus providing an immobilized tissue-click conjugate complex (13). The immobilized tissue-click conjugate complex may then react with a compound of Formula (IV) (14), provided that the click conjugate 10 and click conjugate 14 possess reactive functional groups that may react with each other to form a covalent bond. The reaction product of immobilized tissue-click conjugate complex 13 and click conjugate 14 produces the immobilized tissue-click adduct complex 15. The tissue-click adduct complex 15 may be detected by virtue of signals transmitted from the linked reporter moiety. In some embodiments, the reporter moiety is at least one chromophore.

Figure 1B:
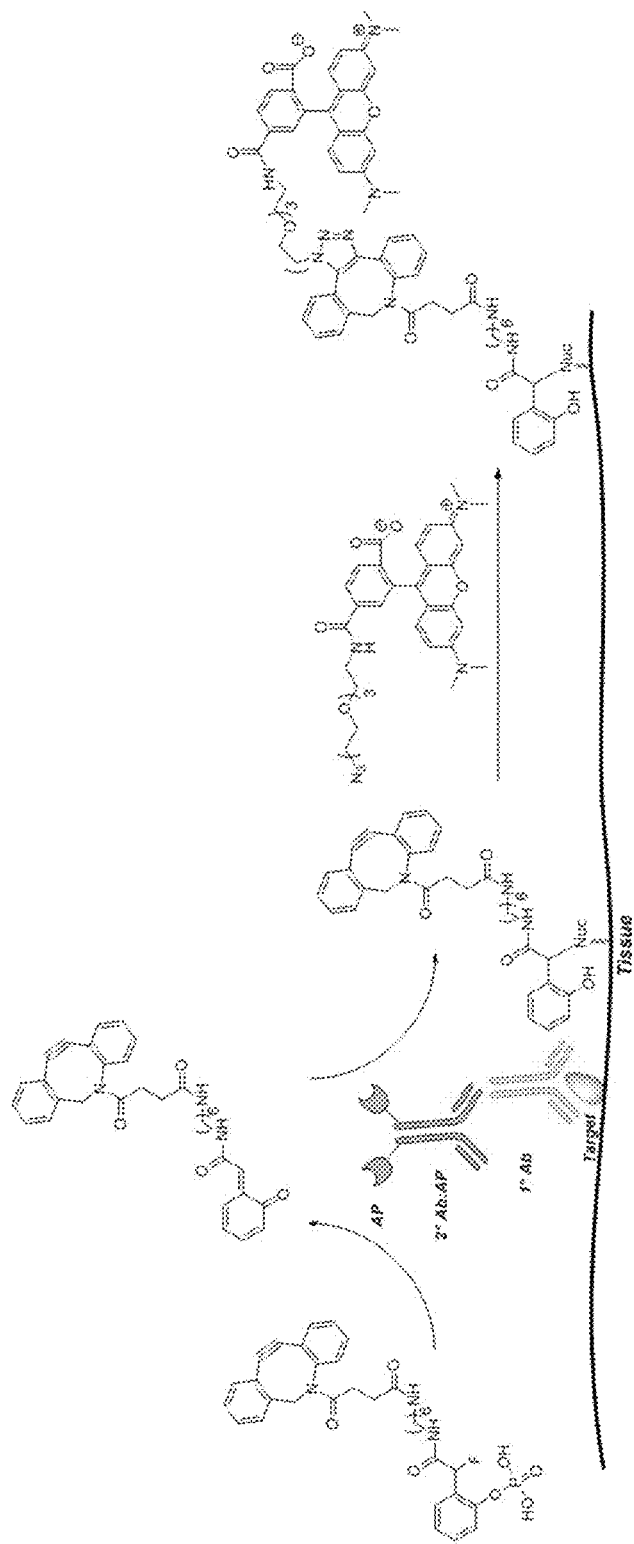
FIG. 1B sets forth an additional reaction scheme illustrating the reaction between a click conjugate comprising a quinone methide precursor moiety and a tissue-bound enzyme; followed by reaction between the resulting tissue-click conjugate complex and a second click conjugate to form a tissue-click conjugate adduct.

FIG. 1B illustrates the reaction between a specific compound of Formula (II) having a quinone methide precursor moiety linked to a DBCO reactive functional group and a target-bound enzyme to produce the reactive quinone methide intermediate, followed by coupling of that reactive intermediate with a nucleophile on or within the biological sample. More specifically, alkaline phosphatase recognizes and cleaves the phosphate group from the illustrated quinone methide precursor portion of the click conjugate, resulting in ejection of the leaving group, and formation of the respective quinone methide intermediate. The immobilized tissue-click conjugate may then react with a compound of Formula (IV), such as one comprising an azide group and a chromophore, as illustrated. The resulting product is a tissue-click adduct complex having the depicted detectable chromophore.

Figure 2A:
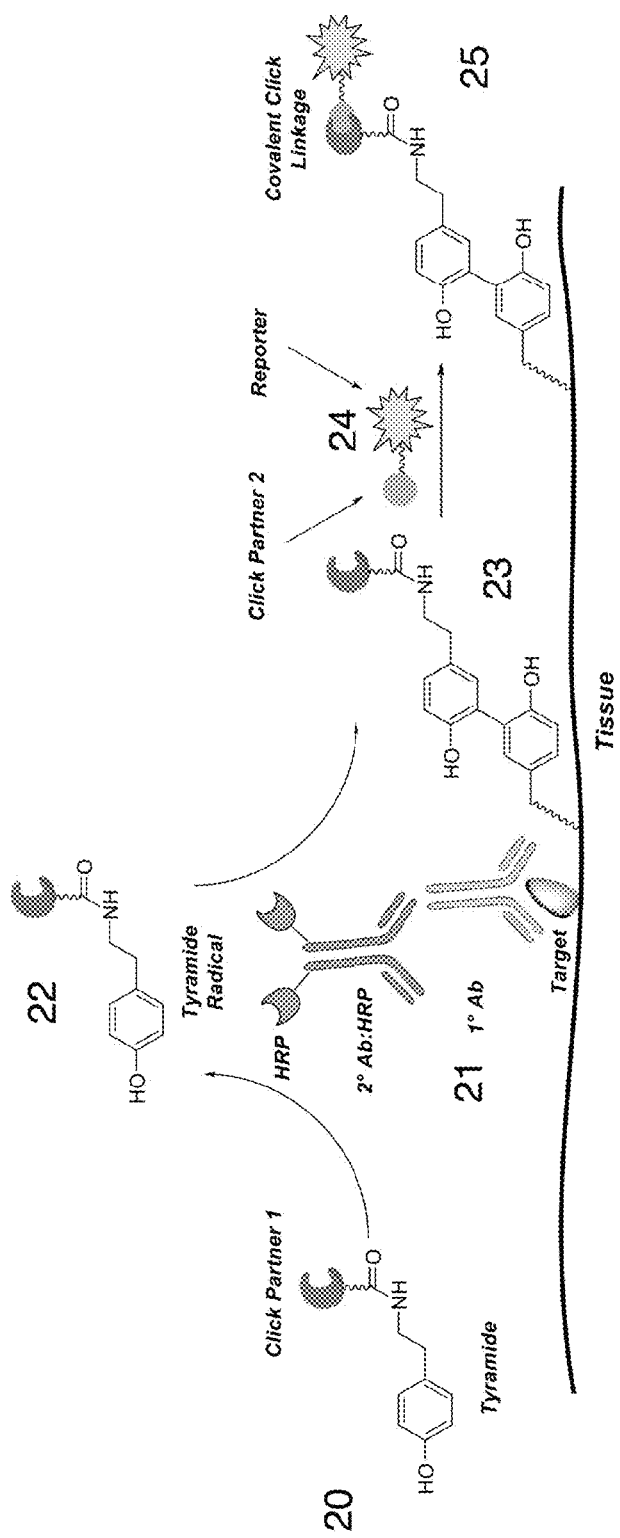
FIG. 2A sets forth a reaction scheme illustrating the reaction between a click conjugate comprising a tyramide moiety and a tissue-bound enzyme; followed by reaction between the resulting tissue-click conjugate complex and a second click conjugate to form a tissue-click conjugate adduct.

Similarly, and with reference to FIG. 2A, a compound of Formula (III) comprising a reactive functional group (20) is brought into contact with a target-bound enzyme (21), to produce a reactive intermediate (22), namely a tyramide radical species (or derivative thereof). The tyramide radical intermediate may then form a covalent bond to a tissue sample, thus providing an immobilized tissue-click conjugate complex (23). The immobilized tissue-click conjugate complex may then react with a compound of Formula (IV) (24), provided that click conjugates 20 and 24 possess reactive functional groups that may react with each other to form a covalent bond. The reaction product of immobilized tissue-click conjugate complex 23 and click conjugate 24 produces the tissue-click adduct complex 25.

Figure 2B:
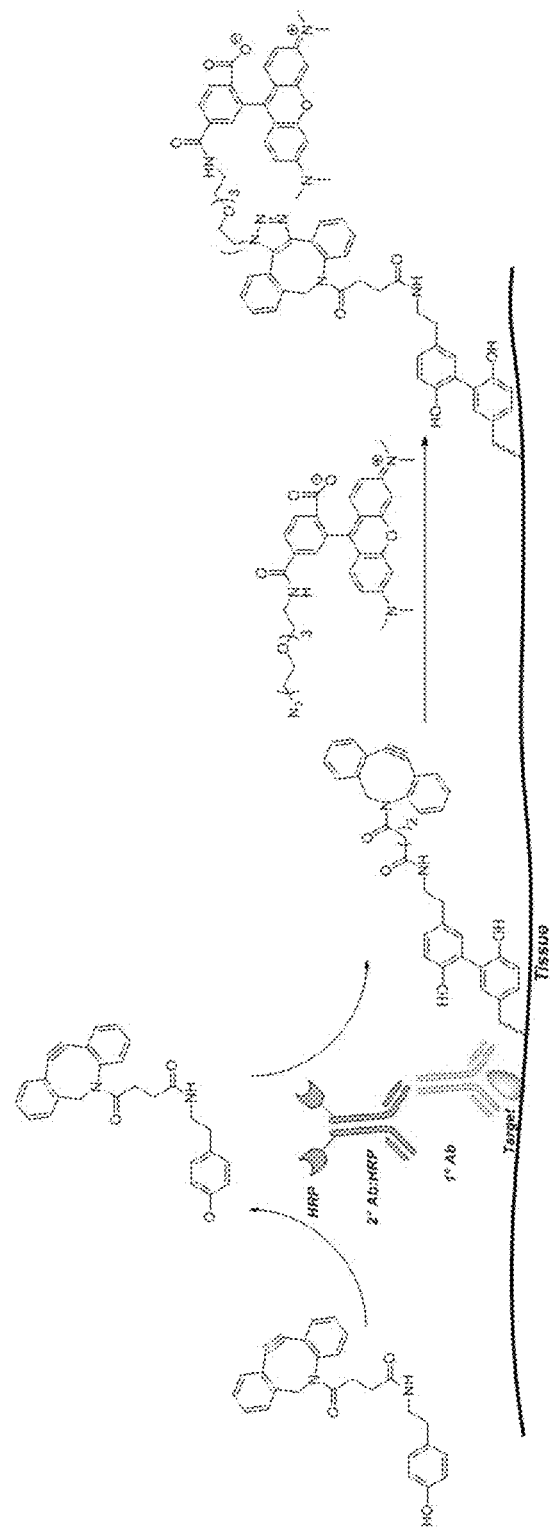
FIG. 2B sets forth an additional reaction scheme illustrating the reaction between a click conjugate comprising a tyramide moiety and a tissue-bound enzyme; followed by reaction between the resulting tissue-click conjugate complex and a second click conjugate to form a tissue-click conjugate adduct.

FIG. 2B illustrates the reaction between a specific compound of Formula (III), namely a compound having tyramide moiety linked to a DBCO reactive functional group. FIG. 4 also illustrates a target-bound enzyme to produce the reactive tyramide radical intermediate, followed by coupling of that intermediate with the biological sample to form an immobilized tissue-click conjugate complex. The immobilized tissue-click conjugate complex may then react with a compound of Formula (IV), such as one comprising an azide group and a chromophore, as illustrated. The resulting product is a tissue-click adduct complex (25) having a detectable chromophore.

In some embodiments, the methods of detecting targets in a biological sample comprise the following steps. First, the biological sample is contact with a first detection probe specific to a first target. The first detection probe may be a primary antibody or a nucleic acid probe. Subsequently, the sample is contacted with a first labeling conjugate, the first labeling conjugate comprising a first enzyme. In some embodiments, the first labeling conjugate is a secondary antibody specific for either the primary antibody or to a label conjugated to the nucleic acid probe. Next, the biological sample is contacted with a first member of a pair of click conjugates, the first member of the pair of click conjugates having the structure of any of the compounds of Formulas (II) or (III). As described herein, the first enzyme cleaves the first member of the pair of click conjugates, thereby converting the first member into a reactive intermediate which covalently binds to the biological sample proximally to or directly on the first target. Next, a second member of the pair of click conjugates is introduced, the second member of the pair of click conjugates comprising a first reporter moiety and a second reactive functional group, where the second reactive functional group of the second member of the first pair of click conjugates is capable of reacting with the first reactive functional group of the first member of the pair of click conjugates. The second member of the pair of click conjugates may have the structure as provided in Formula (IV). Finally, signals from the first reporter moiety are detected.

Figure 15:
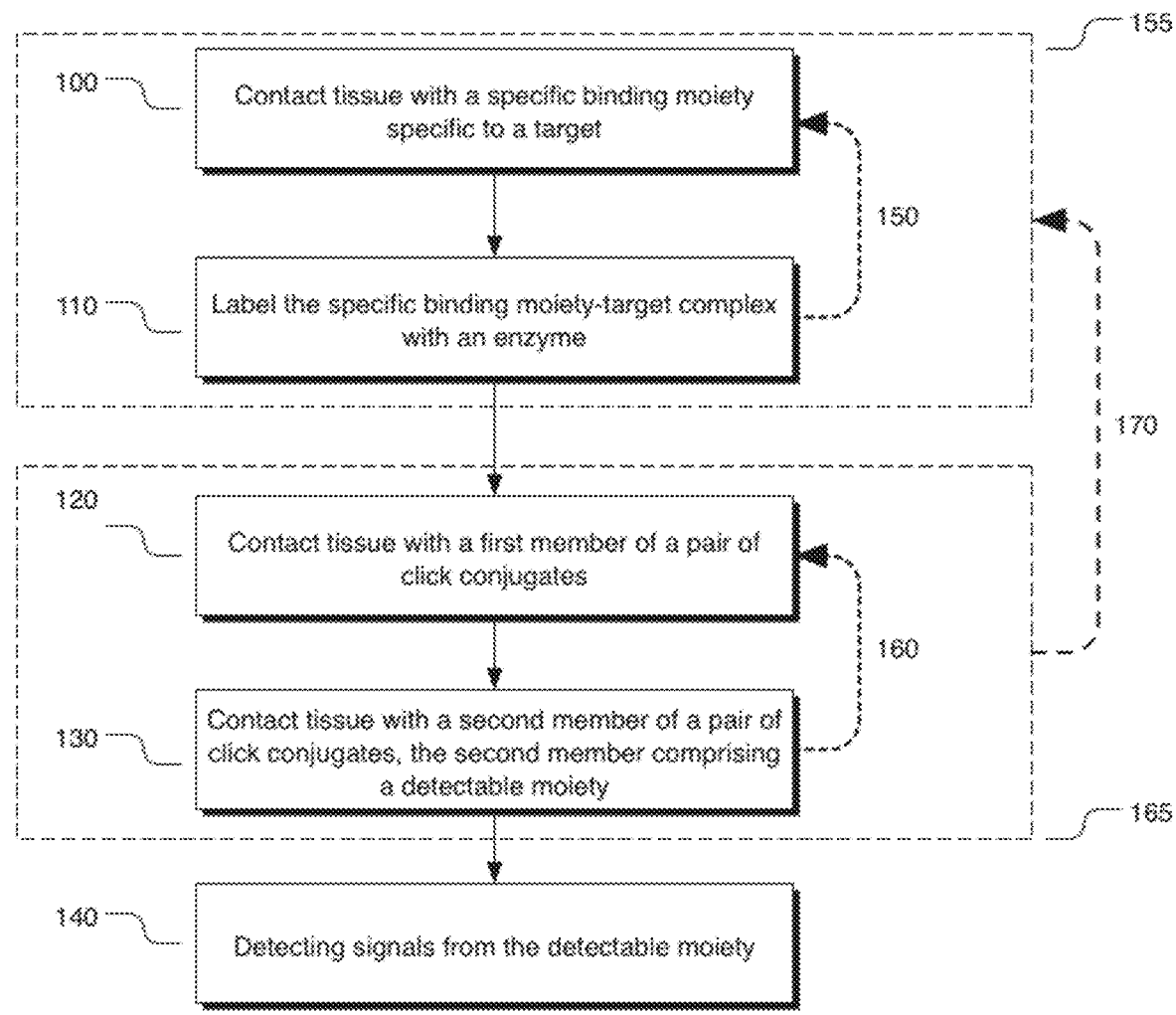
FIG. 15 sets forth a flowchart depicting the steps of detecting targets within a biological sample utilizing an amplification protocol utilizing the click conjugates of the present disclosure.

With reference to FIG. 15, the method of detecting one or more targets within a tissue sample using the click conjugates described herein can generally be divided into two stages. In a first stage, each target within the tissue sample is labeled with an enzyme (see block 155 and the steps contained therein). In a second stage, a reporter moiety is deposited directly on or proximal to each of the targets (see block 165 and the steps contained therein), wherein the reporter moiety is deposited using a pair of the click conjugates enumerated herein (e.g. a first conjugate comprising a tissue reactive moiety portion and having the structure of any of Formulas (II) and (III), and a second conjugate comprising a reporter moiety and having the structure of Formula (IV)). The skilled artisan will appreciate that each of these general steps may be repeated in a multiplex assay (step 170) to detect a plurality of different targets within the tissue sample. Each of these steps will be described in further detail herein.

In some embodiments, and prior to the introduction of any detection reagents, the tissue samples are pre-treated with an enzyme inactivation composition to substantially or completely inactivate endogenous peroxidase activity. For example, where cells or tissues contain endogenous peroxidase, use of a HRP conjugated antibody may result in high, non-specific background staining. This non-specific background can be reduced by pre-treatment of the sample with an enzyme inactivation composition as disclosed herein. In some embodiments, the samples are pre-treated with hydrogen peroxide only (about 1% to about 3% by weight of an appropriate pre-treatment solution) to reduce endogenous peroxidase activity.

Referring again to FIG. 15, a tissue sample containing one or more targets is contacted with a first specific binding moiety specific to a first target to provide a first specific binding moiety-target complex (step 100). In some embodiments, the first specific binding moiety is a primary antibody or antibody conjugate (e.g. an unmodified antibody or an antibody conjugated to a detectable label, such as a hapten). In other embodiments, the first specific binding moiety is a nucleic acid probe conjugated to a detectable label, such as a hapten.

The first specific binding moiety-target complex is subsequently labeled with a first enzyme through the first specific binding moiety (step 110). In some embodiments, the labeling of the target complex may be achieved with a secondary antibody, the secondary antibody being an anti-antibody antibody (e.g. one that is specific to a primary antibody, namely an anti-antibody antibody) or an anti-label antibody (e.g. an anti-label antibody or an anti-hapten antibody), the secondary antibody being conjugated to an enzyme (e.g. HRP, AP, etc.).

The tissue sample is then contacted with a first member of a first pair of click conjugates, where the first member of the first pair of click conjugates comprises a tissue reactive moiety and a first reactive functional group (step 120). The first member of the first pair of click conjugates may have the formula as provided in any of Formulas (II) or (III). The first member of the first pair of click conjugates interacts/reacts with the first enzyme to form a reactive species or intermediate, where the reactive species or intermediate is capable of forming a covalent bond directly or indirectly with the tissue sample either directly on or proximal to the first target. Next, a second member of the first pair of click conjugates is introduced (step 130), the second member of the first pair of click conjugates comprising a first reporter moiety and a second reactive functional group, where the second reactive functional group of the second member of the first pair of click conjugates is capable of reacting with the first reactive functional group of the first member of the first pair of click conjugates. The second member of the first pair of click conjugates may have the structure as provided in Formula (IV). Finally, signals from the first reporter moiety are detected (e.g. brightfield microscopy) (step 140). In some embodiments, the first reporter moiety is a chromophore. In some embodiments, the second member of the first pair of click conjugates is conjugated to at least two chromophores, and where the second member of the first pair of click conjugates has the structure of Formula (V).

The aforementioned process may be repeated for any number of targets within the sample (step 170). In some embodiments, an enzyme inactivation composition may be introduced to substantially or completely inactivate any enzymes from any upstream steps. Then, the tissue sample may be contacted with a second specific binding moiety specific to a second target to provide a second specific binding moiety target complex (step 100). The second specific binding moiety target complex is subsequently labeled with a second enzyme through the second specific binding moiety (step 110). The tissue sample is then contacted with a first member of a second pair of click conjugates, where the first member of the second pair of click conjugates comprises either a quinone methide precursor or a tyramide moiety and a first reactive functional group (step 120). The first member of the second pair of click conjugates interacts with the second enzyme to form a reactive species, where the reactive species is capable of forming a covalent bond either directly on or proximal to the second target. The first member of the first pair of click conjugates may have the formula as provided in any of Formulas (II) or (III). Next, a second member of the second pair of click conjugates is introduced (step 130), the second member of the second pair of click conjugates comprising a second reporter moiety and a second reactive functional group, where the second reactive functional group of the second member of the second pair of click conjugates is capable of reacting with the first reactive functional group of the first member of the second pair of click conjugates. The second member of the second pair of click conjugates may have the structure as provided in Formula (IV). The second reporter moiety is then detected (step 140). The process may be repeated for third, fourth, or nth targets within the tissue sample (step 170).

The skilled artisan will appreciate that the steps illustrated in FIG. 15 may be performed sequentially (or serially) or substantially simultaneously. For example, the tissue sample may be contacted simultaneously at step 100 with two specific binding moieties (where each specific binding moiety is specific to a particular target); and then each specific binding moiety-target complex simultaneously labeled with different enzymes at step 110. In these embodiments, either the reagents used at either step 100 or 110 may be supplied as a "pool" or "cocktail" of reagents. Alternatively, a first specific binding moiety may be deposited (step 100) followed by labeling of that first specific binding moiety-target complex (step 110). Steps 100 and 110 may be serially repeated any number of times (step 150) prior to the introduction of any click conjugates.

Subsequently, a tissue sample having a plurality of enzyme labeled target complexes (steps 100, 110, and 150) may then be contacted with a plurality of click conjugates. First members of pairs of click conjugates may be added simultaneously at step 120 prior to the simultaneous introduction of second members of pairs of click conjugates at step 130. Alternatively, a first member of a first pair of click conjugates may be introduced followed by the introduction of a second member of a first pair of click conjugates, and the sequential introduction of first and second members of pairs of click conjugates may be repeated any number of times (step 160) to introduce a reporter moiety for each of the labeled target complexes.

Advantageously, for the methods just described, the first enzyme and the second enzyme are different enzymes. For example, the first enzyme can be a phosphatase or phosphodiesterase, and the second enzyme can be a peroxidase. In certain embodiments, the first enzyme is alkaline phosphatase and the second enzyme is horseradish peroxidase. Also advantageously, the first enzyme does not interact with the first member of a second pair of click conjugates to deposit a reactive intermediate derived from first member of the second pair of click conjugates proximally to the first target.

Automation

The assays and methods of the present disclosure may be automated and may be combined with a specimen processing apparatus. The specimen processing apparatus can be an automated apparatus, such as the BENCHMARK XT instrument, the SYMPHONY instrument, the BENCHMARK ULTRA instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Alternatively, specimens can be manually processed.

The specimen processing apparatus can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized with the specimen processing apparatus using appropriate deparaffinizing fluid(s). After the waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The specimen processing apparatus can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated nucleic acid or an isolated synthetic oligonucleotide, attached to a detectable label. Labels can include radioactive isotopes, enzyme substrates, co-factors, ligands, chemiluminescent or fluorescent agents, haptens, and enzymes.

After the specimens are processed, a user can transport specimen-bearing slides to the imaging apparatus. The imaging apparatus used here is a brightfield imager slide scanner. One brightfield imager is the iScan Coreo™ brightfield scanner sold by Ventana Medical Systems, Inc. In automated embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Application Publication No. 2014/0178169, filed on Feb. 3, 2014, entitled IMAGING SYSTEMS, CASSETTES, AND METHODS OF USING THE SAME. International Patent Application No. PCT/US2010/002772 and U.S. Patent Application Publication No. 2014/0178169 are incorporated by reference in their entities. In other embodiments, the imaging apparatus includes a digital camera coupled to a microscope.

Counterstaining

Counterstaining is a method of post-treating the samples after they have already been stained with agents to detect one or more targets, such that their structures can be more readily visualized under a microscope. For example, a counterstain is optionally used prior to coverslipping to render the immunohistochemical stain more distinct. Counterstains differ in color from a primary stain. Numerous counterstains are well known, such as hematoxylin, eosin, methyl green, methylene blue, Giemsa, Alcian blue, and Nuclear Fast Red. DAPI (4',6-diamidino-2-phenylindole) is a fluorescent stain that may be used.

In some examples, more than one stain can be mixed together to produce the counterstain. This provides flexibility and the ability to choose stains. For example, a first stain, can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain.

Detection and/or Imaging

Certain aspects, or all, of the disclosed embodiments can be automated, and facilitated by computer analysis and/or image analysis system. In some applications, precise color or fluorescence ratios are measured. In some embodiments, light microscopy is utilized for image analysis. Certain disclosed embodiments involve acquiring digital images. This can be done by coupling a digital camera to a microscope. Digital images obtained of stained samples are analyzed using image analysis software. Color or fluorescence can be measured in several different ways. For example, color can be measured as red, blue, and green values; hue, saturation, and intensity values; and/or by measuring a specific wavelength or range of wavelengths using a spectral imaging camera. The samples also can be evaluated qualitatively and semi-quantitatively. Qualitative assessment includes assessing the staining intensity, identifying the positively-staining cells and the intracellular compartments involved in staining, and evaluating the overall sample or slide quality. Separate evaluations are performed on the test samples and this analysis can include a comparison to known average values to determine if the samples represent an abnormal state.

Kits

In some embodiments, the click conjugates may be utilized as part of a "detection kit." In some embodiments, the detection kits comprise at least a first click conjugate in a first container and a second click conjugate in a second container. The first click conjugate is a first member of a pair of click conjugates having a first reactive functional group; and the second click conjugate is a second member of a pair of click conjugates having a second reactive functional group, wherein the first and second reactive functional groups are capable of reacting with each other to form a covalent bond. In some embodiments, the first click conjugate is selected from a compound having the structure of any of Formulas (II) or (III). In some embodiments, the second click conjugate is selected from a compound having the structure of Formula (IV) or Formula (V).

The detection kits may also comprise other reagents including specific binding moieties and secondary antibodies specific to the specific binding moieties, the secondary antibodies conjugated to a detectable label. Of course, any kit may include other agents, including buffers; counterstaining agents; enzyme inactivation compositions; deparaffinization solutions, etc. as needed for manual or automated target detection. The kit may also include instructions for using any of the components of the kit, including methods of applying the kit components to a tissue sample to effect detection of one or more targets therein.

Samples and Targets

Samples include biological components and generally are suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples for use in the embodiments of the method and with the composition disclosed herein, such as a tissue or other biological sample, can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc.

Samples can include multiple targets that can be specifically bound by a probe or reporter molecule. The targets can be nucleic acid sequences or proteins. Throughout this disclosure when reference is made to a target protein it is understood that the nucleic acid sequences associated with that protein can also be used as a target. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

A target nucleic acid sequence can vary substantially in size. Without limitation, the nucleic acid sequence can have a variable number of nucleic acid residues. For example, a target nucleic acid sequence can have at least about 10 nucleic acid residues, or at least about 20, 30, 50, 100, 150, 500, 1000 residues. Similarly, a target polypeptide can vary substantially in size. Without limitation, the target polypeptide will include at least one epitope that binds to a peptide specific antibody, or fragment thereof. In some embodiments that polypeptide can include at least two epitopes that bind to a peptide specific antibody, or fragment thereof.

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample.

Oncogenes are known to be responsible for several human malignancies. For example, chromosomal rearrangements involving the SYT gene located in the breakpoint region of chromosome 18q11.2 are common among synovial sarcoma soft tissue tumors. The t(18q11.2) translocation can be identified, for example, using probes with different labels: the first probe includes FPC nucleic acid molecules generated from a target nucleic acid sequence that extends distally from the SYT gene, and the second probe includes FPC nucleic acid generated from a target nucleic acid sequence that extends 3' or proximal to the SYT gene. When probes corresponding to these target nucleic acid sequences (e.g., genomic target nucleic acid sequences) are used in an in situ hybridization procedure, normal cells, which lack a t(18q11.2) in the SYT gene region, exhibit two fusion (generated by the two labels in close proximity) signals, reflecting the two intact copies of SYT. Abnormal cells with a t(18q11.2) exhibit a single fusion signal.

In other examples, a target protein produced from a nucleic acid sequence (e.g., genomic target nucleic acid sequence) is selected that is a tumor suppressor gene that is deleted (lost) in malignant cells. For example, the p16 region (including D9S1749, D9S1747, p16(INK4A), p14(ARF), D9S 1748, p 15(INK4B), and D9S 1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC-000007, nucleotides 55054219-55242525), the C-MYC gene (8q24.21; e.g., GENBANK™ Accession No. NC-000008, nucleotides 128817498-128822856), D5S271 (5p15.2), lipoprotein lipase (LPL) gene (8p22; e.g., GENBANK™ Accession No. NC-000008, nucleotides 19841058-19869049), RB1 (13q14; e.g., GENBANK™ Accession No. NC-000013, nucleotides 47775912-47954023), p53 (17p13.1; e.g., GENBANK™ Accession No. NC-000017, complement, nucleotides 7512464-7531642)), N-MYC (2p24; e.g., GEN- BANK™ Accession No. NC-000002, complement, nucleotides 151835231-151854620), CHOP (12q13; e.g., GENBANK™ Accession No. NC-000012, complement, nucleotides 56196638-56200567), FUS (16p11.2; e.g., GENBANK™ Accession No. NC-000016, nucleotides 31098954-31110601), FKHR (13p14; e.g., GENBANK™ Accession No. NC-000013, complement, nucleotides 40027817-40138734), as well as, for example: ALK (2p23; e.g., GENBANK™ Accession No. NC-000002, complement, nucleotides 29269144-29997936), Ig heavy chain, CCND1 (11q13; e.g., GENBANK™ Accession No. NC-000011, nucleotides 69165054.69178423), BCL2 (18q21.3; e.g., GENBANK™ Accession No. NC-000018, complement, nucleotides 58941559-59137593), BCL6 (3q27; e.g., GENBANK™ Accession No. NC-000003, complement, nucleotides 188921859-188946169), MALF 1, AP 1 (lp32-p31; e.g., GENBANK™ Accession No. NC-000001, complement, nucleotides 59019051-59022373), TOP2A (17q21-q22; e.g., GENBANK™ Accession No. NC-000017, complement, nucleotides 35798321-35827695), TMPRSS (21q22.3; e.g., GENBANK™ Accession No. NC-000021, complement, nucleotides 41758351-41801948), ERG (21q22.3; e.g., GENBANK™ Accession No. NC-000021, complement, nucleotides 38675671-38955488); ETV1 (7p21.3; e.g., GENBANK™ Accession No. NC-000007, complement, nucleotides 13897379-13995289), EWS (22q12.2; e.g., GENBANK™ Accession No. NC-000022, nucleotides 27994271-28026505); FLI1 (11q24.1-q24.3; e.g., GENBANK™ Accession No. NC-000011, nucleotides 128069199-128187521), PAX3 (2q35-q37; e.g., GENBANK™ Accession No. NC-000002, complement, nucleotides 222772851-222871944), PAX7 (lp36.2-p36.12; e.g., GENBANK™ Accession No. NC-000001, nucleotides 18830087-18935219), PTEN (10q23.3; e.g., GENBANK™ Accession No. NC-000010, nucleotides 89613175-89716382), AKT2 (19q13.1-q13.2; e.g., GENBANK™ Accession No. NC-000019, complement, nucleotides 45431556-45483036), MYCL1 (1p34.2; e.g., GENBANK™ Accession No. NC-000001, complement, nucleotides 40133685-40140274), REL (2p13-p12; e.g., GENBANK™ Accession No. NC-000002, nucleotides 60962256-61003682) and CSF1R (5q33-q35; e.g., GENBANK™ Accession No. NC-000005, complement, nucleotides 149413051-149473128).

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the target peptide, polypeptide or protein can be selected from the genome of an oncogenic or pathogenic virus, a bacterium or an intracellular parasite (such as *Plasmodium falciparum* and other *Plasmodium* species, *Leishmania* (sp.), *Cryptosporidium parvum*, *Entamoeba histolytica*, and *Giardia lamblia*, as well as *Toxoplasma, Eimeria, Theileria*, and *Babesia* species).

In some examples, the target protein is produced from a nucleic acid sequence (e.g., genomic target nucleic acid sequence) from a viral genome. Exemplary viruses and corresponding genomic sequences (GENBANK™ RefSeq Accession No. in parentheses) include human adenovirus A (NC-001460), human adenovirus B (NC-004001), human adenovirus C(NC-001405), human adenovirus D (NC-002067), human adenovirus E (NC-003266), human adenovirus F (NC-001454), human astrovirus (NC-001943), human BK polyomavirus (V01109; GI:60851) human bocavirus (NC-007455), human coronavirus 229E (NC-002645), human coronavirus HKU1 (NC-006577), human coronavirus NL63 (NC-005831), human coronavirus OC43 (NC-005147), human enterovirus A (NC-001612), human enterovirus B (NC-001472), human enterovirus C(NC-001428), human enterovirus D (NC-001430), human erythrovirus V9 (NC-004295), human foamy virus (NC-001736), human herpesvirus 1 (Herpes simplex virus type 1) (NC-001806), human herpesvirus 2 (Herpes simplex virus type 2) (NC-001798), human herpesvirus 3 (Varicella zoster virus) (NC-001348), human herpesvirus 4 type 1 (Epstein-Barr virus type 1) (NC-007605), human herpesvirus 4 type 2 (Epstein-Barr virus type 2) (NC-009334), human herpesvirus 5 strain AD 169 (NC-001347), human herpesvirus 5 strain Merlin Strain (NC-006273), human herpesvirus 6A (NC-001664), human herpesvirus 6B (NC-000898), human herpesvirus 7 (NC-001716), human herpesvirus 8 type M (NC-003409), human herpesvirus 8 type P (NC-009333), human immunodeficiency virus 1 (NC-001802), human immunodeficiency virus 2 (NC-001722), human metapneumovirus (NC-004148), human papillomavirus-1 (NC-001356), human papillomavirus-18 (NC-001357), human papillomavirus-2 (NC-001352), human papillomavirus-54 (NC-001676), human papillomavirus-61 (NC-001694), human papillomavirus-cand90 (NC-004104), human papillomavirus RTRX7 (NC-004761), human papillomavirus type 10 (NC-001576), human papillomavirus type 101 (NC-008189), human papillomavirus type 103 (NC-008188), human papillomavirus type 107 (NC-009239), human papillomavirus type 16 (NC-001526), human papillomavirus type 24 (NC-001683), human papillomavirus type 26 (NC-001583), human papillomavirus type 32 (NC-001586), human papillomavirus type 34 (NC-001587), human papillomavirus type 4 (NC-001457), human papillomavirus type 41 (NC-001354), human papillomavirus type 48 (NC-001690), human papillomavirus type 49 (NC-001591), human papillomavirus type 5 (NC-001531), human papillomavirus type 50 (NC-001691), human papillomavirus type 53 (NC-001593), human papillomavirus type 60 (NC-001693), human papillomavirus type 63 (NC-001458), human papillomavirus type 6b (NC-001355), human papillomavirus type 7 (NC-001595), human papillomavirus type 71 (NC-002644), human papillomavirus type 9 (NC-001596), human papillomavirus type 92 (NC-004500), human papillomavirus type 96 (NC-005134), human parainfluenza virus 1 (NC-003461), human parainfluenza virus 2 (NC-003443), human parainfluenza virus 3 (NC-001796), human parechovirus (NC-001897), human parvovirus 4 (NC-007018), human parvovirus B19 (NC-000883), human respiratory syncytial virus (NC-001781), human rhinovirus A (NC-001617), human rhinovirus B (NC-001490), human spumaretrovirus (NC-001795), human T-lymphotropic virus 1 (NC-001436), human T-lymphotropic virus 2 (NC-001488).

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

EXAMPLES

The non-limiting examples presented herein each incorporate the use of at least one pair of click conjugates. Applicants submit that the click conjugates disclosed herein are suitable for use in IHC assays, including multiplex IHC assays, and ISH assays, as demonstrated in the following examples.

General Immunohistochemistry (IHC) Protocol(s)

All IHC staining experiments were carried out on a BenchMark XT automated tissue staining platform and the reagents used in these protocols were from Ventana Medical Systems, Inc. (Tucson, Ariz., USA; "Ventana") unless otherwise specified. Polyclonal goat anti-rabbit antibodies, polyclonal goat anti-mouse antibodies, horseradish peroxidase (HRP) and alkaline phosphatase (AP) were obtained from Roche Diagnostics (Mannheim, Germany).

The following common steps were performed: (1) deparaffinization with EZ Prep detergent solution (Ventana Medical Systems, Inc. (VMSI), #950-101) (75° C.; 20 minutes); (2) washing with Reaction Buffer (VMSI, #950-300); (3) antigen retrieval in Cell Conditioning 1 (VMSI #950-124) (100° C.; time dependent on antigen of interest); (4) washing (same as step 2); (5) for protocols with subsequent HRP detection steps endogenous peroxidase was inactivated using iVIEW inhibitor (VMSI, E253-2187) (37° C.; 4 minutes); (6) washing (same as step 2); (7) primary antibody incubation (anti-target antibody) was performed at 37° C. for a time dependent on primary antibody ranging from 8-32 minutes; (8) washing (same as step 2); and (9) secondary antibody incubation with a goat polyclonal anti-species antibody conjugated to an enzyme (HRP or AP, 37° C.; 8-12 minutes). All subsequent reagent incubation steps were separated by washing as in step (2). The targets were detected as described in examples 1-6.

Example 1: "Click" Amplification with Compounds of Formula (II)

Figure 7A:
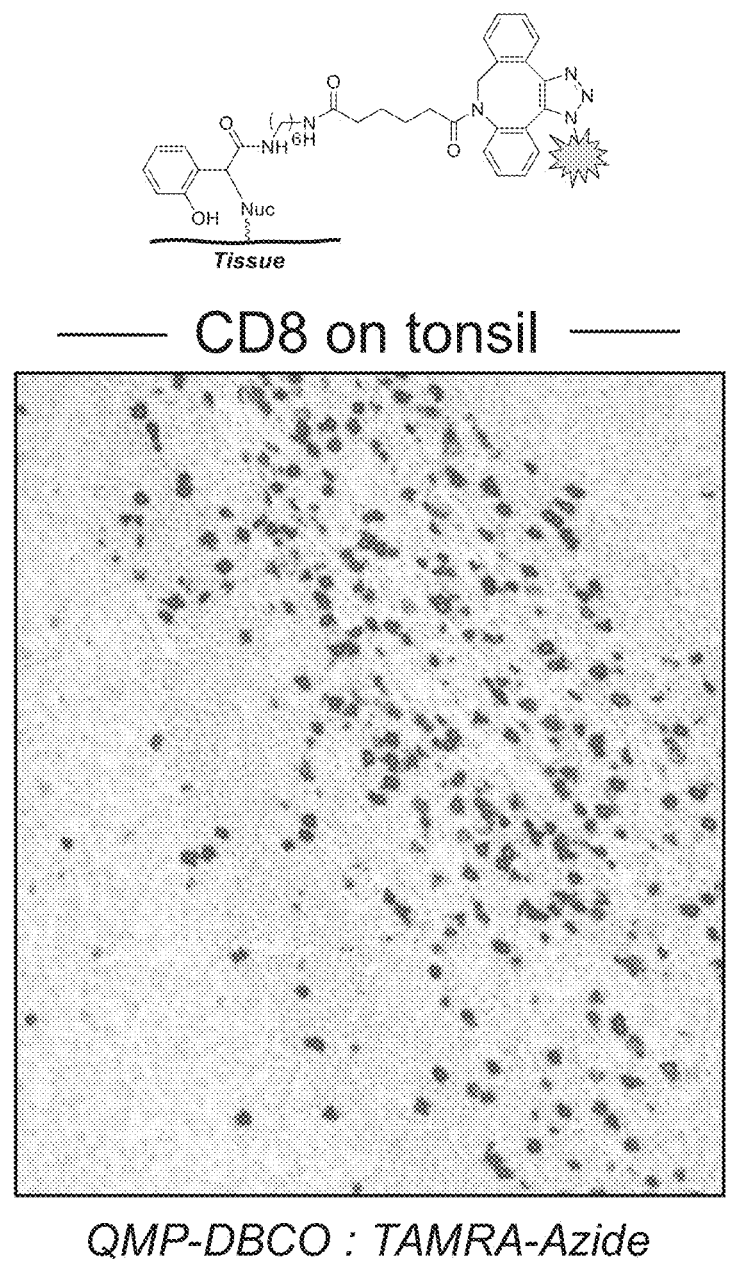
FIG. 7A illustrates staining of tonsil samples with a QMSA conjugate.
Figure 7B:
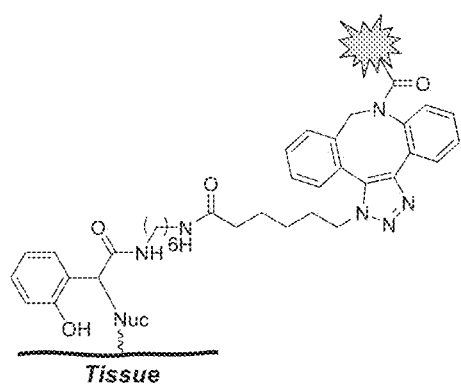
FIG. 7B is an additional illustration of staining of tonsil samples with a QMSA conjugate.
Figure 7B:
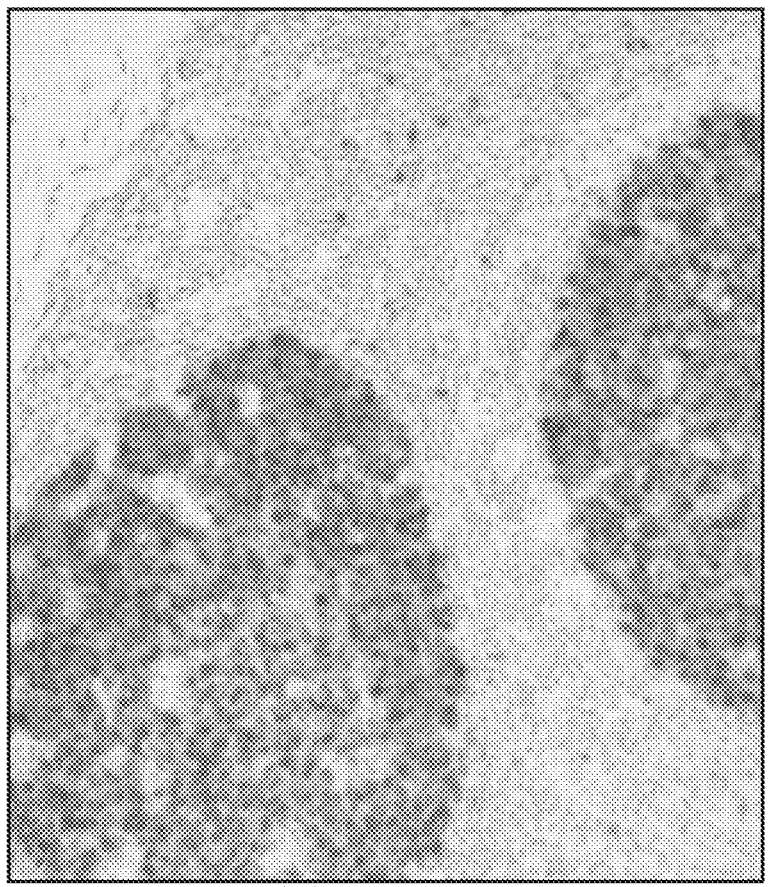
Figure 7C:
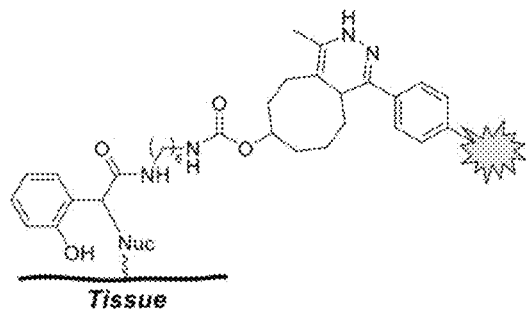
FIG. 7C is an additional illustration of staining of tonsil samples with a QMSA conjugate.
Figure 7C:
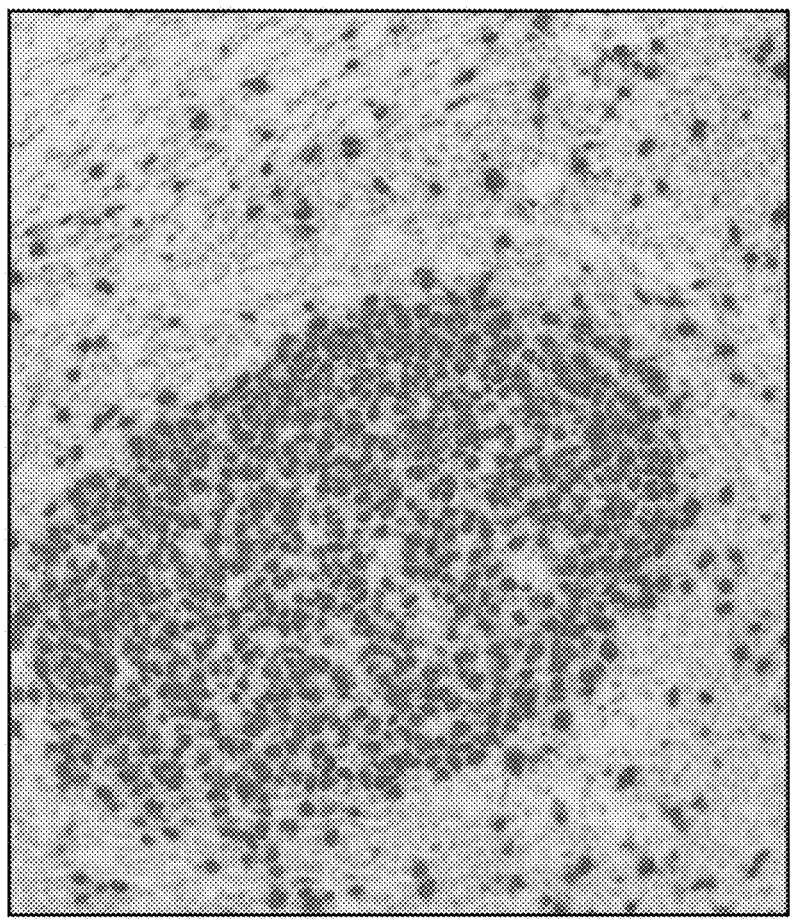

Three examples of IHC "click" amplification with different compounds of Formula (II) are illustrated in FIGS. 7A, 7B, and 7C. In general, each IHC assay was conducted according to the methods disclosed herein. In FIGS. 7A, 7B, and 7C, each tissue sample was first contacted with a primary antibody specific to a particular target (FIG. 7A CD8; FIG. 7B Bcl6; and FIG. 7C Ki67). Following introduction of the respective primary antibodies, each of the antibody-target complexes was labeled with an enzyme, such as by introducing a secondary antibody coupled to an alkaline phosphatase (AP) enzyme (e.g. a goat-anti-rabbit antibody-AP conjugate or a goat-anti-mouse antibody-AP conjugate).

Next, a first member of a pair of click conjugates was introduced and reacted with each AP labeled target. In FIG. 7A a compound of Formula (II) comprising a quinone methide precursor linked to a DBCO reactive function group was introduced and a quinone methide-DBCO tissue conjugate complex was formed after reaction with the target bound alkaline phosphatase. Subsequently, a conjugate of Formula (IV) comprising the chromogen TAMRA and an azide reactive functional group were introduced and reacted with the tissue conjugate complex to form a detectable tissue-click adduct complex. FIG. 7A clearly shows staining of the CD8 glycoprotein within a tonsil tissue sample.

In FIG. 7B a compound of Formula (II) comprising a quinone methide precursor linked to an azide reactive function group was introduced and a quinone methide-azide tissue conjugate complex was formed after reaction with the target bound alkaline phosphatase. Subsequently, a conjugate of Formula (IV) comprising the chromogen TAMRA and a DBCO reactive functional group were introduced and reacted with the tissue conjugate complex to form a detectable tissue-click adduct complex. FIG. 7B clearly shows staining of B-cell lymphoma 6 protein within a tonsil tissue sample.

In FIG. 7C a compound of Formula (II) comprising a quinone methide precursor linked to a TCO reactive function group was introduced and a quinone methide-TCO tissue conjugate complex was formed after reaction with the target bound alkaline phosphatase. Subsequently, a conjugate of Formula (IV) comprising the chromogen TAMRA and a tetrazine reactive functional group were introduced and reacted with the tissue conjugate complex to form a detectable tissue-click adduct complex. FIG. 7C clearly shows staining of the Ki67 protein within a tonsil tissue sample.

Example 2: "Click" Amplification with Compounds of Formula (III)

Figure 8A:
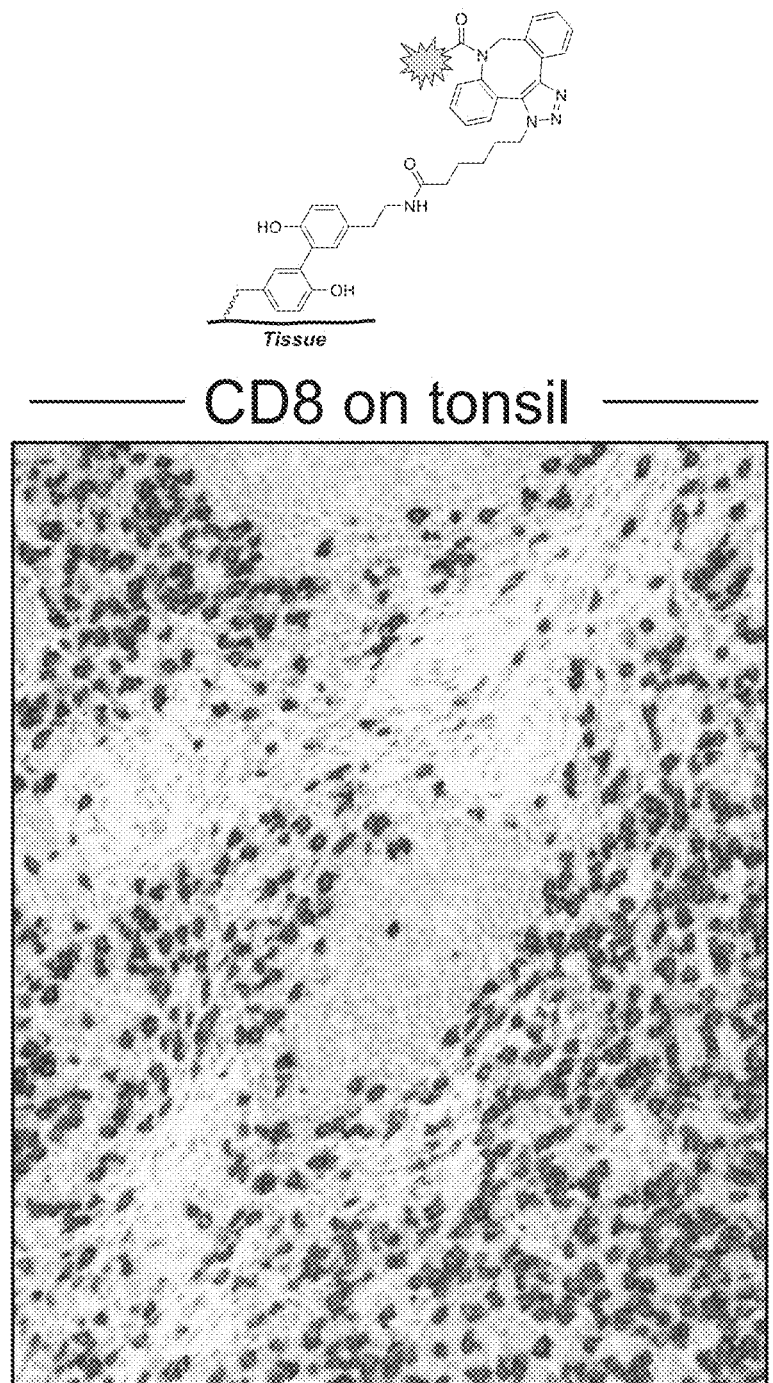
FIG. 8A illustrates staining of tonsil samples with a TSA conjugate.
Figure 8B:
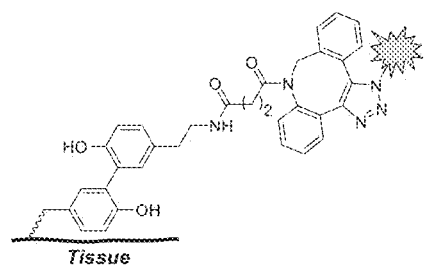
FIG. 8B is an additional illustration of staining of tonsil samples with a TSA conjugate.
Figure 8B:
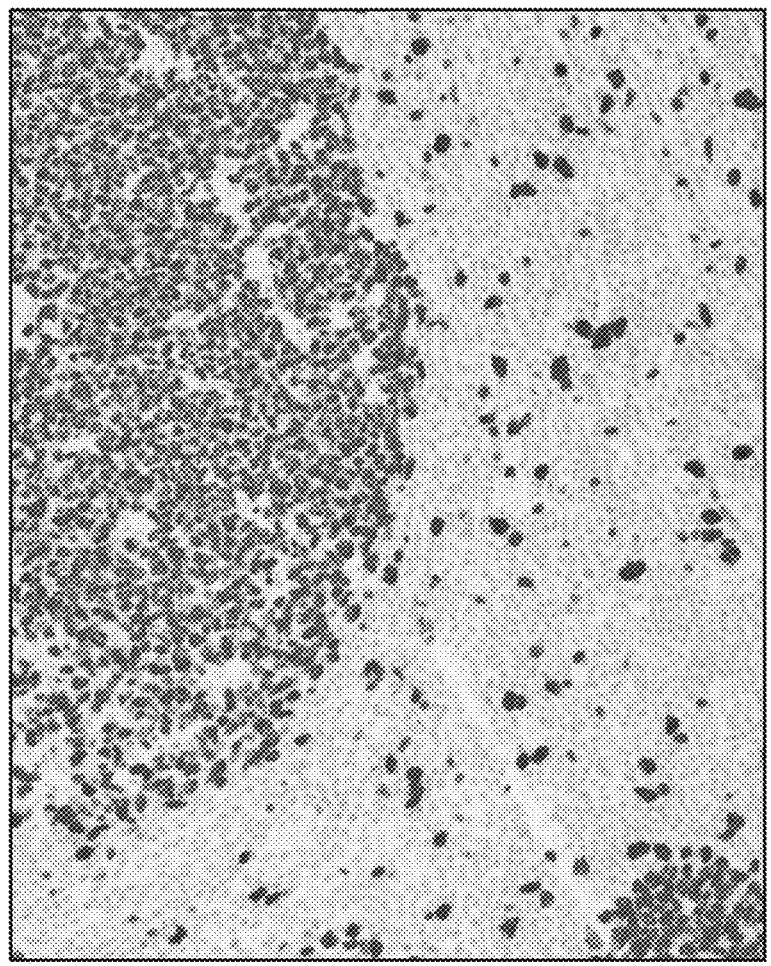
Figure 8C:
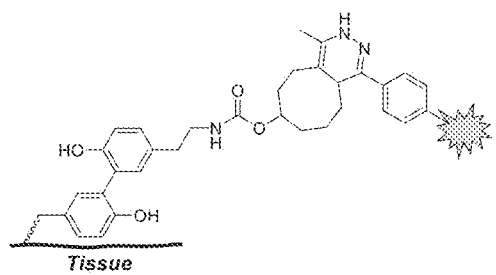
FIG. 8C is an additional illustration of staining of tonsil samples with a TSA conjugate.
Figure 8C:
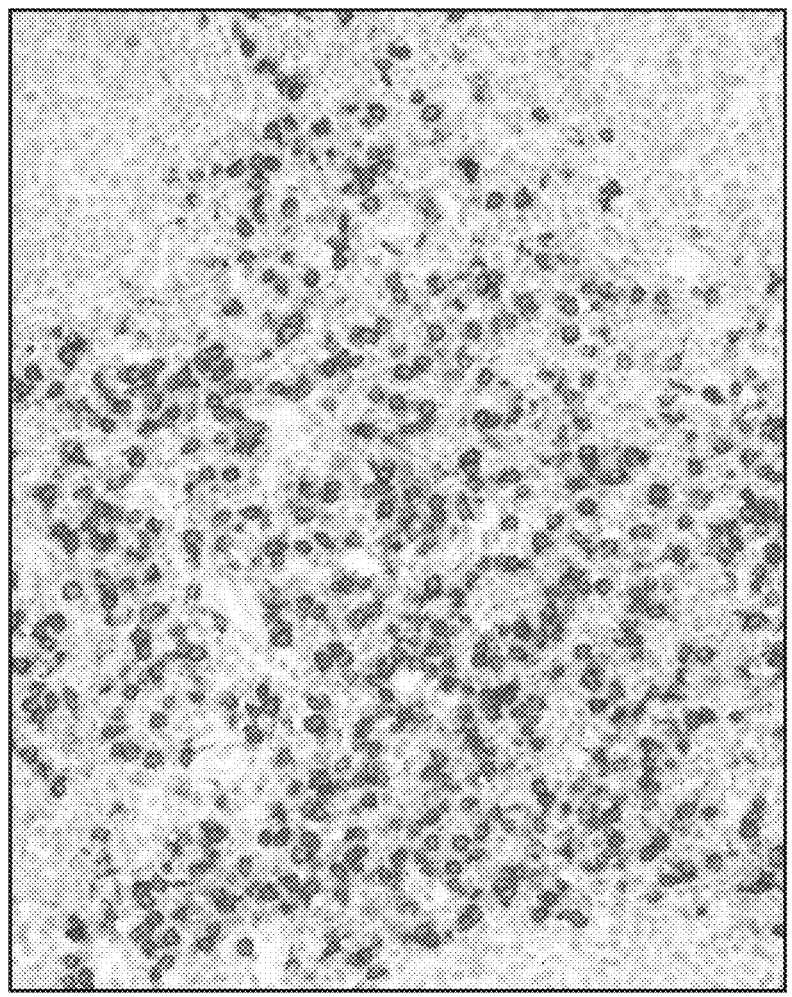

Three examples of IHC "click" amplification with different compounds of Formula (III) are illustrated in FIGS. 8A, 8B, and 8C. In general, each IHC assay was conducted according to the methods disclosed herein. In FIGS. 8A, 8B, and 8C, each tissue sample was first contacted with a primary antibody specific to a particular target (FIG. 8A CD8; FIG. 8B Bcl6; and FIG. 8C Ki67). Following introduction of the respective primary antibodies, each of the antibody-target complexes was labeled with an enzyme, such as by introducing a secondary antibody coupled to a horseradish peroxidase (HRP) enzyme (e.g. a goat-anti-rabbit antibody-HRP conjugate or a goat-anti-mouse antibody-HRP conjugate).

Next, a first member of a pair of click conjugates was introduced and reacted with each HRP labeled target. In FIG. 8A a compound of Formula (III) comprising a tyramide linked to an azide reactive function group was introduced and a tyramide-azide tissue conjugate complex was formed after reaction with the target bound HRP. Subsequently, a compound of Formula (IV) comprising the chromogen TAMRA and a DBCO reactive functional group were introduced and reacted with the tissue conjugate complex to form a detectable tissue-click adduct complex. FIG. 8A clearly shows staining of the CD8 glycoprotein within a tonsil tissue sample.

In FIG. 8B a compound of Formula (III) comprising a tyramide linked to a DBCO reactive function group was introduced and a tyramide-DBCO tissue conjugate complex was formed after reaction with the target bound HRP. Subsequently, a compound of Formula (IV) comprising the chromogen TAMRA and an azide reactive functional group were introduced and reacted with the tissue conjugate complex to form a detectable tissue-click adduct complex. FIG. 8B clearly shows staining of the Ki67 protein within a tonsil tissue sample.

In FIG. 8C a compound of Formula (III) comprising a tyramide linked to a TCO reactive function group was introduced and a tyramide-TCO tissue conjugate complex was formed after reaction with the target bound HRP. Subsequently, a compound of Formula (IV) comprising the chromogen TAMRA and a tetrazine reactive functional group were introduced and reacted with the tissue conjugate complex to form a detectable tissue-click adduct complex. FIG. 8C clearly shows staining of the CD8 glycoprotein within a tonsil tissue sample.

Example 3

FIGS. 9A, 9B, 9C, and 9D illustrate the results from four different IHC assays. Each assay was conducted using the general procedures described herein, and exemplified in Example 1. As applied here, each assay utilized the same click conjugate of Formula (II), namely one comprising a tyramine moiety conjugated to a DBCO reactive functional group ("Tyramide-DBCO"). However, four different click conjugates of Formula (IV) were used for coupling with Tyramide-DBCO, each having a different chromogen or chromogenic system coupled to an azide reactive functional group. As depicted in FIG. 9A, the Tyramide-DBCO conjugate was reacted with a click conjugate of Formula (IV) where the click conjugate of Formula (IV) comprised a coupled Cy5 chromogen. As depicted in FIG. 9B, the Tyramide-DBCO conjugate was reacted with a click conjugate of Formula (IV) where the click conjugate of Formula (IV) comprised a coupled Dabsyl chromogen. As depicted in FIG. 9C, the Tyramide-DBCO conjugate reacted with a click conjugate of Formula (IV) where the click conjugate of Formula (IV) comprised both a TAMRA chromogen and a Dabcyl chromogen, where the two chromogens were coupled via lysine scaffold. As depicted in FIG. 9D, the Tyramide-DBCO conjugate was reacted with a click conjugate of Formula (IV) where the click conjugate of Formula (IV) comprised a coupled TAMRA chromogen. Each of FIGS. 9A to 9D thus illustrate that a click conjugate species comprising a tissue reactive precursor moiety and a particular reactive functional group may be reacted with different compounds of Formula (IV) having different chromogens to stain tissue different colors.

Example 4: Comparison of "Traditional" TSA to "Click" Amplification in an IHC Assay FIG. 10 comparatively illustrates staining with a DAB control, various TSA chromogens (TSA-TAMRA, TSA-Cy5, and TSA-Dabsyl), and the TSA "click" conjugates of the present disclosure (tyramide-DBCO:TAMRA-Azide; tyramide-DBCO:Cy5-Azide; and tyramide-DBCO:Dabsyl-Azide).

The tissue sample labeled "DAB control" was stained in an IHC assay utilizing a primary antibody specific for Ki67 and a goat-anti-rabbit antibody conjugated to HRP. The antigen was visualized via a brown precipitate produced by HRP upon the addition of hydrogen peroxide and 3,3'-diaminobenzidine (DAB). The DAB hue was toned by the addition of copper sulfate.

Figure 10:
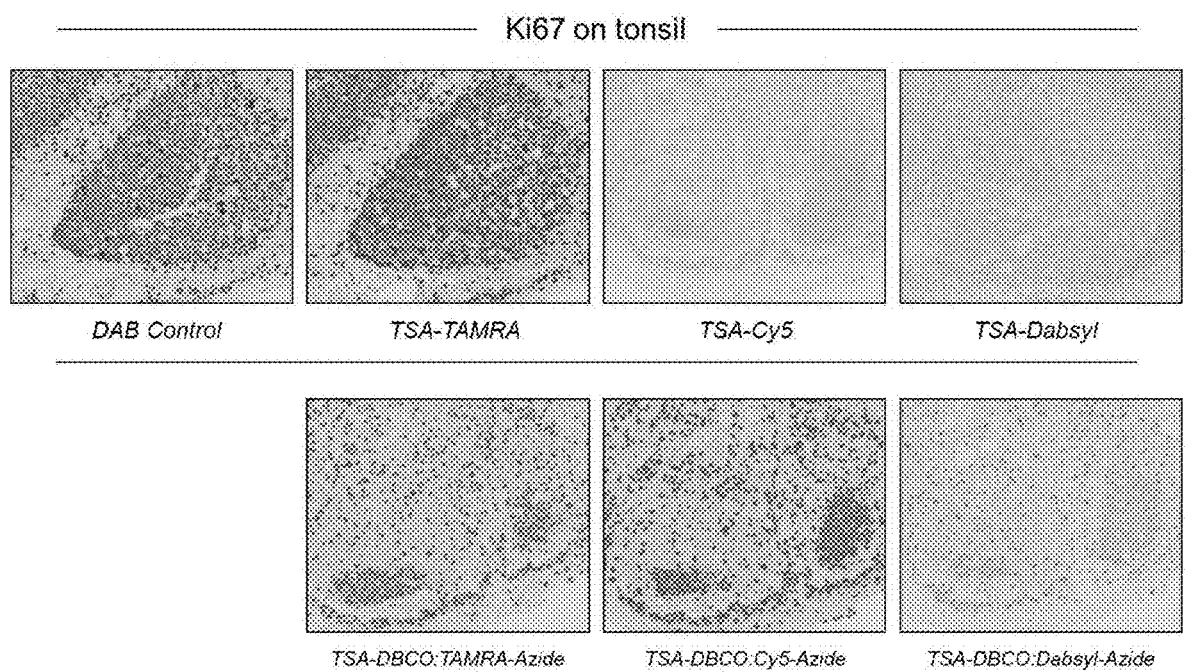
FIG. 10 comparatively illustrates the results of IHC staining using a (i) DAB control, (ii) using a TSA protocol, and (iii) using an amplification protocol utilizing the click-conjugates of the present disclosure.

The tissue samples identified as being stained with TSA-TAMRA, TSA-Cy5, and TSA-Dabsyl in FIG. 10 were stained in an IHC assay using a traditional tyramide signal amplification technique. First, a primary antibody specific to Ki67 was introduced to form a primary antibody-Ki67 complex. The primary antibody-Ki67 complex was then labeled with a horseradish peroxidase enzyme, through a secondary antibody, namely a goat-anti-rabbit antibody-HRP conjugate. Subsequently, a tyramide coupled to a chromogen, namely TSA-TAMRA, TSA-Cy5, and TSA-Dabsyl, were each independently introduced and each was subsequently deposited on or adjacent the target following reaction with horseradish peroxidase.

The tissue samples identified as being stained with TSA-DBCO:TAMRA-Azide, tyramide-DBCO:Cy5-Azide; and tyramide-DBCO:Dabsyl-Azide in FIG. 10 were stained in an IHC assay using the general techniques described herein and those provided in Example 2.

As compared with the samples stained in the traditional TSA assays, the tissues stained using Cy5 or Dabsyl in "click" amplification according to the methods described herein showed significant increases in staining intensity, as clearly shown in FIG. 10.

Example 5: Comparison of "Traditional" TSA to "Click" Amplification in an ISH Assay FIG. 11 comparatively illustrates staining of various TSA chromogens (TSA-TAMRA, TSA-Cy5, and TSA-Dabsyl), and the TSA "click" conjugates of the present disclosure (tyramide-DBCO:TAMRA-Azide; tyramide-DBCO:Cy5-Azide; and tyramide-DBCO:Dabsyl-Azide).

Figure 11:
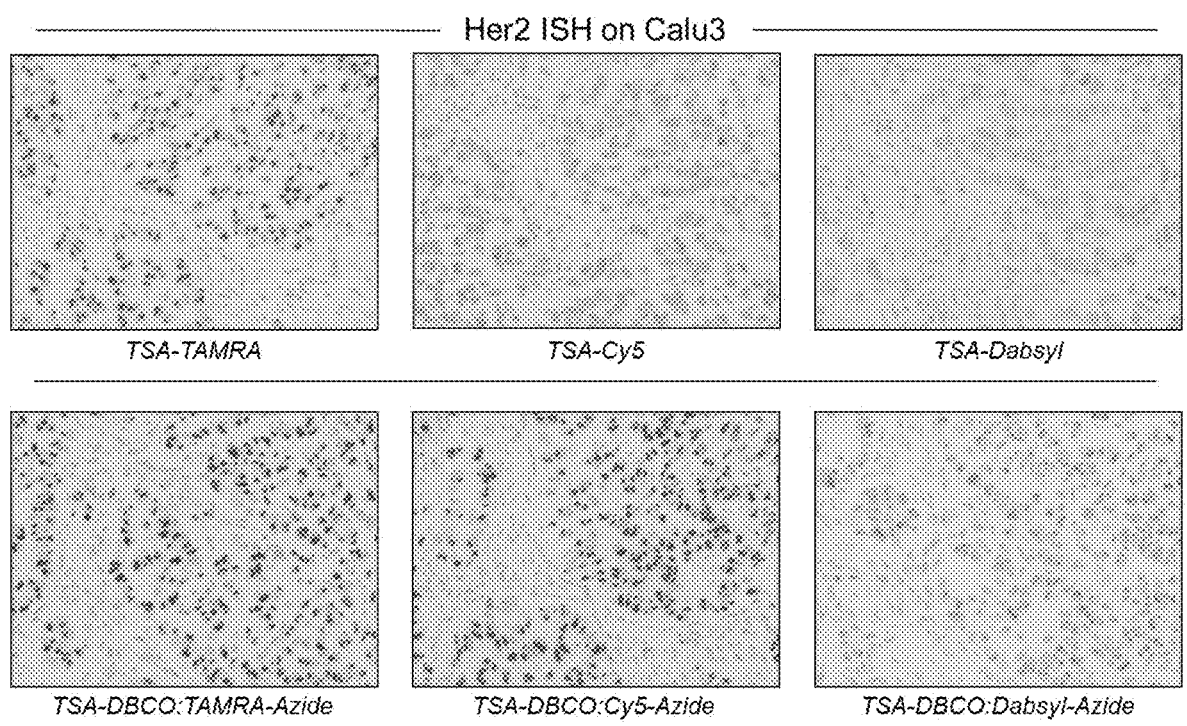
FIG. 11 comparatively illustrates differences in staining intensities in an ISH assay using (i) a TSA protocol and (ii) an amplification protocol utilizing the click conjugates of the present disclosure.

The tissue samples identified as being stained with TSA-TAMRA, TSA-Cy5, and TSA-Dabsyl in FIG. 11 were stained in an ISH assay using a traditional tyramide signal amplification technique. First, a nucleic acid probe specific to Her2 was introduced to a tissue sample, the Her2 probe conjugated to a detectable label, namely a DNP hapten. The DNP was bound by a rabbit-anti-DNP antibody, which was then labeled with a goat-anti-rabbit antibody conjugated to HRP. Subsequently, TSA-TAMRA, TSA-Cy5, and TSA-Dabsyl were each independently introduced and each was subsequently deposited on or adjacent the target following reaction with horseradish peroxidase.

The tissue samples identified as being stained with TSA-DBCO:TAMRA-Azide, tyramide-DBCO:Cy5-Azide; and tyramide-DBCO:Dabsyl-Azide in FIG. 11 were stained according to the general techniques described herein (see, e.g., FIG. 15).

As compared with the samples stained in the traditional TSA assays, the tissues stained using Cy5 or Dabsyl in "click" amplification according to the methods described herein showed significant increases in staining intensity, as clearly shown in FIG. 11.

Example 6

Figure 12A:
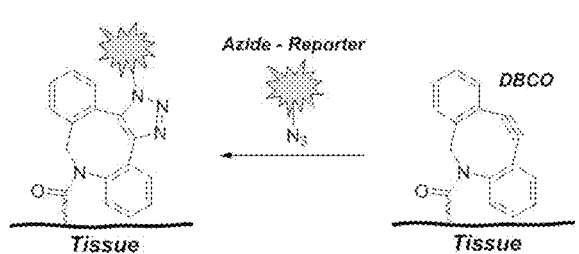
Figure 12B:
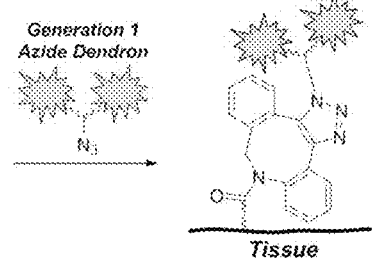

FIG. 12 illustrates the differences in staining using a click conjugate of Formula (IV) comprising a single reporter moiety versus another click conjugate of Formula (IV) comprising multiple reporter moieties. The tissue sample on the left was stained using a click conjugate of Formula (IV) comprising a single TAMRA chromogen. The tissue sample on the right was staining using a click conjugate of Formula (V) comprising at least two TAMRA chromogens, the TAMRA chromogens coupled together using a dendrimer.

Example 7

Figures 13A, 13B, 13C:
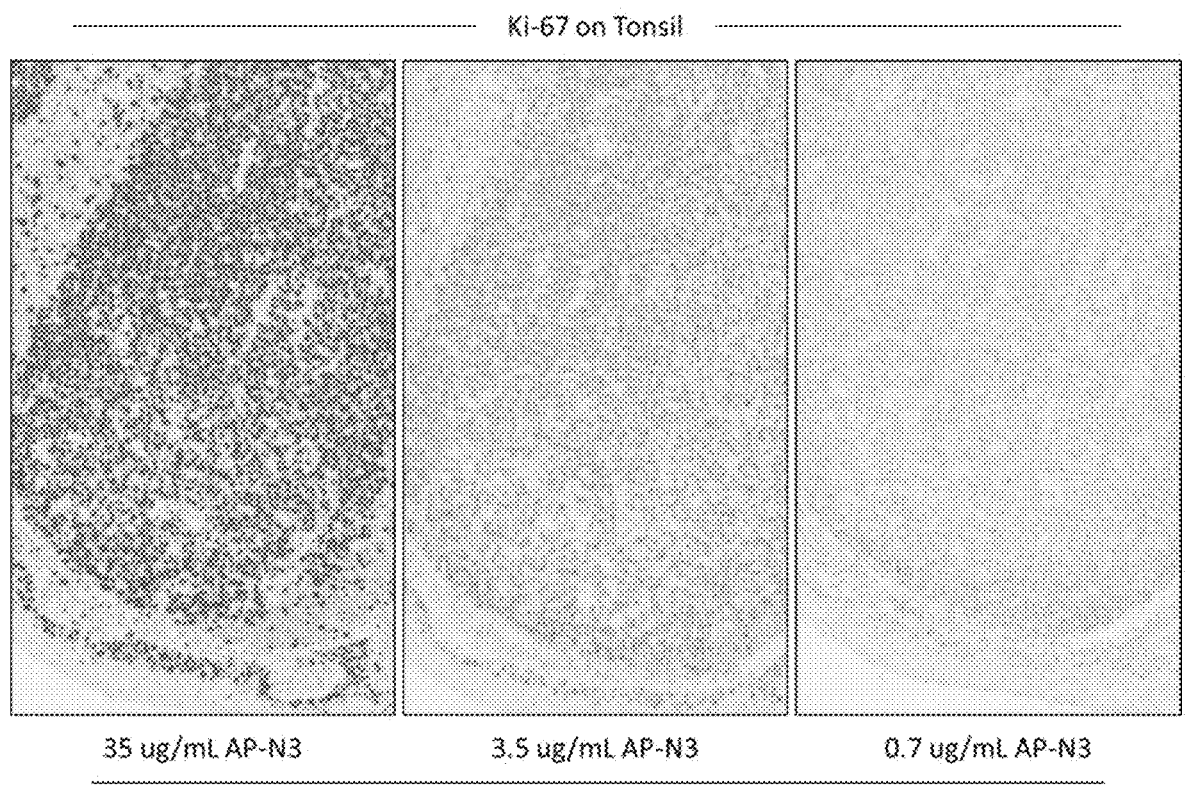
FIGS. 13A-13C illustrate staining intensities using a click conjugate comprising an alkaline phosphatase as a reporter moiety.

FIG. 13 illustrates the staining of tissue with an enzyme-tissue click adduct. The IHC assay was conducted according to the methods disclosed herein. Following introduction of the rabbit-anti-Ki67 primary antibody, each of the antibody-target complexes was labeled with a secondary goat-anti-rabbit antibody coupled to a horseradish peroxidase (HRP) enzyme. Next, a compound of Formula (III) comprising a tyramide linked to a DBCO reactive function group (first member of a pair of click conjugates), was introduced along with hydrogen peroxide and reacted with each HRP labeled target. A tyramide-DBCO tissue conjugate complex was formed after reaction with the target bound HRP. Subsequently, a compound of Formula (IV) comprising the enzyme AP and an azide reactive functional group were introduced (second member of a pair of click conjugates) and reacted with the tissue conjugate complex to form a detectable tissue-click adduct. The AP-tissue click adduct was then detected with QMSA-TAMRA chromogenic detection. FIG. 13 clearly shows the increase in staining of the Ki67 protein within a tonsil tissue sample corresponding to increasing concentration of AP-azide.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Additional Exemplary Embodiments

The following embodiments are also explicitly disclosed. This is not intended to be an exhaustive list.

1. A conjugate having Formula (IIa):

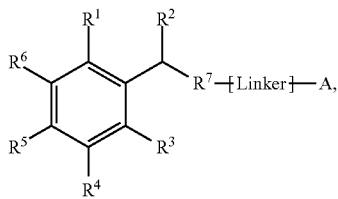

(IIa)

wherein

A is selected from the group consisting of dibenzocyclooctyne, trans-cyclooctene, azide, tetrazine, maleimide, thiol, 1,3-nitrone, aldehyde, ketone, hydrazine, and hydroxylamine;

'Linker' is a branched or unbranched, linear or cyclic, substituted or unsubstituted, saturated or unsaturated, group having between 2 and 80 carbon atoms, and optionally having one or more heteroatoms selected from O, N, or S;

$R^1$ is a group selected from phosphate, amide, nitro, urea, sulfate, methyl, ester, beta-lactam, or a sugar;

$R^2$ is a halide;

$R^3$, $R^5$, and $R^6$ are independently selected from hydrogen or an aliphatic group having between 1 and 4 carbon atoms;

$R^4$ is a hydrogen, an aliphatic group having between 1 and 4 carbon atoms, or the group —CH($R^2$)—$R^7$-[Linker]-A; and $R^7$ is selected from the group consisting of —(CH$_2$)$_w$NH—, —O(CH$_2$)$_w$NH—, —N(H)C(O)(CH$_2$)$_w$NH—, —C(O)N(H)(CH$_2$)$_w$NH—, —(CH$_2$)$_w$O—, —O(CH$_2$)$_w$O—, —O(CH$_2$CH$_2$O)$_w$—, —N(H)C(O)(CH$_2$)$_w$O—, —C(O)N(H)(CH$_2$)$_w$O—, —C(O)N(H)(CH$_2$CH$_2$O)$_w$—, —(CH$_2$)$_w$S—, —O(CH$_2$)$_w$S—, —N(H)C(O)(CH$_2$)$_w$S—, —C(O)N(H)(CH$_2$)$_w$S—, —(CH$_2$)$_w$NH—, —C(O)N(H)(CH$_2$CH$_2$O)$_w$CH$_2$CH$_2$NH, —C(O)(CH$_2$CH$_2$O)wCH$_2$CH$_2$NH—, C(O)N(H)(CH$_2$)NHC(O)CH(CH$_3$)(CH$_2$)$_w$NH—, or —N(H)(CH$_2$)$_w$NH—, where w is an integer ranging from 1 to 12.

2. The conjugate of embodiment 1, wherein $R^6$, $R^5$, $R^4$, and $R^3$ are each hydrogen.

3. The conjugate of embodiment 1 or 2, wherein $R^1$ is a phosphate.

4. The conjugate of any of embodiments 1 to 3, wherein $R^2$ is fluorine.

5. The conjugate of embodiment 1, wherein $R^1$ is a phosphate; $R^2$ is fluorine; and $R^6$, $R^5$, $R^4$, and $R^3$ are each hydrogen.

6. The conjugate of any of embodiments 1 to 5, wherein 'Linker' has the Formula (Ia):

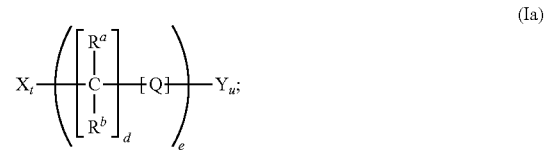

(Ia)

wherein d and e are integers each independently ranging from 2 to 20;

t and u are independently 0 or 1;

Q is a bond, O, S, or N(R$^c$)(R$^d$);

$R^a$ and $R^b$ are independently H, a C$_1$-C$_4$ alkyl group, F, Cl, or N(R$^c$)(R$^d$);

$R^c$ and $R^d$ are independently CH$_3$ or H; and

X and Y are independently a branched or unbranched, linear or cyclic, substituted or unsubstituted, saturated or unsaturated group having between 1 and 12 carbon atoms and optionally having one or more O, N, or S heteroatoms.

7. The conjugate of claim 6, wherein $R^a$ and $R^b$ are each hydrogen.

8. The conjugate of claim 7, wherein Q is oxygen.

9. The conjugate of any of claims 1 to 8, wherein $R^7$ is —C(O)N(H)(CH$_2$)$_w$NH—.

10. The conjugate of claim 1 or 2, wherein $R^1$ is a phosphate and $R^7$ is —C(O)N(H)(CH$_2$)$_w$NH—, and w ranges from 2 to 10.

11. The conjugate of claim 10, wherein $R^2$ is fluorine; and $R^6$, $R^5$, $R^4$, and $R^3$ are each hydrogen.

12. The conjugate of claim 11, wherein 'Linker' comprises a PEG group.

13. A conjugate having Formula (IId):

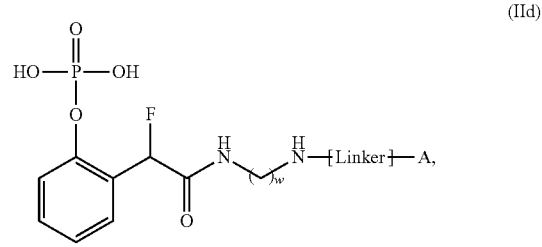

(IId)

wherein

A is selected from the group consisting of dibenzocyclooctyne, trans-cyclooctene, azide, tetrazine, maleimide, thiol, 1,3-nitrone, aldehyde, ketone, hydrazine, and hydroxylamine;

'Linker' is a branched or unbranched, linear or cyclic, substituted or unsubstituted, saturated or unsaturated, group having between 2 and 80 carbon atoms, and optionally having one or more heteroatoms selected from O, N, or S; and w ranges from 1 to 12.

14. The conjugate of claim 13, wherein 'Linker' has the Formula (Ia):

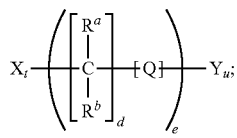

wherein d and e are integers each independently ranging from 2 to 20;

t and u are independently 0 or 1;

Q is a bond, O, S, or $N(R^c)(R^d)$;

$R^a$ and $R^b$ are independently H, a $C_1$-$C_4$ alkyl group, F, Cl, or $N(R^c)(R^d)$;

$R^c$ and $R^d$ are independently $CH_3$ or H; and

X and Y are independently a branched or unbranched, linear or cyclic, substituted or unsubstituted, saturated or unsaturated group having between 1 and 12 carbon atoms and optionally having one or more O, N, or S heteroatoms.

15. The conjugate of claim 14, wherein w ranges from 1 to 8; and wherein $R^a$ and $R^b$ are each hydrogen.

16. The conjugate of claim 15, wherein w ranges from 2 to 8, and wherein Q is oxygen.

17. The conjugate of claim 16, wherein d and e are independently an integer ranging from 2 to 10.

18. The conjugate of any of claims 13 to 17, wherein A is dibenzocyclooctyne.

19. The conjugate of claim 18, wherein w ranges from 2 to 6 and wherein the Linker comprises a PEG group.

20. The conjugate of any of claims 13 to 17, wherein A is trans-cyclooctene.

21. The conjugate of claim 20, wherein w ranges from 2 to 6 and wherein the Linker comprises a PEG group.

22. The conjugate of any of claims 13 to 17, wherein A is azide.

23. The conjugate of claim 23, wherein w ranges from 2 to 6 and wherein the Linker comprises a PEG group.

24. The conjugate of any of claims 13 to 17, wherein A is tetrazine.

25. The conjugate of claim 24, wherein w ranges from 2 to 6 and wherein the Linker comprises a PEG group.

26. A conjugate having Formula (III):

wherein

M is derived from a propionic acid, a cinnamic acid, or a compound of Formula (IIIa),

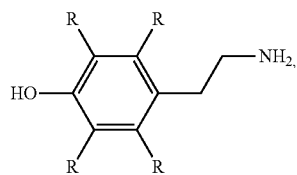

wherein each R group is independently selected from hydrogen or lower alkyl group having between 1 and 4 carbon atoms;

A is selected from the group consisting of dibenzocyclooctyne, trans-cyclooctene, azide, tetrazine, maleimide, thiol, 1,3-nitrone, aldehyde, ketone, hydrazine, and hydroxylamine; and 'Linker' is a branched or unbranched, linear or cyclic, substituted or unsubstituted, saturated or unsaturated, group having between 2 and 80 carbon atoms, and optionally having one or more heteroatoms selected from O, N, or S;

provided that when each R is hydrogen, A is selected from the group consisting of an azide, a thiol, a 1,3-nitrone, a hydrazine, or a hydroxylamine.

27. The conjugate of claim 26, wherein 'Linker' has the formula (Ia)

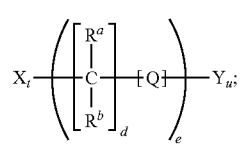

wherein d and e are integers each independently ranging from 2 to 20;

t and u are independently 0 or 1;

Q is a bond, O, S, or $N(R^c)(R^d)$;

$R^a$ and $R^b$ are independently H, a $C_1$-$C_4$ alkyl group, F, Cl, or $N(R^c)(R^d)$;

$R^c$ and $R^d$ are independently $CH_3$ or H; and

X and Y are independently a branched or unbranched, linear or cyclic, substituted or unsubstituted, saturated or unsaturated group having between 1 and 12 carbon atoms and optionally having one or more O, N, or S heteroatoms.

28. The conjugate of claim 27, wherein $R^a$ and $R^b$ are each hydrogen.

29. The conjugate of claim 27 or 28, wherein Q is oxygen.

30. The conjugate of claim 27, wherein $R^a$ and $R^b$ are each hydrogen, Q is oxygen, and e ranges from 2 to 10.

31. A conjugate having Formula (Id):

wherein

A is selected from the group consisting of dibenzocyclooctyne, trans-cyclooctene, azide, tetrazine, maleimide, thiol, 1,3-nitrone, aldehyde, ketone, hydrazine, and hydroxylamine;

'Linker' is a branched or unbranched, linear or cyclic, substituted or unsubstituted, saturated or unsaturated, group having between 2 and 80 carbon atoms, and optionally having one or more heteroatoms selected from O, N, or S; and 'Tissue Reactive Moiety' is derived from a compound selected from the group consisting of:

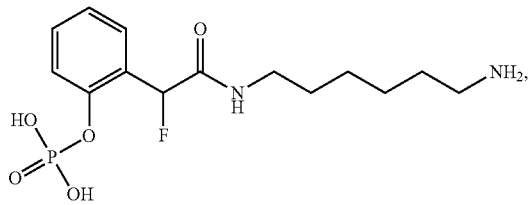

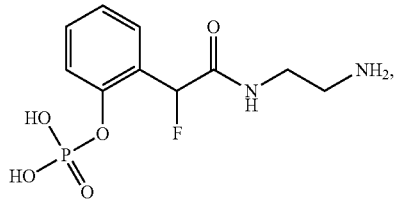

-continued

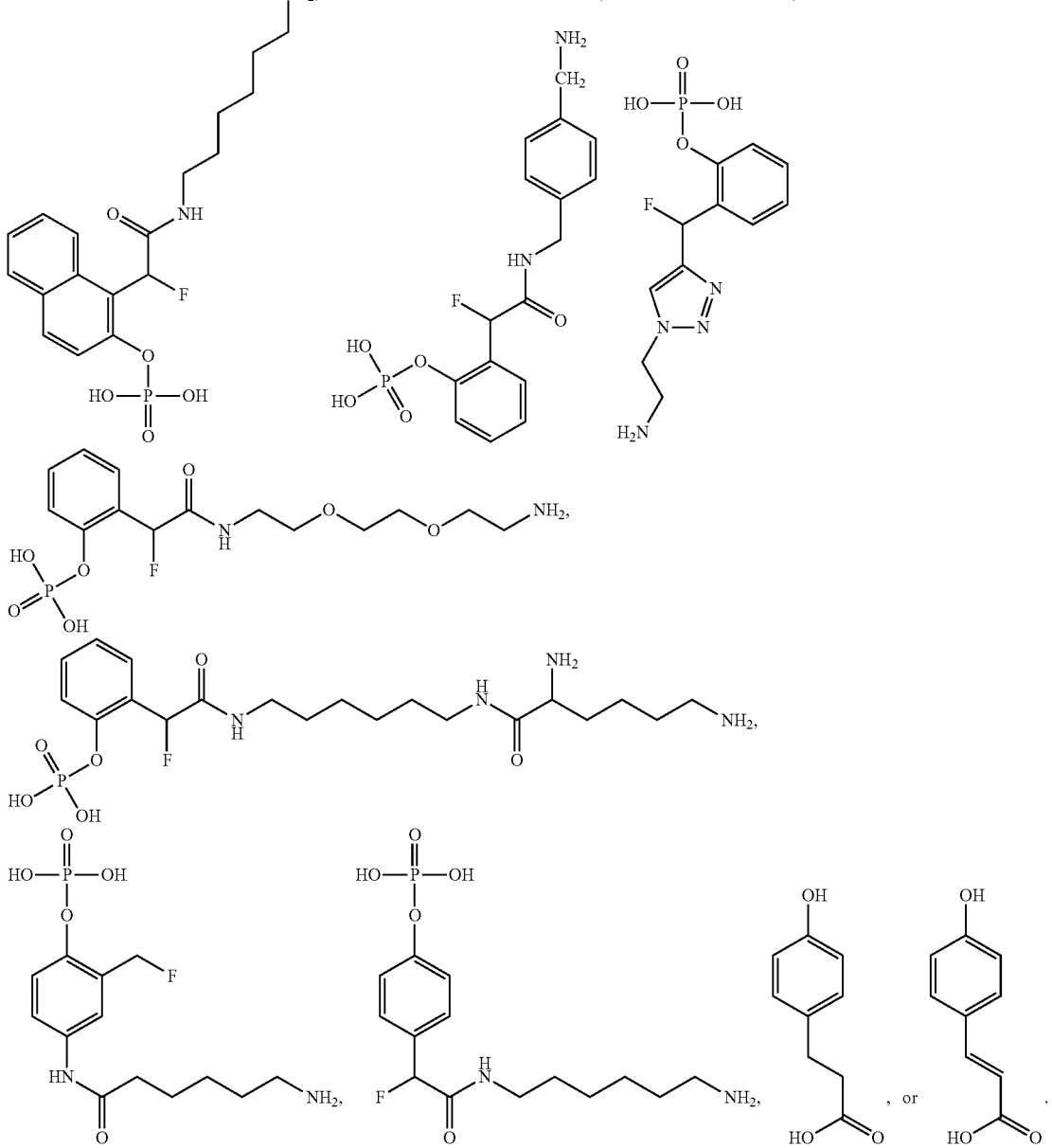

32. The conjugate of claim 31, wherein 'Linker' has the Formula (Ia):

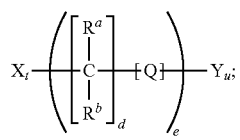

wherein
d and e are integers each independently ranging from 2 to 20;
t and u are independently 0 or 1;
Q is a bond, O, S, or $N(R^c)(R^d)$;

$R^a$ and $R^b$ are independently H, a $C_1$-$C_4$ alkyl group, F, Cl, or $N(R^c)(R^d)$;

$R^c$ and $R^d$ are independently $CH_3$ or H; and

X and Y are independently a branched or unbranched, linear or cyclic, substituted or unsubstituted, saturated or unsaturated group having between 1 and 12 carbon atoms and optionally having one or more O, N, or S heteroatoms.

33. The conjugate of claim 32, wherein $R^a$ and $R^b$ are each hydrogen.

34. The conjugate of claim 32 or 33, wherein Q is oxygen.

35. The conjugate of claim 32, wherein $R^a$ and $R^b$ are each hydrogen, Q is oxygen, and e ranges from 2 to 10.

36. A conjugate having Formula (IV):

A—[Linker]—Z       (IV), wherein

A is selected from the group consisting of dibenzocyclooctyne, trans-cyclooctene, azide, tetrazine, maleimide, thiol, 1,3-nitrone, aldehyde, ketone, hydrazine, and hydroxylamine;

'Linker' is a branched or unbranched, linear or cyclic, substituted or unsubstituted, saturated or unsaturated, group having between 2 and 80 carbon atoms, and optionally having one or more heteroatoms selected from O, N, or S; and Z is selected from the group consisting of a chromophore, a fluorophore, an enzyme, a hapten, and a chelator.

37. The conjugate of claim 36, Z is a chromophore selected from the group consisting of tetramethylrhodamine, Cyanine 5, and Dabsyl.

38. The conjugate of claim 36, where Z is selected from the group consisting of:

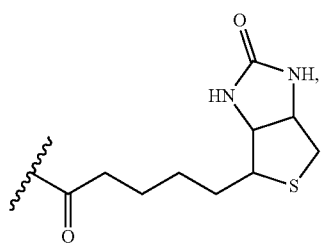

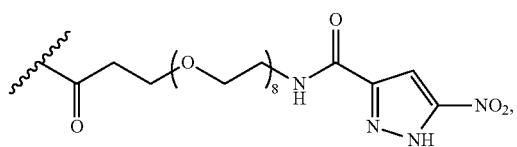

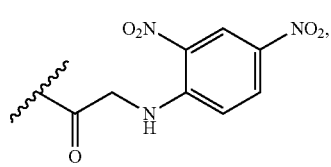

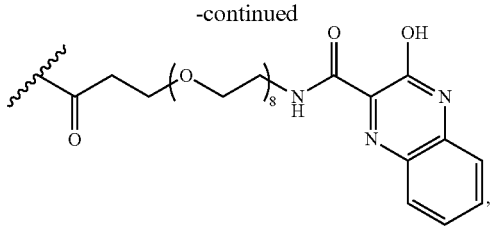

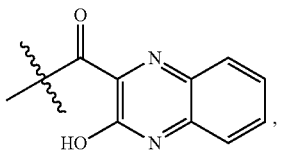

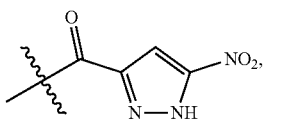

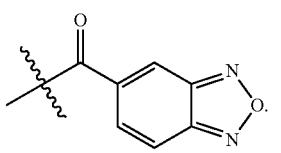

39. The conjugate of claim 36, wherein the conjugate has the structure of Formula (IVa):

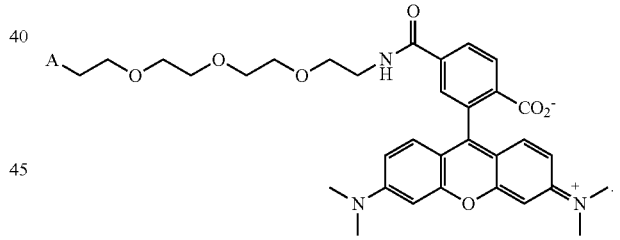

(IVa)

40. The conjugate of claim 36, wherein the conjugate has the structure of Formula (IVb):

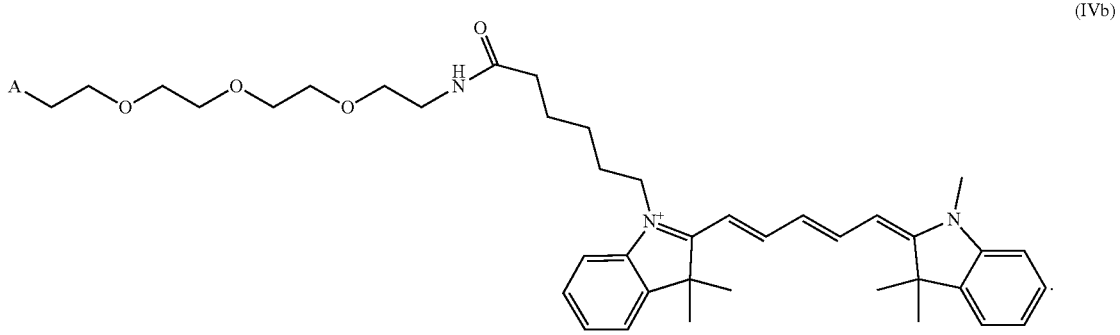

(IVb)

41. The conjugate of claim 36, wherein the conjugate has the structure of Formula (IVc):
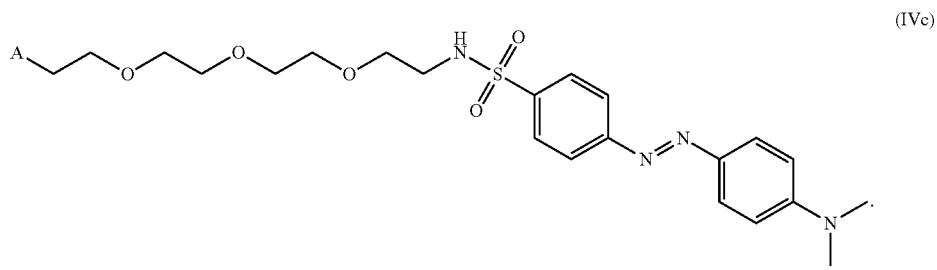
(IVc)
42. The conjugate of claim 36, wherein the conjugate has the structure of Formula (IVd):
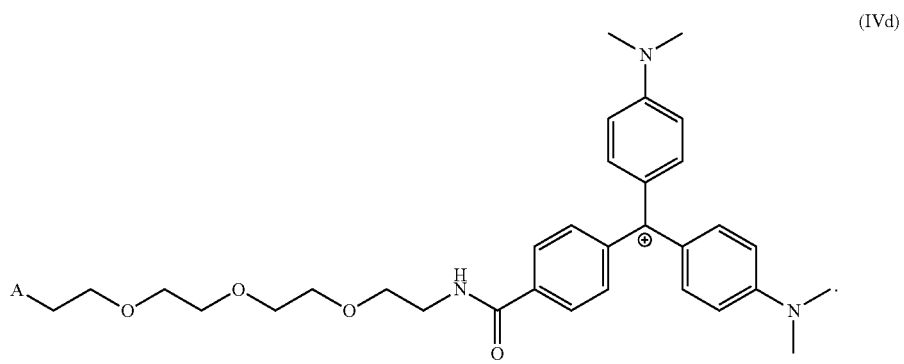
(IVd)
43. The conjugate of claim 36, wherein the conjugate is:
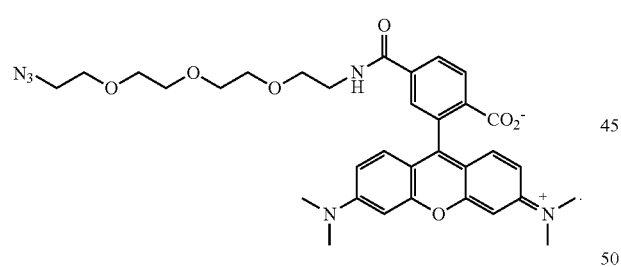
44. The conjugate of claim 36, wherein the conjugate is:
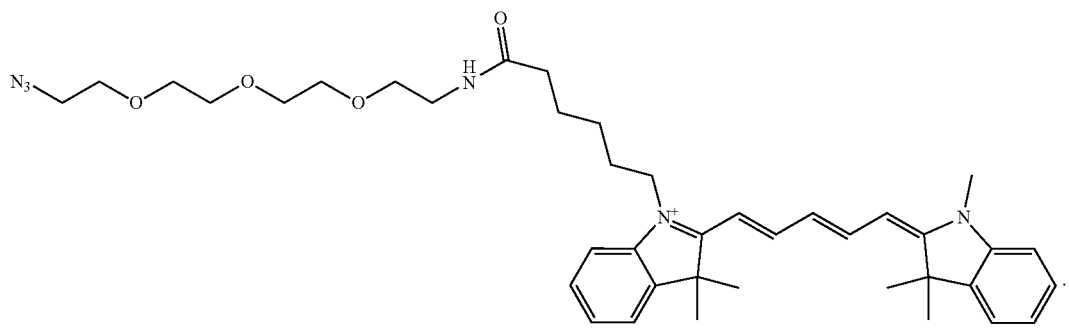 [SMILES: CN1/C(=C/C=C/C=C/C2=[N+](CCCCCC(=O)NCCOCCOCCOCCN=[N+]=[N-])c3ccccc3C2(C)C)C(C)(C)c2ccccc21]

45. The conjugate of claim 36, wherein the conjugate is:
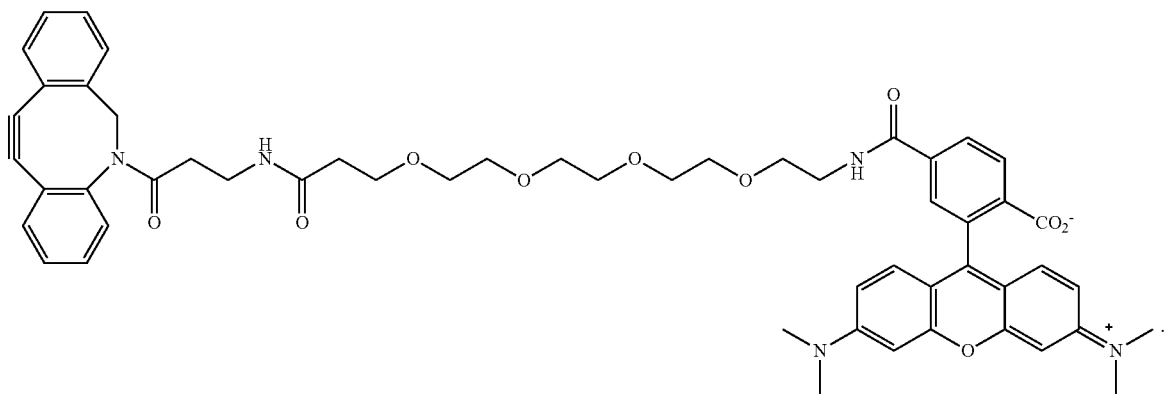
46. The conjugate of claim 36, wherein the conjugate is:
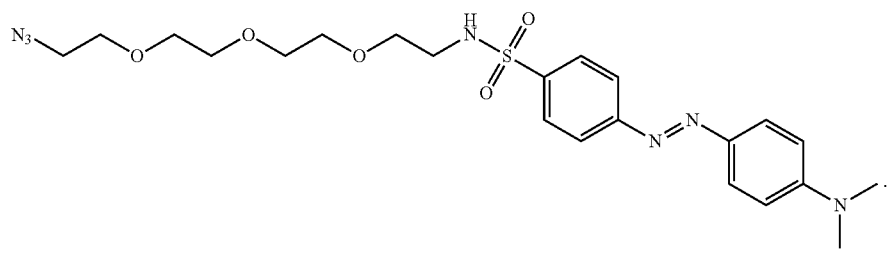 [SMILES: CN(C)c1ccc(/N=N/c2ccc(S(=O)(=O)NCCOCCOCCOCCN=[N+]=[N-])cc2)cc1]
47. The conjugate of claim 36, wherein the conjugate is:
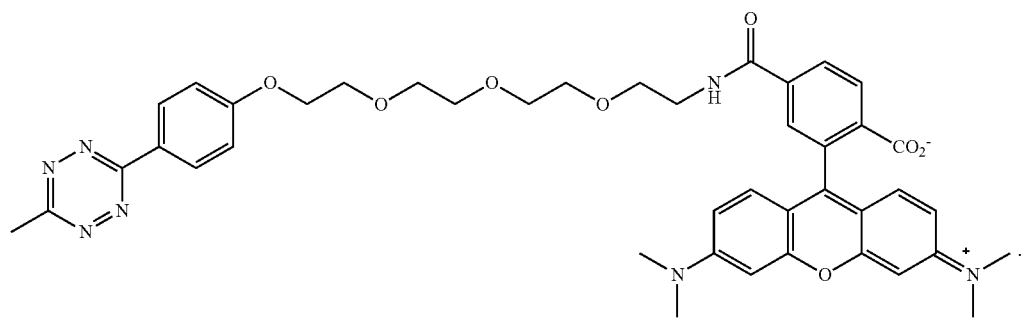
48. The conjugate of claim 36, wherein the conjugate is:
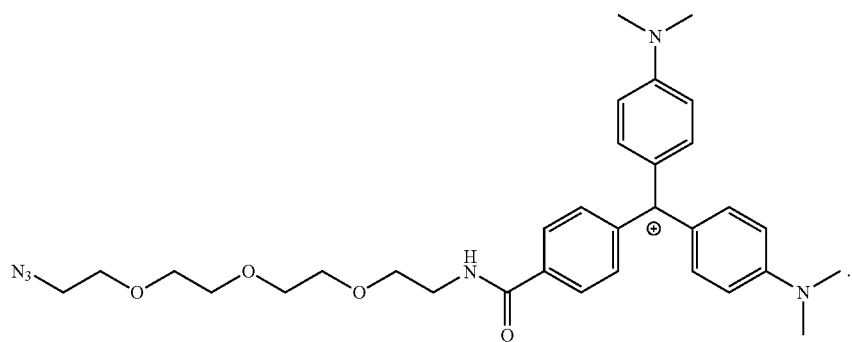 [SMILES: CN(C)c1ccc(C(c2ccc(C(=O)NCCOCCOCCOCCN=[N+]=[N-])cc2)c2ccc(N(C)C)cc2)cc1]

49. The conjugate of claim 36, wherein the conjugate is:

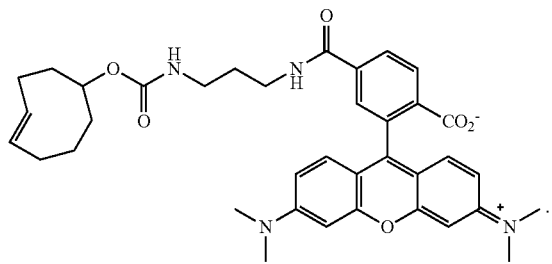

50. The conjugate of claim 36, wherein the conjugate is:

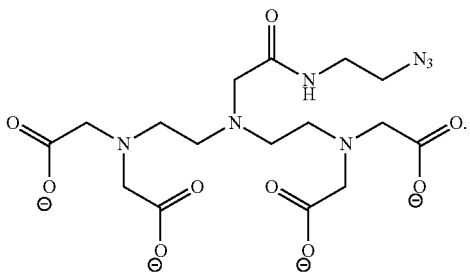 [SMILES: [N-]=[N+]=NCCNC(=O)CN(CCN(CC(=O)[O-])CC(=O)[O-])CCN(CC(=O)[O-])CC(=O)[O-]]

51. A method of detecting a first target in a biological sample, comprising:
   (i) contacting the biological sample with a first detection probe specific to the first target to form a first detection probe-target complex;
   (ii) contacting the biological sample with a first labeling conjugate specific for the first detection probe, the first labeling conjugate comprising a first enzyme such that the first-detection probe-target complex becomes labeled with the first enzyme;
   (iii) contacting the biological sample with a first member of a first pair of click conjugates, the first member of the first pair of click conjugates comprising a tissue reactive moiety, wherein the first enzyme converts the first member of the first pair of click conjugates to a first reactive intermediate which covalently bonds to the biological sample proximally to or directly on the first target to form a first immobilized tissue-click conjugate complex;
   (iv) contacting the biological sample with a second member of a first pair of click conjugates, the second member of the first pair of click conjugates comprising a second reactive moiety capable of reacting with a first reactive moiety of the first immobilized tissue-click conjugate complex such that a covalent bond is formed between the first immobilized tissue-click conjugate complex and the second member of the first pair of click conjugates to form a first tissue-click conjugate adduct; and
   (v) detecting signals from a first reporter moiety of first tissue-click conjugate adduct 52. The method of claim 51, wherein the first member of the first pair of click conjugates comprises the conjugate of any of claims 1 to 35.

53. The method of claim 51 or 52, wherein the second member of the first pair of click conjugates comprises the conjugate of any of claims 36 to 50.

54. The method of claim 51 or 52, wherein the second member of the first pair of click conjugates comprises at least one chromophore.

55. The method of claim 51, wherein the first member of the first pair of click conjugates comprises a quinone methide precursor moiety; and wherein the second member of the first pair of click conjugates comprises a chromophore.

56. The method of claim 51, wherein the first member of the first pair of click conjugates comprises a tyramide moiety; and wherein the second member of the first pair of click conjugates comprises a chromophore.

57. The method of any of claims 51 to 56, wherein the first detection probe is a primary antibody, and wherein the first labeling conjugate comprises an anti-antibody antibody.

58. The method of any of claims 51 to 57, wherein the first enzyme is selected from the group consisting of phosphatase, phosphodiesterase, esterase, lipase, amidase, protease, nitroreductase, urease, sulfatase, cytochrome P450, alpha-glucosidase, beta-glucosidase, beta-lactamase, alpha-glucoronidase, beta-glucoronidase, alpha-5-galactosidase, beta-galactosidase, neuraminidase, alpha-lactase and beta-lactase.

59. The method of any of claims 51 to 58, further comprising detecting a second target in the biological sample, wherein the second target is detected by
   (i) contacting the biological sample with a second detection probe specific to the second target to form a second detection probe-target complex;
   (ii) contacting the biological sample with a second labeling conjugate specific for the second detection probe, the second labeling conjugate comprising a second enzyme such that the second-detection probe-target complex becomes labeled with the second enzyme;
   (iii) contacting the biological sample with a first member of a second pair of click conjugates, the first member of the second pair of click conjugates comprising a tissue reactive moiety, wherein the second enzyme converts the first member of the second pair of click conjugates to a second reactive intermediate which covalently bonds to the biological sample proximally to or directly on the second target to form a second immobilized tissue-click conjugate complex.
   (iv) contacting the biological sample with a second member of a second pair of click conjugates, the second member of the second pair of click conjugates comprising a second reactive moiety capable of reacting with a first reactive moiety of the second immobilized tissue-click conjugate complex such that a covalent bond is formed between second immobilized tissue-click conjugate complex and the second member of the second pair of click conjugates; and
   (v) detecting signals from a second reporter moiety of the second tissue-click conjugate adduct, wherein the second reporter moiety is different than the first reporter moiety.

60. The method of claim 59, wherein the first member of the second pair of click conjugates comprises the conjugate of any of claims 1 to 35.

61. The method of claim 59 or 60, wherein the second member of the second pair of click conjugates comprises the conjugate of any of claims 36 to 50.

62. The method of claim 59 or 60, wherein the second member of the second pair of click conjugates comprises at least one chromophore.

63. The method of claim 59, wherein the first member of the second pair of click conjugates comprises a quinone methide precursor moiety; and wherein the second member of the second pair of click conjugates comprises a chromophore.

64. The method of claim 59, wherein the first member of the second pair of click conjugates comprises a tyramide moiety; and wherein the second member of the second pair of click conjugates comprises a chromophore.

65. The method of any of claims 59 to 64, wherein the second detection probe is a primary antibody, and wherein second first labeling conjugate comprises an anti-antibody antibody.

66. The method of any of claims 59 to 65, wherein the second enzyme is selected from the group consisting of phosphatase, phosphodiesterase, esterase, lipase, amidase, protease, nitroreductase, urease, sulfatase, cytochrome P450, alpha-glucosidase, beta-glucosidase, beta-lactamase, alpha-glucoronidase, beta-glucoronidase, alpha-5-galactosidase, beta-galactosidase, neuraminidase, alpha-lactase and beta-lactase.

67. The method of any of claims 51 to 66, wherein one or more of the steps are performed by an automated system.

68. An immobilized click-conjugate covalently bonded to a tissue sample, the immobilized click-conjugate comprising a first reactive functional group selected from the group consisting of dibenzocyclooctyne, trans-cyclooctene, azide, tetrazine, maleimide, thiol, 1,3-nitrone, aldehyde, ketone, hydrazine, and hydroxylamine.

69. The immobilized click-conjugate of claim 68, wherein the click-conjugate is bonded to the tissue through a tyrosine residue or a nucleophilic species within or on the surface of the tissue sample.

70. A detectable tissue-click adduct complex formed by reacting the immobilized click-conjugate of claims 68 and 69 with a conjugate having Formula (IV):

(IV), wherein

A is selected from the group consisting of dibenzocyclooctyne, trans-cyclooctene, azide, tetrazine, maleimide, thiol, 1,3-nitrone, aldehyde, ketone, hydrazine, and hydroxylamine;

'Linker' is a branched or unbranched, linear or cyclic, substituted or unsubstituted, saturated or unsaturated, group having between 2 and 80 carbon atoms, and optionally having one or more heteroatoms selected from O, N, or S; and Z is selected from the group consisting of a chromophore, a fluorophore, an enzyme, a hapten, and a chelator; and wherein the conjugate of Formula (IV) comprises an A group capable of reacting with the first reactive functional group of the immobilized click-conjugate.

71. The detectable tissue-click adduct complex of claim 70, wherein Z is at least one chromophore.

72. The detectable tissue-click adduct complex of claim 70 or 71, wherein the first reactive functional group is dibenzocyclooctyne and where A of Formula (IV) is selected from the group consisting of an azide or a 1,3-nitrone.

73. The detectable tissue-click adduct complex of claim 70 or 71, wherein the first reactive functional group is trans-cyclooctene and where A of Formula (IV) is a tetrazine.

74. The detectable tissue-click adduct complex of claim 70 or 71, wherein the first reactive functional group is an azide and where A of Formula (IV) is a dibenzocyclooctyne.

75. The detectable tissue-click adduct complex of claim 70 or the detectable tissue-click adduct complex of any of claims 72 to 74, wherein Z is a chelator, and wherein a lanthanide is introduced to the formed detectable tissue-click adduct complex.

Although the disclosure herein has been described with reference to particular embodiments, it is to be understood that these embodiments are merely illustrative of the principles and applications of the present disclosure. It is therefore understood that numerous modifications may be made to the illustrative embodiments and that other arrangements may be devised without departing from the spirit and scope of the present disclosure as defined by the appended claims.

The invention claimed is:

1. A conjugate having Formula (III):

(III), wherein

M is a cinnamic acid moiety or a compound having Formula (111a),

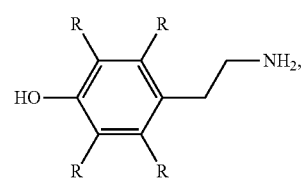
(IIIa)

wherein each R group is independently selected from hydrogen or a lower alkyl group having between 1 and 4 carbon atoms; wherein the cinnamic acid moiety is covalently coupled to the 'Linker' via the carboxylic acid group of the cinnamic acid moiety, and wherein the compound having Formula (111a) is covalently coupled to the 'Linker' via the amino moiety of the compound having Formula (111a);

A is a dibenzocyclooctyne; and

'Linker' is a branched or unbranched, linear or cyclic, substituted or unsubstituted, saturated or unsaturated, group having between 2 and 80 carbon atoms, and optionally having one or more heteroatoms selected from O, N, or S.

2. The conjugate of claim 1, wherein 'Linker' has the formula (Ia)

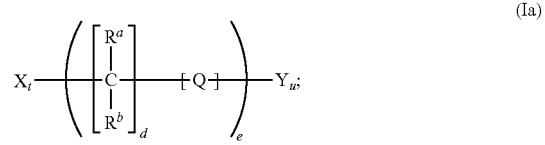
(Ia)

wherein d and e are integers each independently ranging from 2 to 20;

t and u are independently 0 or 1;

Q is a bond, O, S, or $N(R^c)(R^d)$;

$R^a$ and $R^b$ are independently H, a $C_1$-$C_4$ alkyl group, F, Cl, or $N(R^c)(R^d)$;

$R^c$ and $R^d$ are independently $CH_3$ or H; and

X and Y are independently a branched or unbranched, linear or cyclic, substituted or unsubstituted, saturated or unsaturated group having between 1 and 12 carbon atoms and optionally having one or more O, N, or S heteroatoms.

3. The conjugate of claim 1, wherein $R^a$ and $R^b$ are each hydrogen.

4. The conjugate of claim 2, wherein Q is oxygen.

5. The conjugate of claim 1, wherein $R^a$ and $R^b$ are each hydrogen, Q is oxygen, and e ranges from 2 to 10.

6. The conjugate of claim 1, wherein the Linker comprises one or more alkylene oxide groups.

7. The conjugate of claim 1, wherein the Linker comprises at least three PEG groups.

8. The conjugate of claim 1, wherein the Linker comprises five PEG groups.

9. The conjugate of claim 1, wherein A comprises dibenzocyclooctyne and the Linker comprises at least three PEG groups.

10. The conjugate of claim 1, wherein the Linker comprises at least three PEG groups and at least two carbonyl groups.

11. The conjugate of claim 1, wherein A comprises dibenzocyclooctyne and wherein the Linker is water soluble.

12. The conjugate of claim 1, wherein the conjugate is

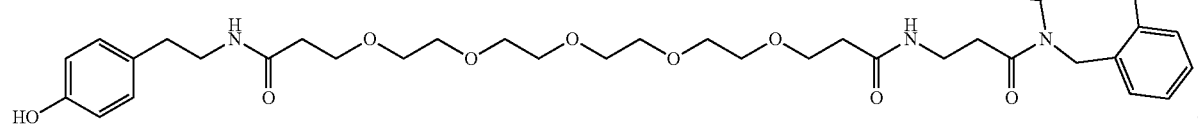

13. A conjugate having Formula (III):

A—[Linker]—M          (III), wherein

M is a compound having Formula (111a),

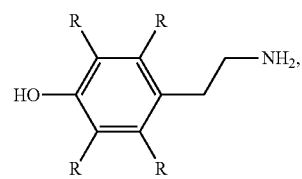

wherein each R group is independently selected from hydrogen or lower alkyl group having between 1 and 4 carbon atoms, wherein said 'M is covalently coupled to the 'Linker' via the amino moiety of the compound having the Formula (111a);

A is a dibenzocyclooctyne; and

'Linker' is a branched or unbranched, linear or cyclic, substituted or unsubstituted, saturated or unsaturated, group having between 2 and 80 carbon atoms, and optionally having one or more heteroatoms selected from O, N, or S.

14. The conjugate of claim 13, wherein the Linker comprises at least three alkylene oxide groups.

15. The conjugate of claim 13, wherein the Linker comprises at least five alkylene oxide groups.

16. The conjugate of claim 14, wherein the Linker further comprises at least two carbonyl groups.

17. The conjugate of claim 16, wherein at least one R group comprises H.

18. A conjugate having Formula (III):

A—[Linker]—M          (III), wherein

M is a compound having any one of Formulas (111c) or (111d),

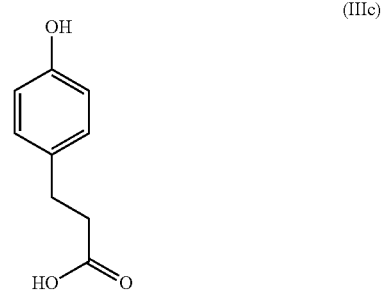

-continued

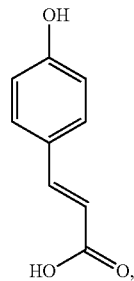

wherein each R group is independently selected from hydrogen or lower alkyl group having between 1 and 4 carbon atoms, wherein the compound having any one of Formulas (111c) or (111d) is covalently coupled to the 'Linker' via the carboxylic acid of the compound having any one of the Formulas (111c) of (111d);

A is a dibenzocyclooctyne; and

'Linker' is a branched or unbranched, linear or cyclic, substituted or unsubstituted, saturated or unsaturated, group having between 2 and 80 carbon atoms, and optionally having one or more heteroatoms selected from O, N, or S.

\* \* \* \* \*